(12) United States Patent
Bily et al.

(10) Patent No.: US 9,700,589 B2
(45) Date of Patent: Jul. 11, 2017

(54) COMPOSITIONS AND METHODS FOR IMPROVED MUSCLE METABOLISM

(71) Applicant: Naturex SA, Avignon (FR)

(72) Inventors: Antoine Charles Bily, Vedène (FR); Marjolaine Meyer, Pfettisheim (FR); Karl Chevalier, Salon de Provence (FR); Lise Laurençon, Montfavet (FR); Nicolas Feuillere, Courthezon (FR); Marc Roller, Morieres les Avignon (FR); Simona Birtic, Cavaillon (FR)

(73) Assignee: NATUREX SA, Avignon (FR)

( * ) Notice: Subject to any disclaimer, the term of this patent is extended or adjusted under 35 U.S.C. 154(b) by 0 days.

(21) Appl. No.: 14/612,973

(22) Filed: Feb. 3, 2015

(65) Prior Publication Data

US 2016/0220624 A1 Aug. 4, 2016

(51) Int. Cl.
| A61K 36/00 | (2006.01) |
| A61K 36/41 | (2006.01) |
| A61K 36/28 | (2006.01) |
| A61K 31/575 | (2006.01) |
| A61K 31/7028 | (2006.01) |
| A61K 9/00 | (2006.01) |

(52) U.S. Cl.
CPC ............ *A61K 36/41* (2013.01); *A61K 9/0053* (2013.01); *A61K 31/575* (2013.01); *A61K 31/7028* (2013.01); *A61K 36/28* (2013.01)

(58) Field of Classification Search
None
See application file for complete search history.

(56) References Cited

U.S. PATENT DOCUMENTS

| 7,618,639 | B2 | 11/2009 | Olalde Rangel | |
| 2002/0127285 | A1* | 9/2002 | Xiu | A61K 36/41 424/725 |
| 2008/0089946 | A1* | 4/2008 | Olalde Rangel | A61K 36/28 424/548 |
| 2011/0021474 | A1 | 1/2011 | Kramer et al. | |
| 2013/0236578 | A1 | 9/2013 | Terezov | |
| 2014/0314870 | A1 | 10/2014 | Elistratov | |

FOREIGN PATENT DOCUMENTS

| CN | 102631573 A | * 8/2012 |
| CN | 102727560 A | 10/2012 |
| CN | 103432452 A | * 12/2013 |
| EP | 2 407 035 A1 | 1/2012 |
| RU | 2 066 963 C1 | 9/1996 |
| RU | 2 174 397 C1 | 10/2001 |
| RU | 2259840 C2 | * 9/2005 |
| SG | 175252 A1 | 11/2011 |
| WO | WO 2013/088084 A1 | 6/2013 |

OTHER PUBLICATIONS

Pooja et al, Anti-inflammatory activity of Rhodiola rosea—"A second-generation adaptogen". Phytotherapy research : PTR, (Aug. 2009) vol. 23, No. 8, pp. 1099-1102.*
Azizov et al., "The Effect of Elton, Leveton, Fitoton and Adapton on the Work Capacity of Experimental Animals", Eksp Klin Farmakol, 1998, pp. 61-63, vol. 61, No. 3, Moscow, Russia.
Azizov, "Effects of Eleutherococcus, Elton, Leuzea, and Leveton on the Blood Coagulation System During Training in Athletes", Eksp Klin Farmakol, 1997, pp. 58-60, vol. 50, No. 5, Moscow, Russia.
Broussard et al., "IL-1B Impairs Insulin-Like Growth Factor I-Induced Differentiation and Downstream Activation Signals of the Insulin-Like Growth Factor I Receptor in Myoblasts", Journal of Immunology, 2004, vol. 172, pp. 7713-7720.
Cheng et al., "Continuous Infusion of 20-Hydroxyecdysone Increased Mass of Triceps Brachii in C57BL/6 Mice", NIH Public Access, Phytother Res., Jan. 2013, vol. 27, No. 1, pp. 107-111.
Cheng et al., "In vitro production of metabolism-enhancing phytoecdysteroids from *Ajuga turkestanica*", Plant Cell Tissue Organ Culture, 2008, vol. 93, pp. 73-83.
Chermnykh et al., "The Action of Methandrostenolone and Ecdysterone on the Physical Endurance of Animals and on Protein Metabolism in the Skeletal Muscles", Farmakol Toksikol, 1988, vol. 51, No. 6, pp. 57-60, Russia.
Gadzhieva et al., "A Comparative Study of the Anabolic Action of Ecdysten, Leveton and Prime Plus, Preparations of Plant Origin", Eksp Klin Farmakol, 1995, vol. 58, No. 5, pp. 46-48, Russia.
Gorelick-Feldman et al., "Phytoecdysteroids Increase Protein Synthesis in Skeletal Muscle Cells", Journal of Agricultural and Food Chemistry, 2008, vol. 56, pp. 3532-3537.
Kazi et al., "PRAS40 Regulates Protein Synthesis and Cell Cycle in C2C12 Myoblasts", Molecular Medicine, Sep.-Oct. 2010, vol. 16, No. 9-10, pp. 359-371.
Kokoska et al., "Chemistry and Pharmacology of *Rhaponticum carthamoides*: A review", Phytochemistry, 2009, vol. 70, pp. 842-855.
Kokoska et al., "Screening of some Siberian medicinal plants for antimicrobial activity", Journal of Ethnopharmacology, 2002, vol. 82, pp. 51-53.
Koudela et al., :Stimulation of Growth and Development in Japanese quails after oral administration of ecdysteroid-containing diet, European Journal of Entomology, 1995, vol. 92, pp. 349-354.
Lagirand-Cantaloube et al., "Inhibition of Atrogin-1/MAFbx Mediated MyoD Proteolysis Prevents Skeletal Muscle Atrophy In Vivo", PLoS ONE, 2009, vol. 4, No. 3, pp. 1-11.
Latres et al., "Insulin-like Growth Factor-1 (IGF-1) Inversely Regulates Atrophy-induced Genes via the Phosphatidylinositol 3-Kinase/Akt/Mammalian Target of Rapamycin (PI3K/Akt/mTOR) Pathway", The Journal of Biological Chemistry, Jan. 2005, vol. 280, No. 4, pp. 2737-2744.

(Continued)

*Primary Examiner* — Qiuwen Mi
(74) *Attorney, Agent, or Firm* — Stephen J. Weyer, Esq.; Stites & Harbison, PLLC

(57) ABSTRACT

A composition for improving muscle metabolism in a subject and methods for manufacturing and using same. Embodiments include compositions having an extract of *Rhaponticum* and an extract of *Rhodiola*. An extract of *Rhaponticum* may include amounts of ecdysterones including 20-hydroxyecdysone. An extract of *Rhodiola* my include salidrosides and rosavins, including rosavin. Suitable ingestion dosages of the composition may be operable to increase protein synthesis and reduce protein proteolysis in a subject.

26 Claims, 34 Drawing Sheets

(56) References Cited

OTHER PUBLICATIONS

Lee et al., "Regulation of Muscle Growth by Multiple Ligands Signaling Through Activin Type II Receptors", Proceedings of the National Academy of Science of the United States of America, Dec. 2005, vol. 102, No. 50, pp. 18117-18122.
Petkov et al., "Pharmacological Investigations on *Rhaponticum carthamoides*", Planta Medica, 1984, pp. 205-209.
Slama et al., "Insect hormones in vertebrates: anabolic effects of 20-hydroxyecdysone in Japanese quail", Experientia, 1996, vol. 52, pp. 702-706.
Stitt et al., "The IGF-1/P13K/Akt Pathway Prevents Short Article Expression of Muscle Atrophy-Induced Ubiquitin Ligases by Inhibiting FOXO Transcription Factors", Molecular Cell, May 2004, vol. 14, pp. 395-403.
Syrov, "Comparative Experimental Investigation of the Anabolic Activity of Phytoecdysteroids and Steranbols", Pharmaceutical Chemistry Journal, 2000, vol. 34, No. 4, pp. 193-197.
Timofeev, "Ecological Relations of Agricultural Populations of Ecdysteroid-Containing Plants *Rhaponticum carthamoides* (Willd.) Iljin and *Serratula coronate* L. with Herbivorous Insects Report 2. Composition Variability of Phytoecdysteroids in Agrocenoses and Their Role in the Vulnerability of Plants to Phytophagans", Contemporary Problems of Ecology, 2009, vol. 2, No. 6, pp. 531-541.
Toth et al., "20-Hydroxyecdysone increases fiber size in a muscle-specific fashion in rat", Phytomedicine, 2008, vol. 15, pp. 691-698.
Trendelenburg et al., "Myostatin reduces Akt/TORC1/p70S6K signaling, inhibiting myoblast differentiation and myotube size", American Journal of Physiology—Cell Physiology, 2009, vol. 296, pp. 1258-1270.
Volodin et al., "20-Hydroxyecdysone—Plant Adaptogen: An Anabolic Effect, Possible use in Sports Nutrition", Vopr Pitan, 2013, vol. 82, No. 6, pp. 24-30, Russia.
Welle et al., "Sex-Related Differences in Gene Expression in Human Skeletal Muscle", PLoS ONE, Jan. 2008, No. 1, pp. 1-7.
Welle et al., "Stimulation of Skeletal Muscle Myofibrillar Protein Synthesis, p70 S6 Kinase Phosphorylation, and Ribosomal Protein S6 Phosphorylation by Inhibition of Myostatin in Mature Mice", American Journal of Physiology—Endrocrinology and Metabolism, Mar. 2009, vol. 296, No. 3, pp. 567-572.
Wilborn et al., "Effects of Methoxyisoflavone, Ecdysterone, and Sulfo-Polysaccharide Supplementation on Training Adaptations in Resistance-Trained Males", Journal of International Society of Sports Nutrition, 2006, vol. 3, No. 2, pp. 19-27.
Zubeldia et al., "In Vitro Characterization of the Efficacy and Safety Profile of a Proprietary *Ajuga turkestanica* Extract", Chinese Medicine, 2012, vol. 3, pp. 215-222.
International Search Report and Written Opinion dated Jun. 10, 2016 in International Application No. PCT/IB2016/000322.
Antoshechkin Anatoly, et al., "Influence of Plant Extract Complex "Admax" on Global Gene Expression Levels in Cultured Human Fibroblasts", 2008, pp. 293-304, vol. 5, No. 3, Journal of Dietary Supplements.
Cheng, et al., "Continuous infusion of 20-hydroxyecdysone increased mass of triceps brachii in C57BL/6 mice", Apr. 1, 2013, pp. 107-111, Phytotherapy Research, Wiley, UK, abstract.
Li H. B., et al., "Salidroside stimulated glucose uptake in skeletal muscle cells by activating AMP-activated protein kinase", Jul. 7, 2008, pp. 165-169, vol. 588, No. 2-3, European Journal of Pharmacology, Elsevier Science, NL.
Hernandez-Santana A., et al., "A Rhodiola rosea root extract protects skeletal muscle cells against chemically induced oxidative stress by modulating heat shock protein 70 (HSP70) expression", Apr. 2014, pp. 623-628, vol. 28, No. 4, Phytotherapy Research Apr. 2014 John Wiley and Sons Ltd. GBR.

* cited by examiner

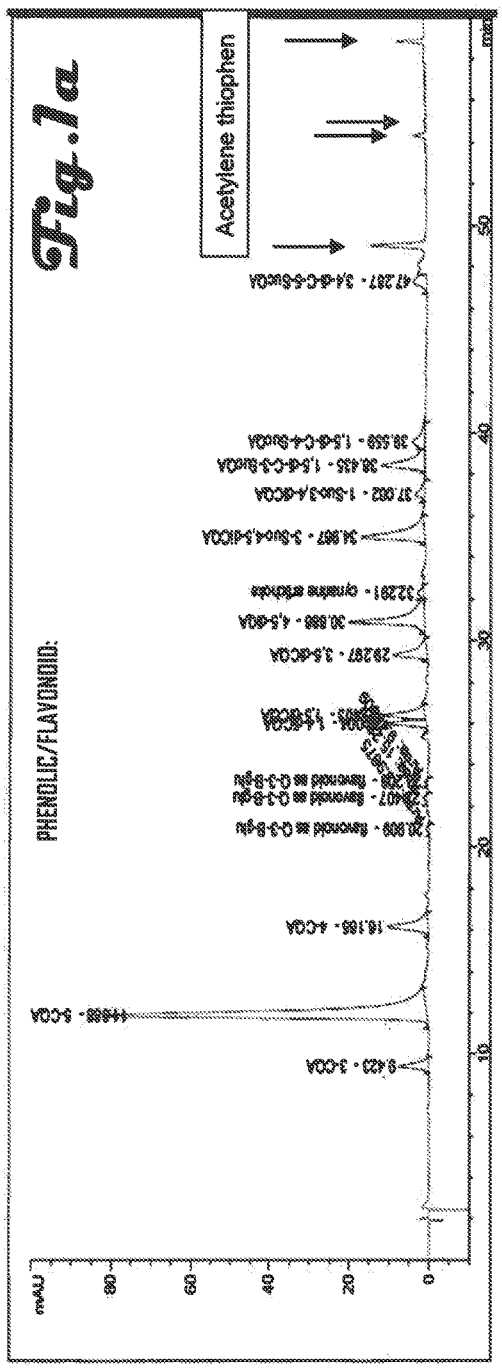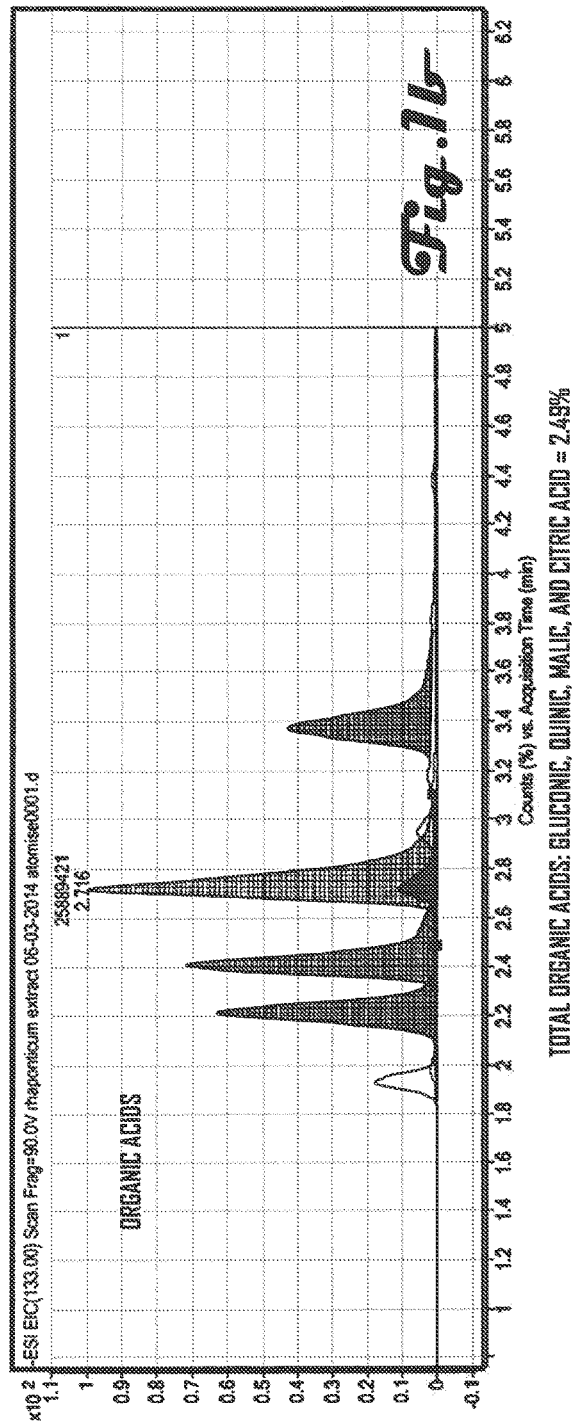

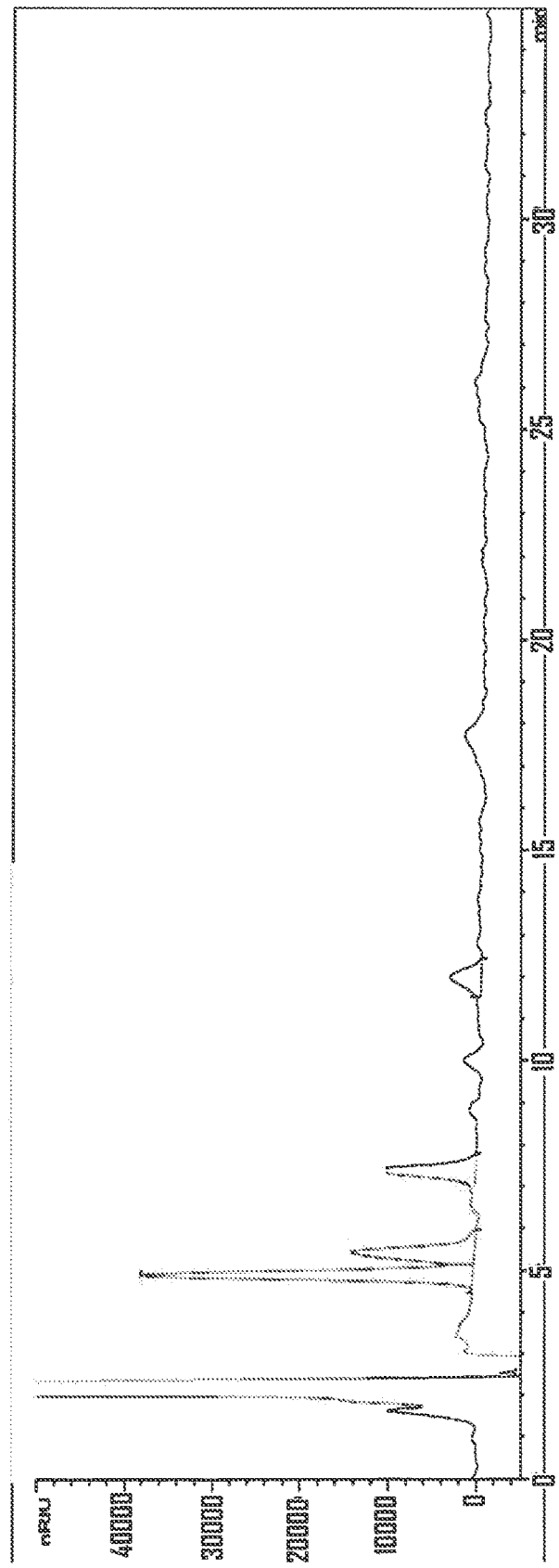

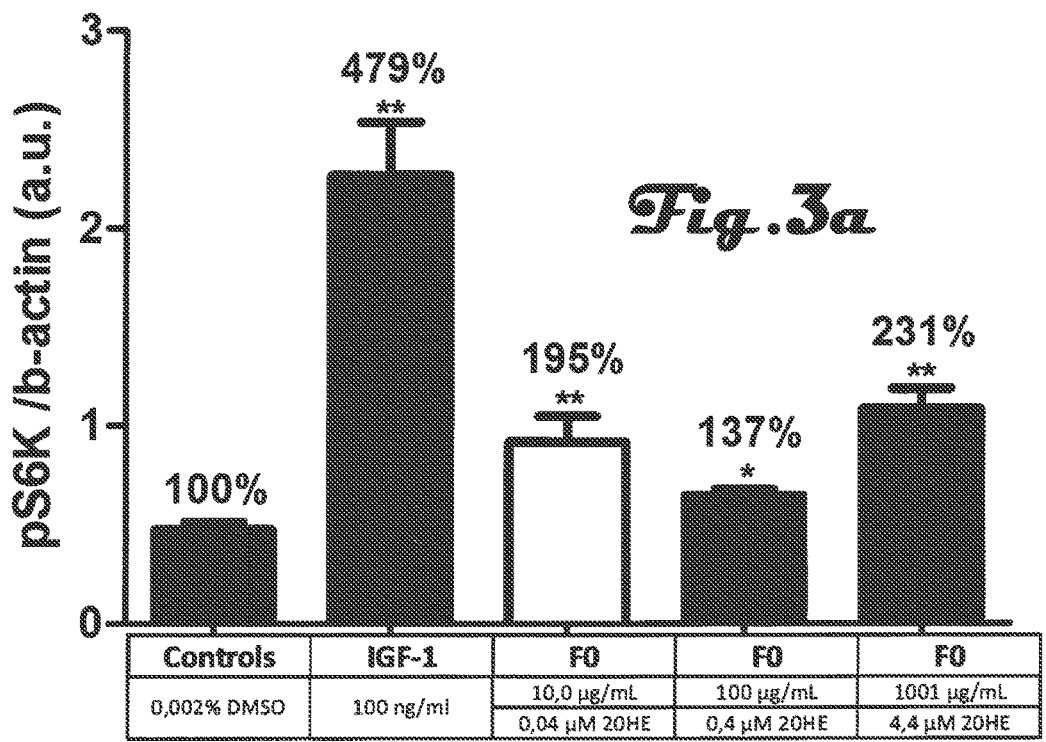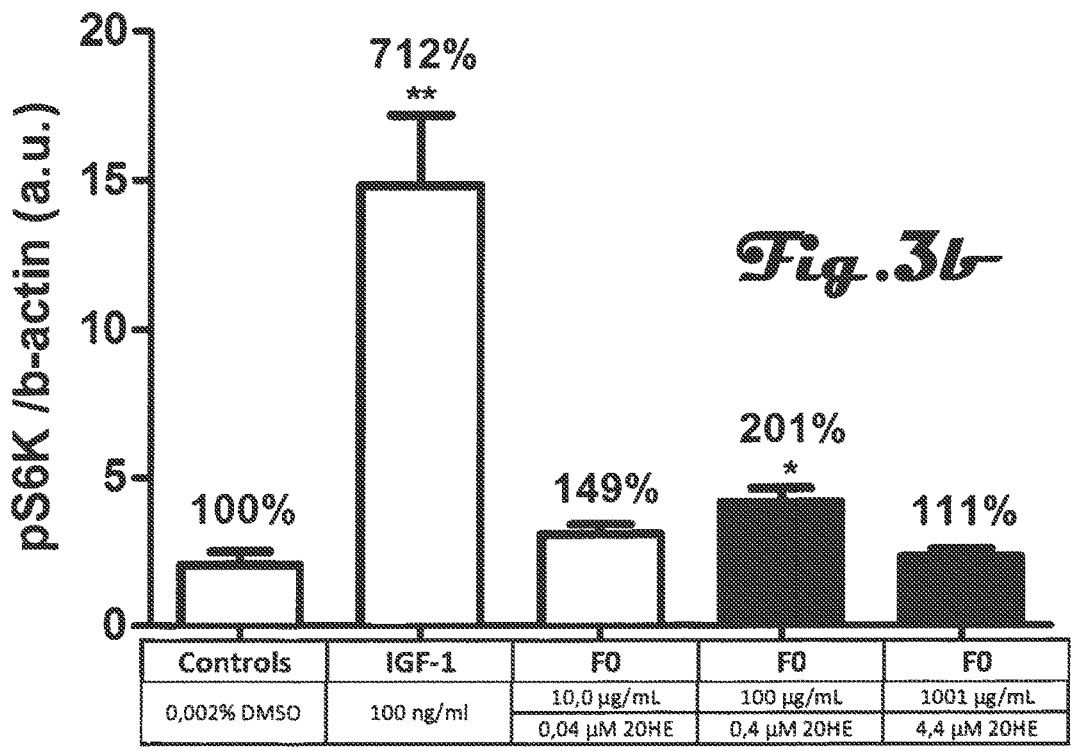

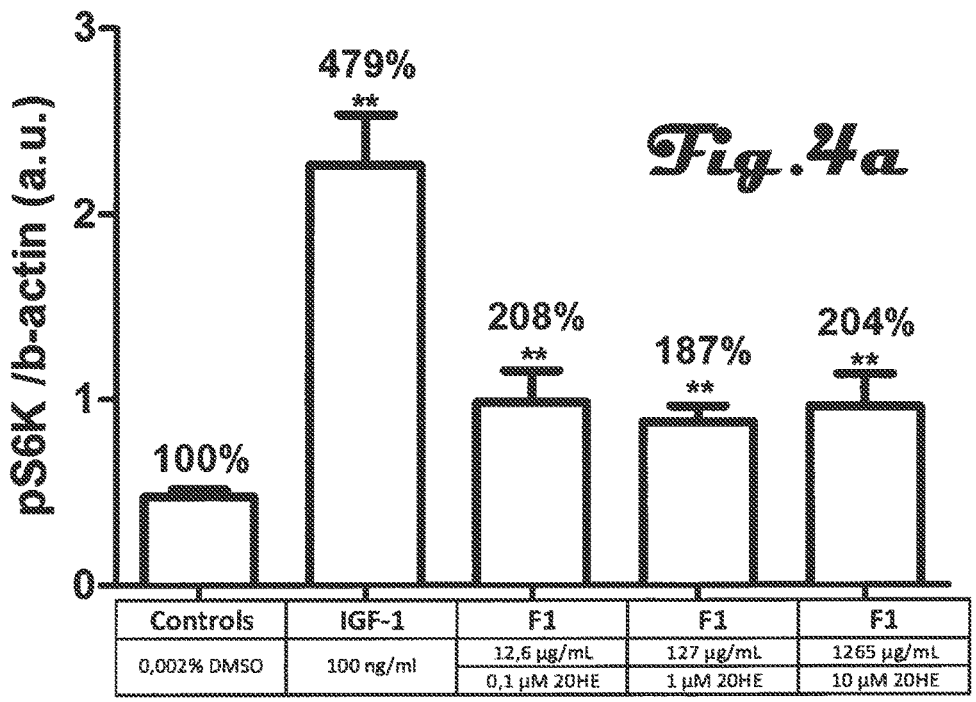
*F1 fraction at 1264.8μg/ml final: incomplete solubility in Krebs*
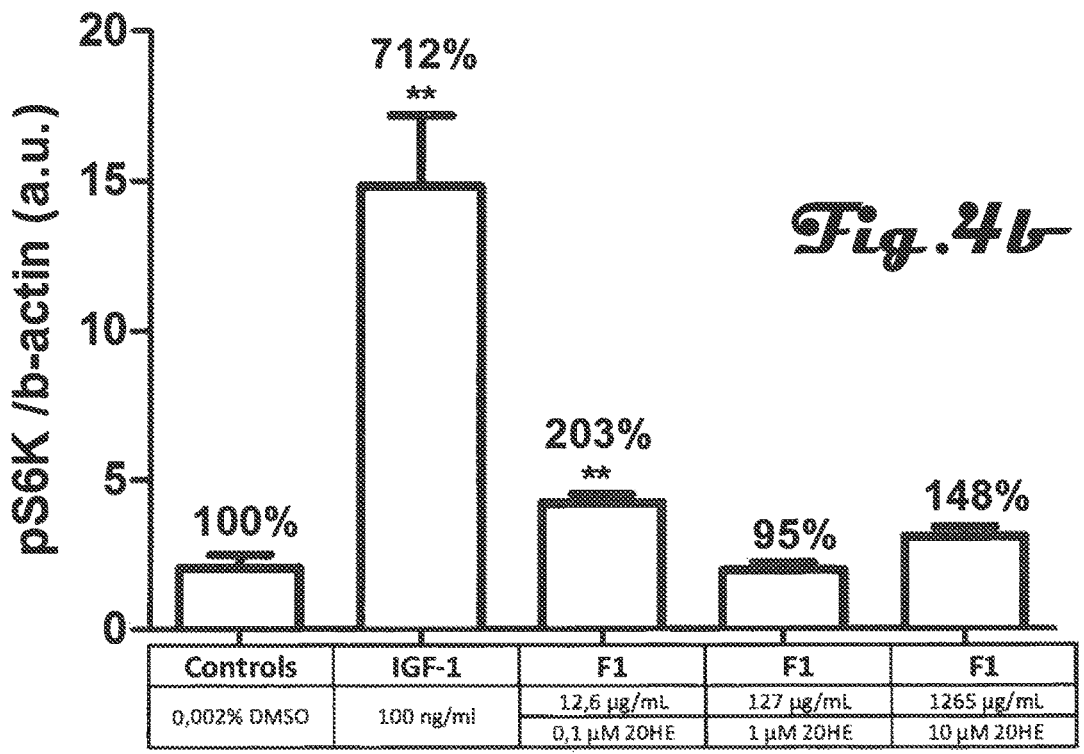

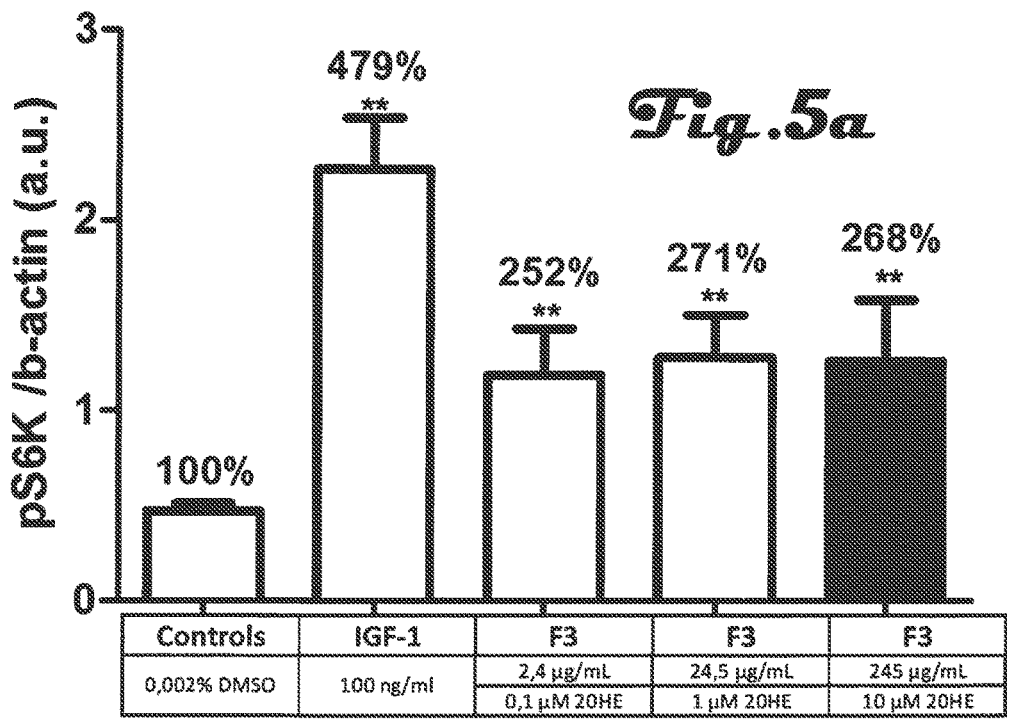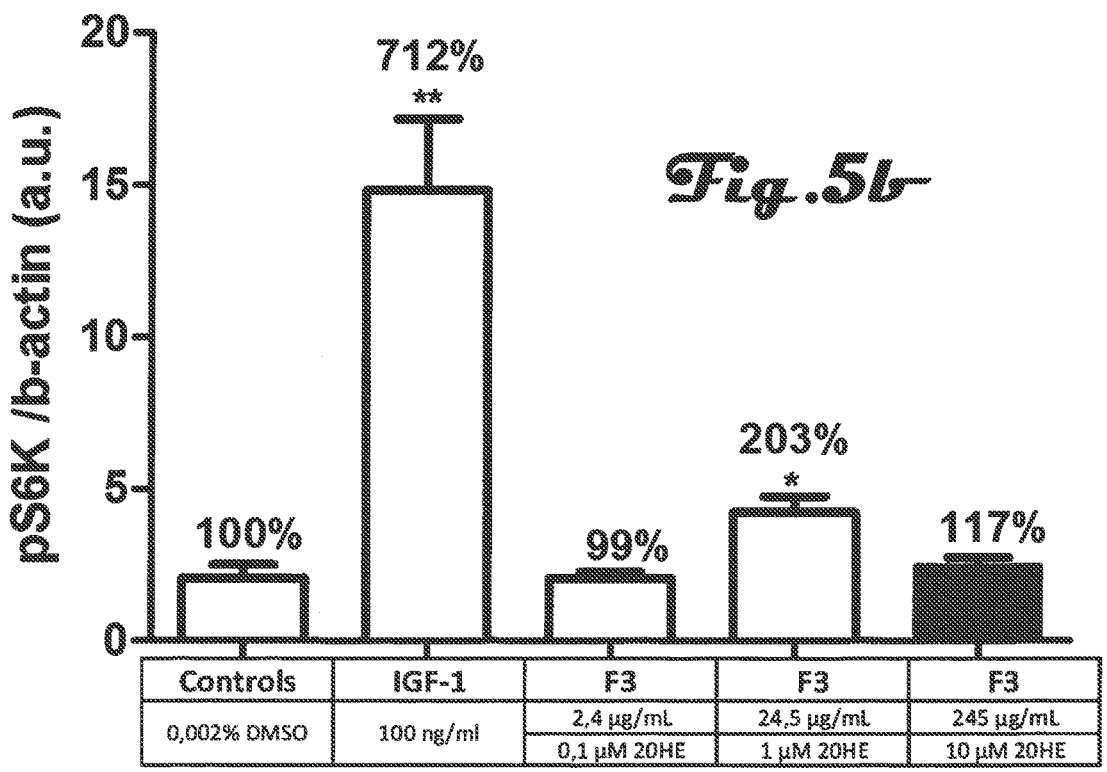

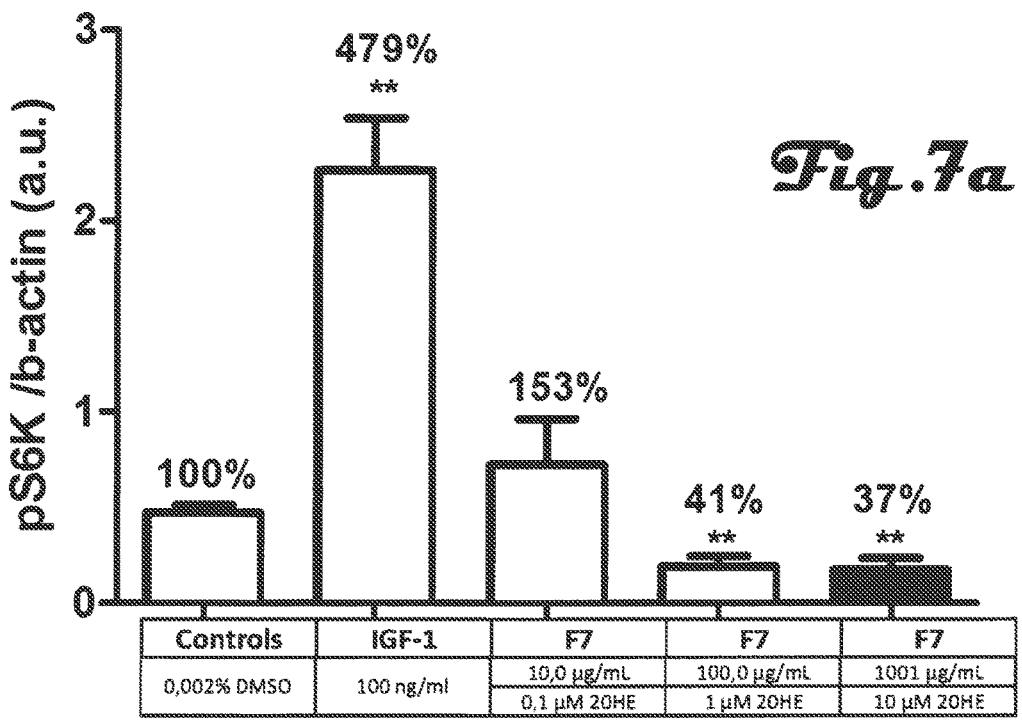
*F7 fraction at 1001µg/ml final: incomplete solubility in Krebs*
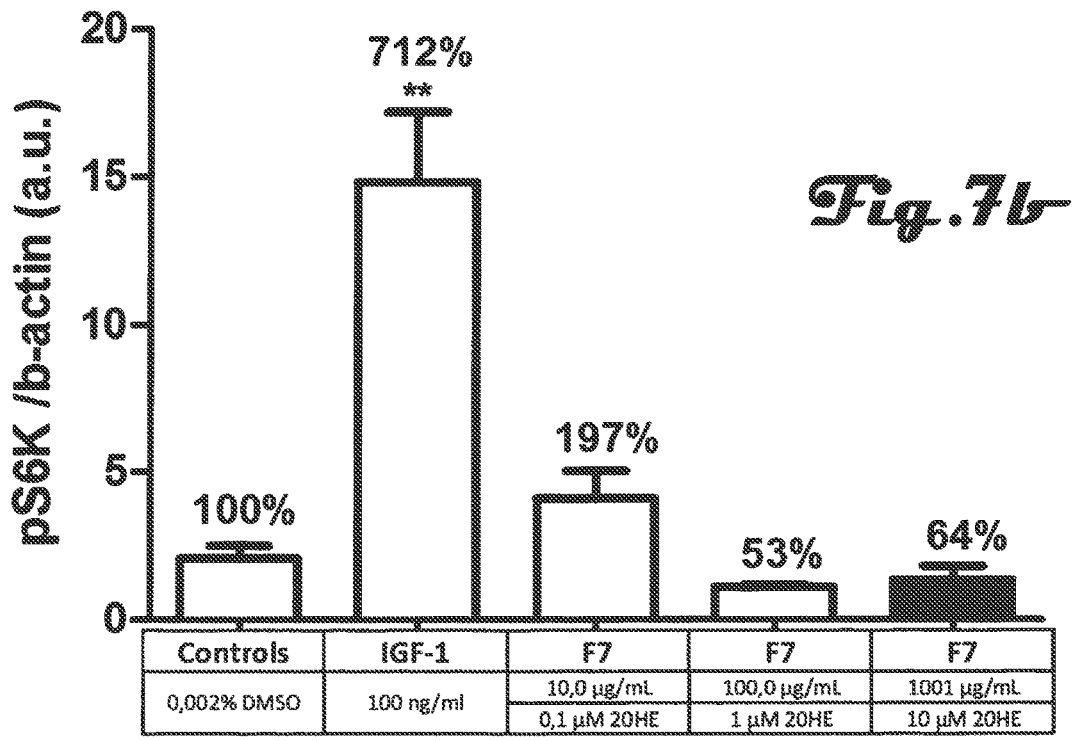

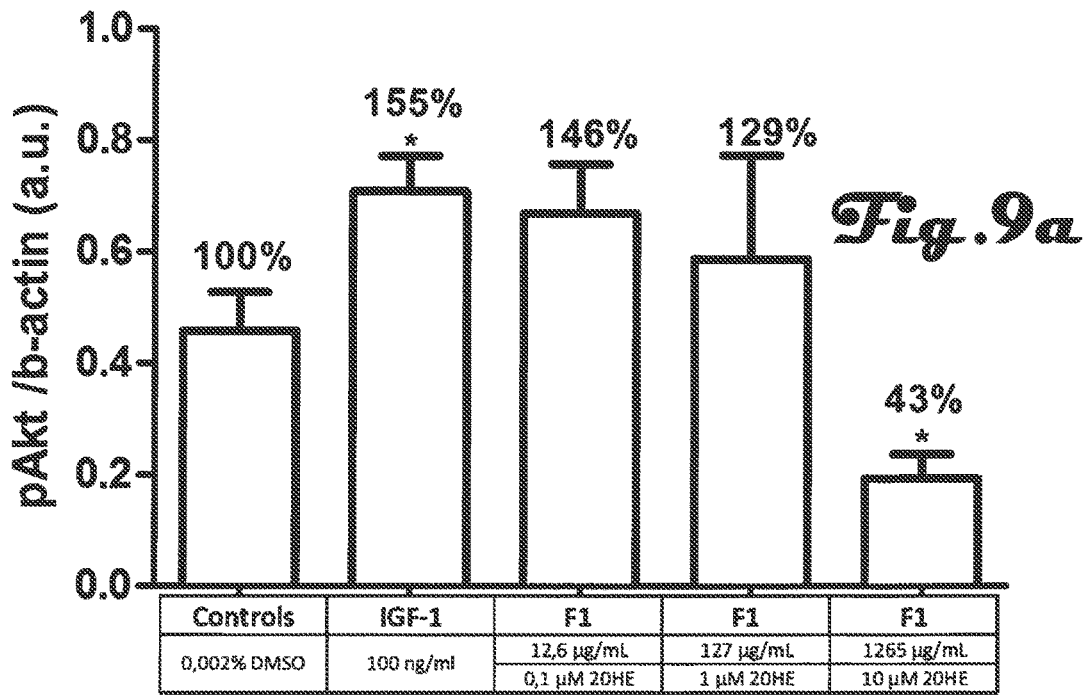
*F1 fraction at 1264.8µg/ml final incomplete solubility in Krebs*
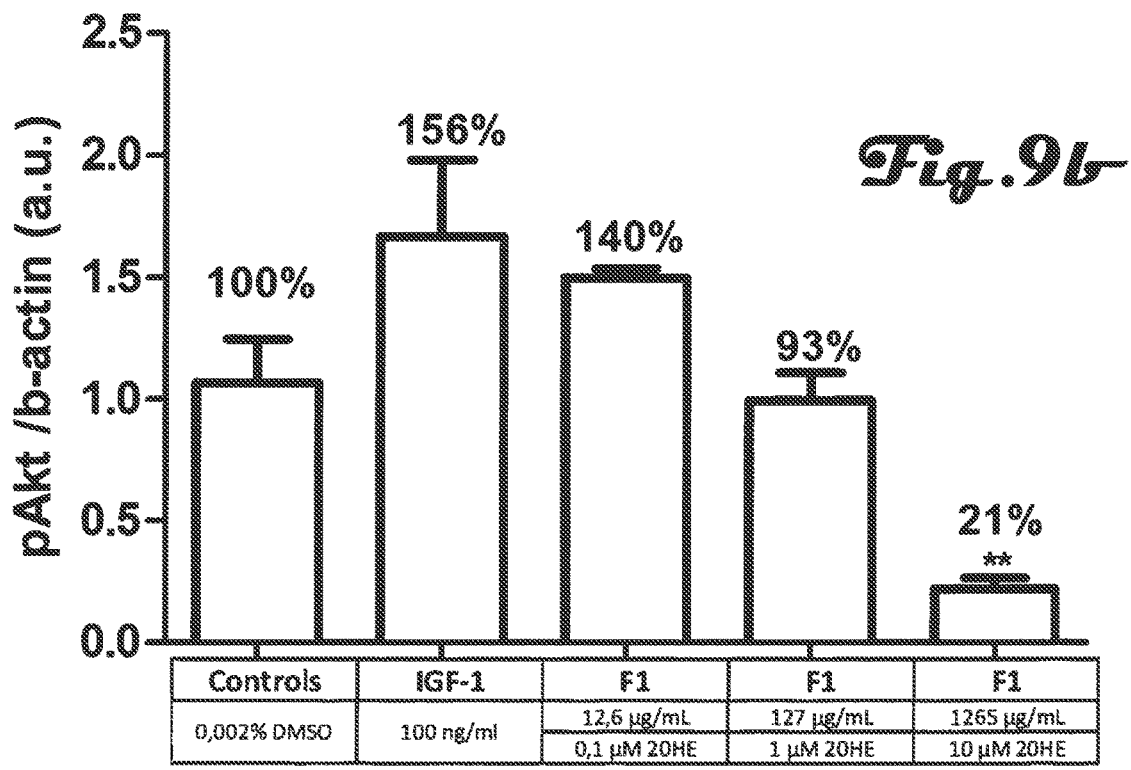

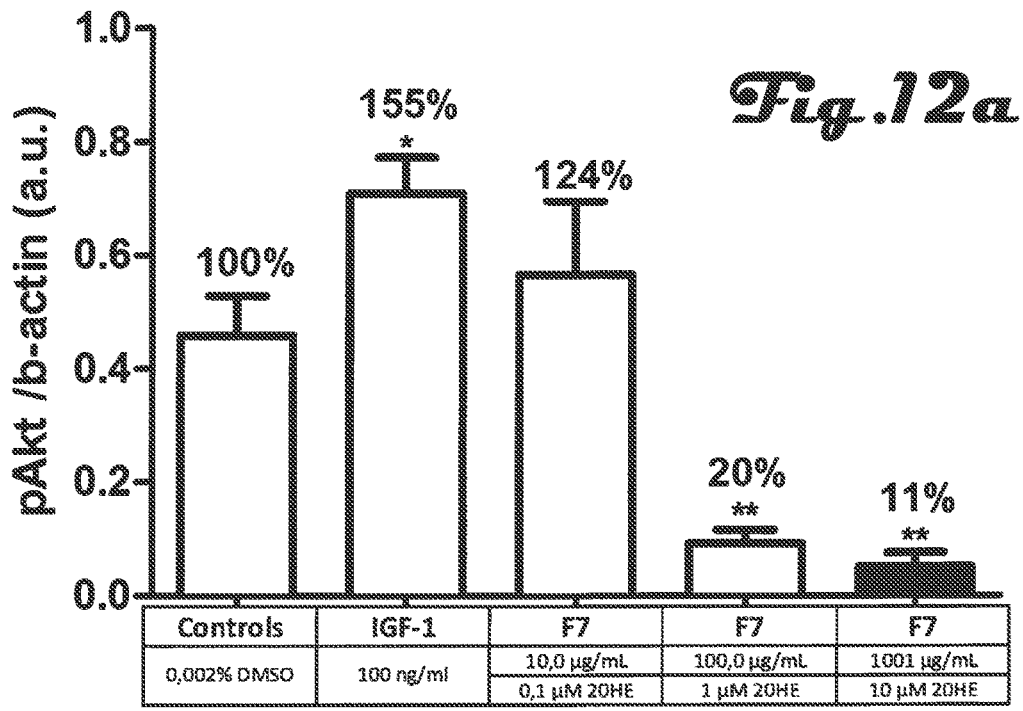
*F7 Fraction at 1001μg/ml final: incomplete solubility in Krebs*
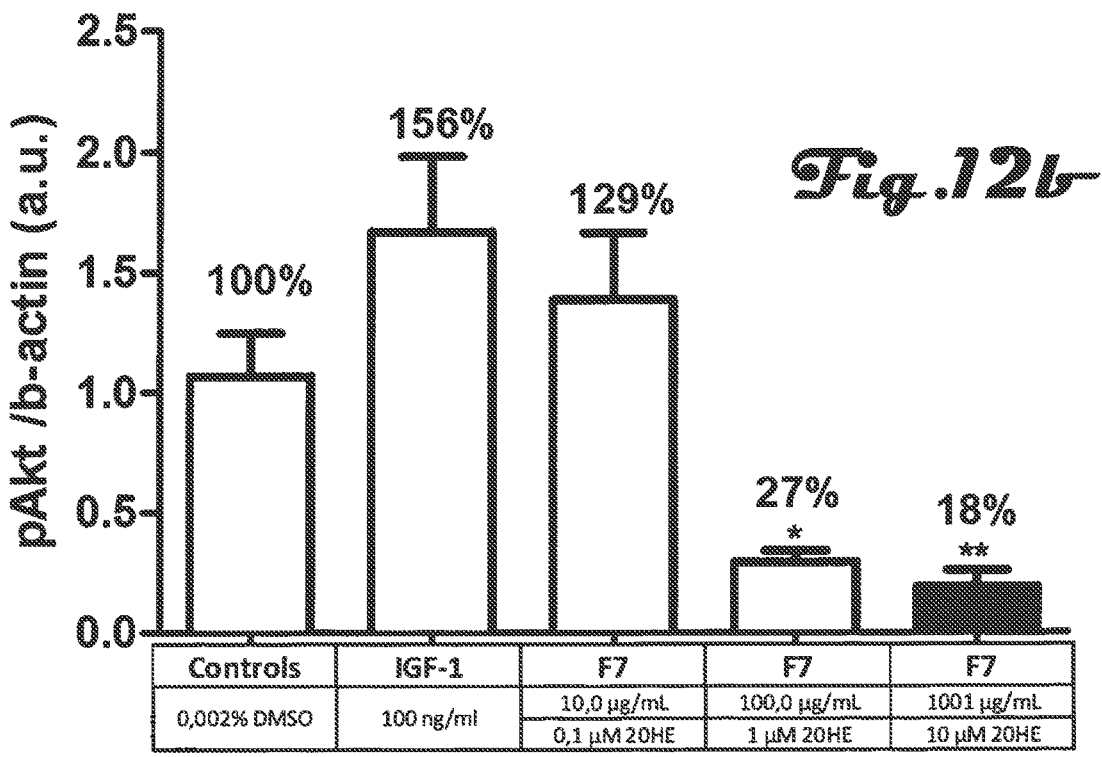

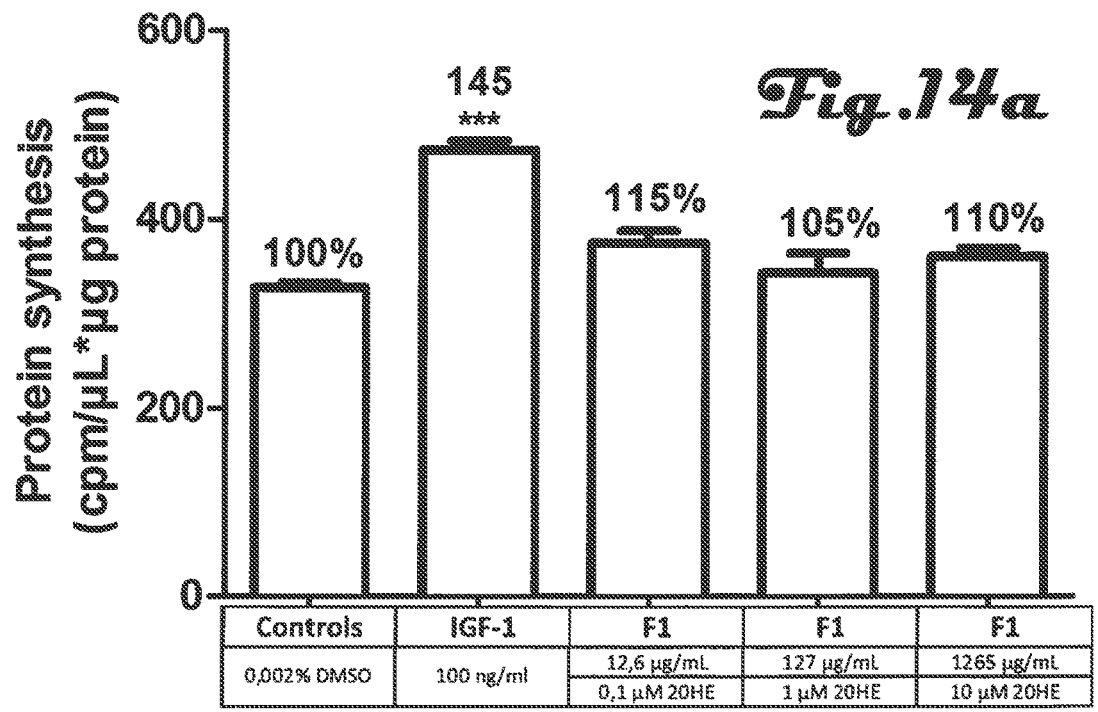
*F1 fraction at 1264.8μg/ml final: incomplete solubility in Krebs*
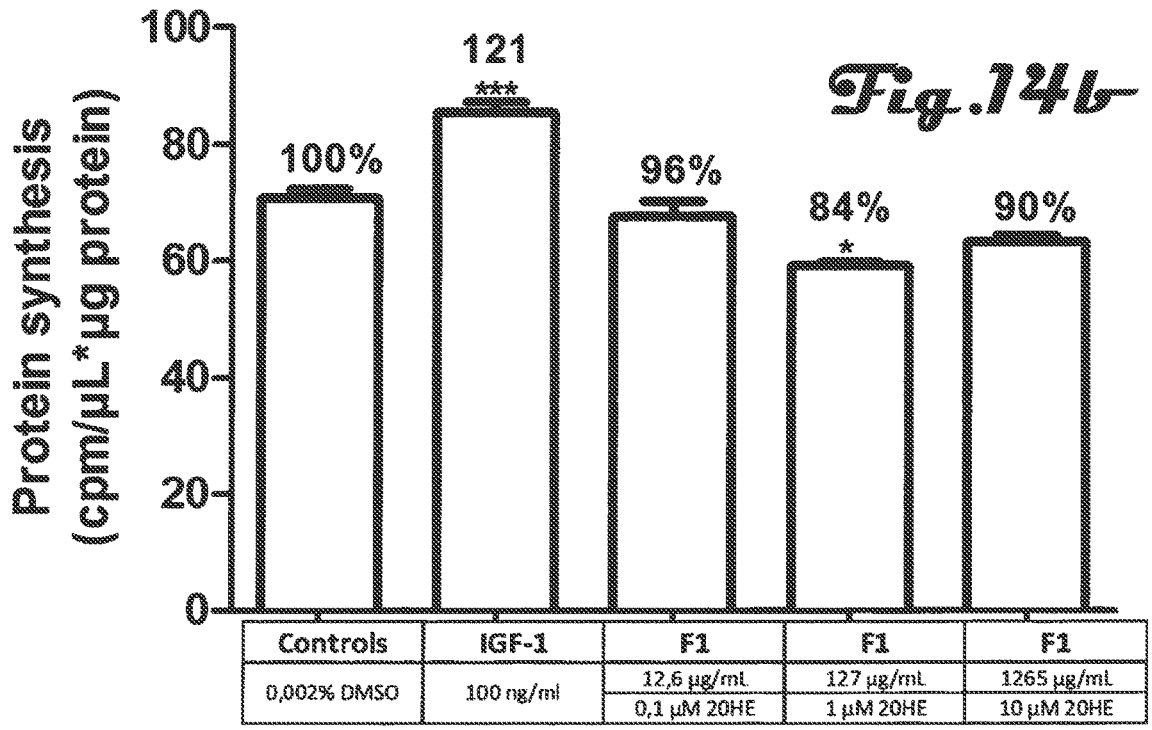

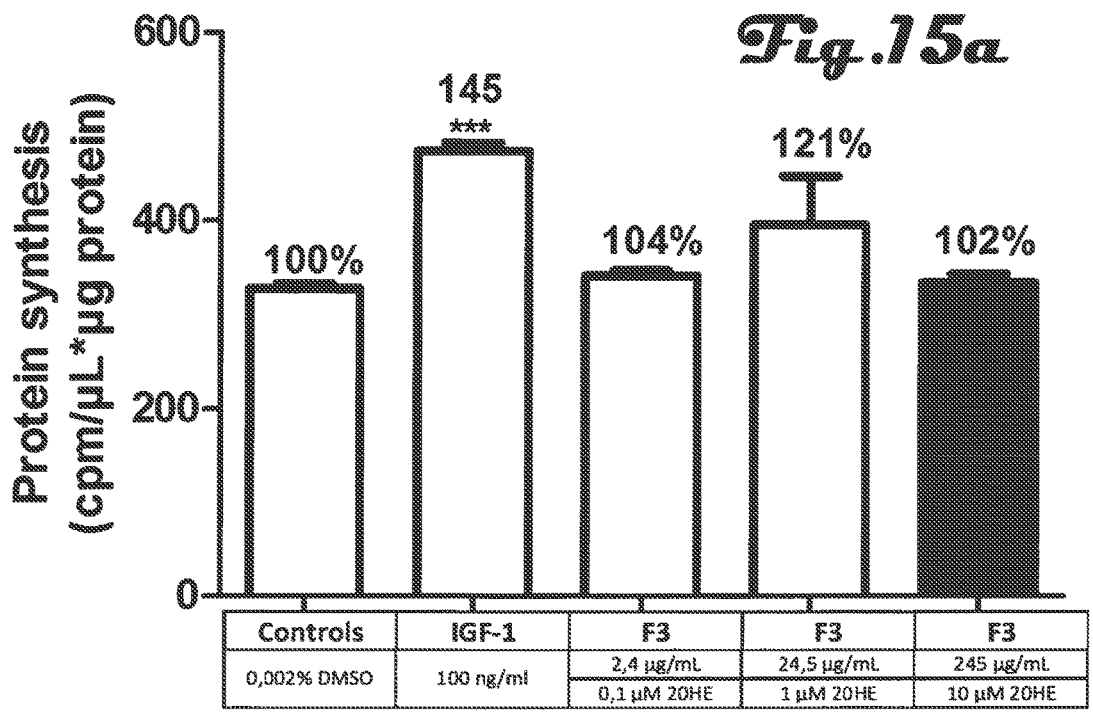
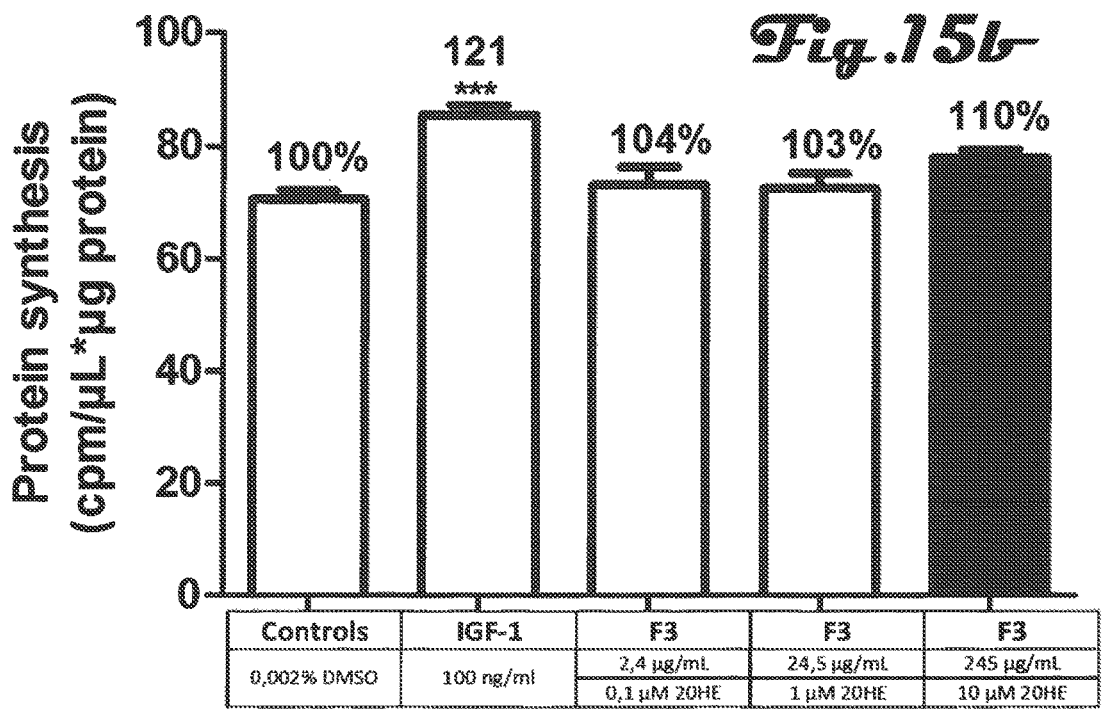

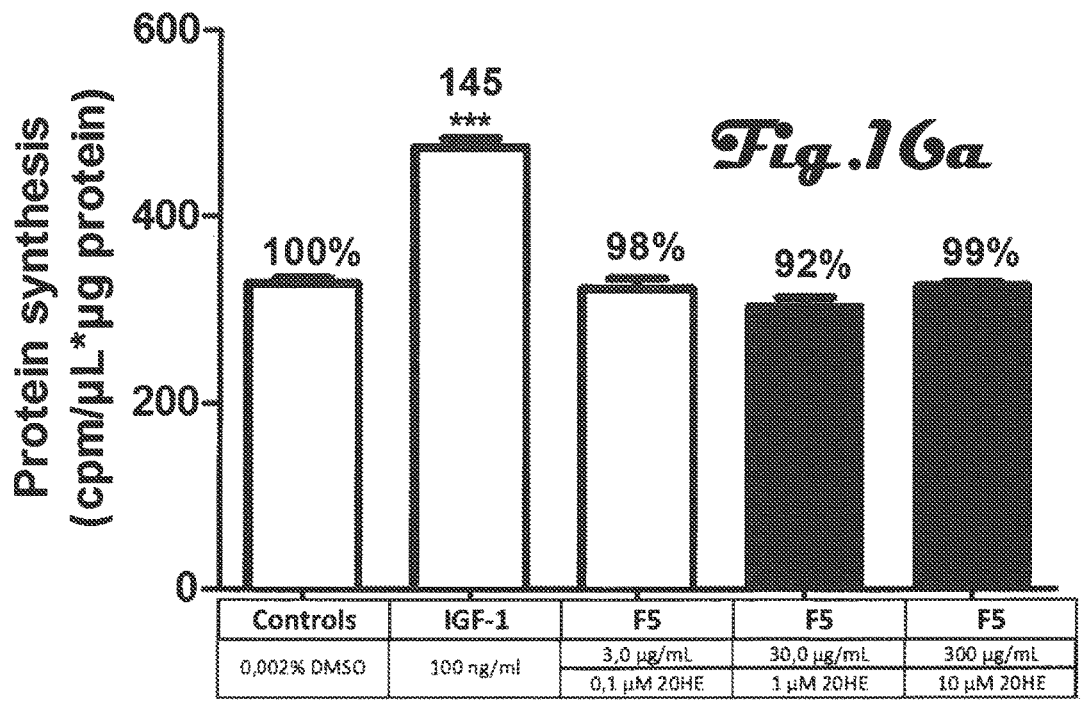
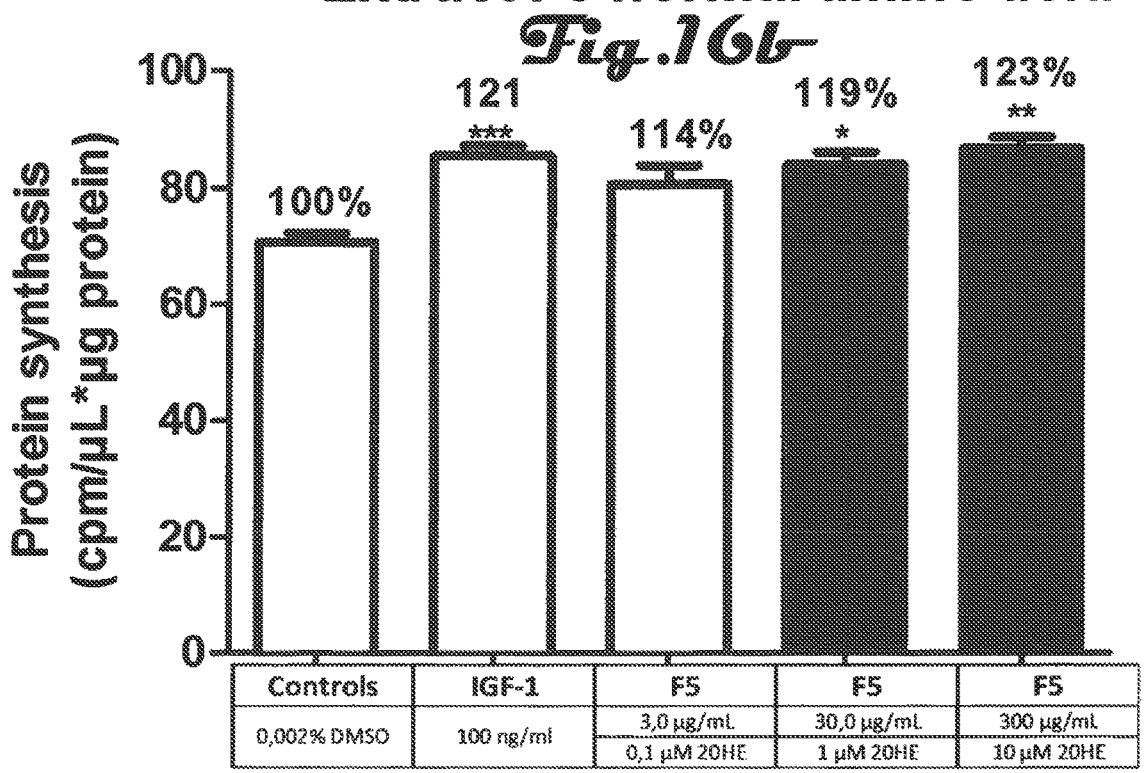

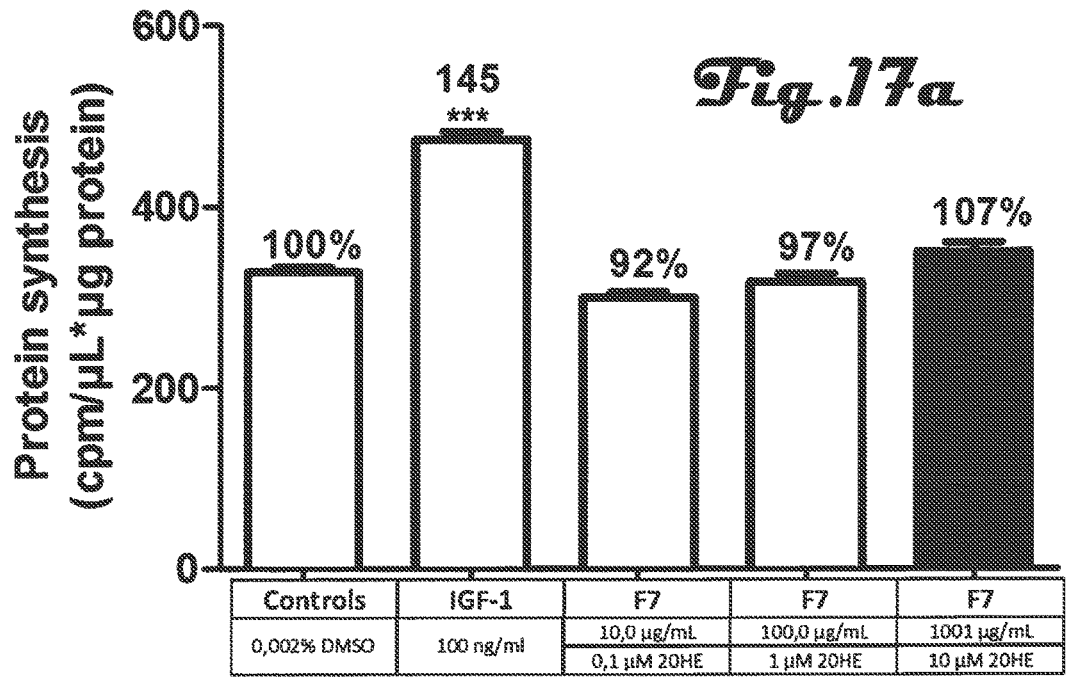
*F7 Fraction at 1001 µg/ml final: incomplete solubility in Krebs*
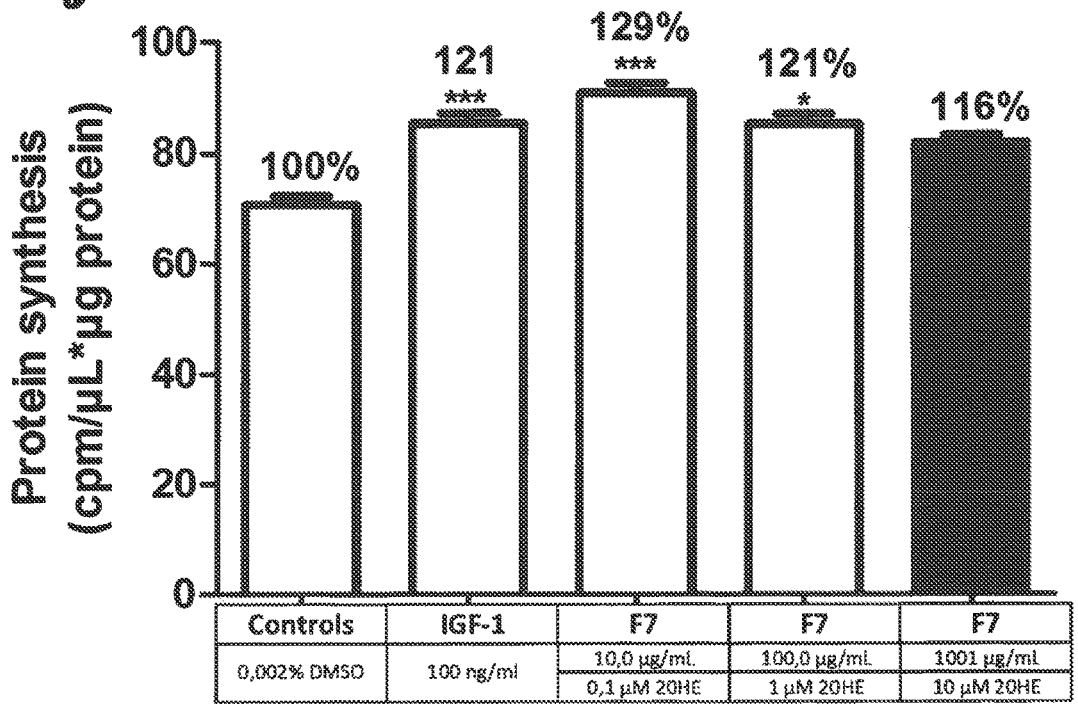

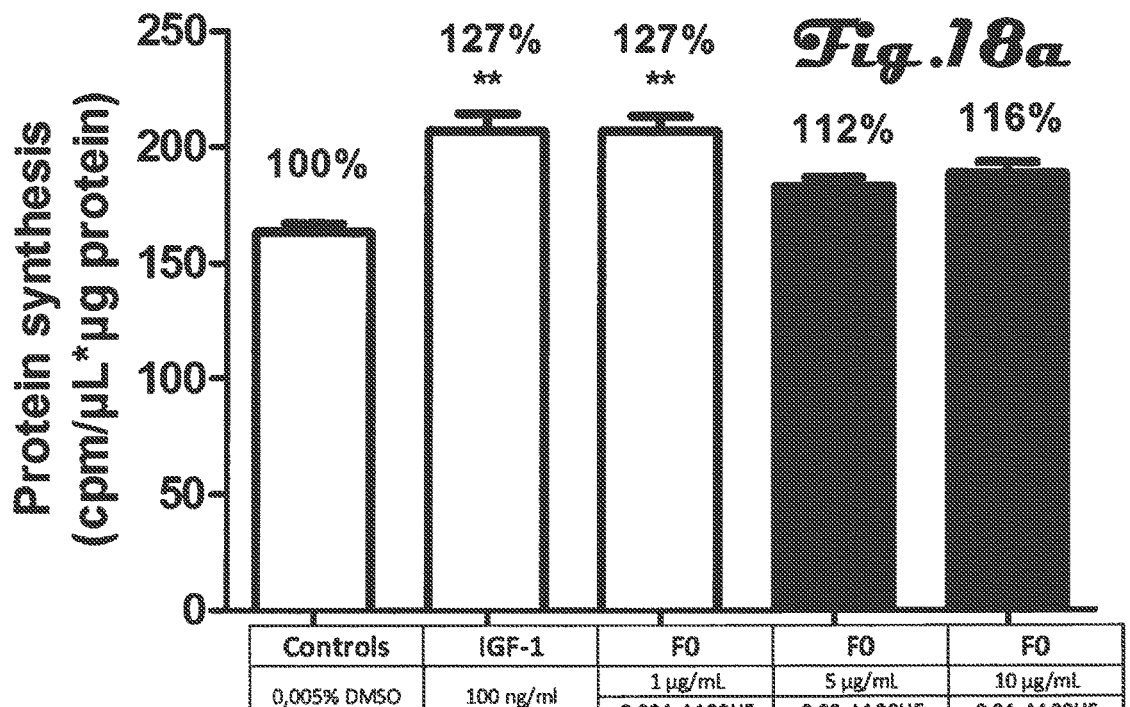
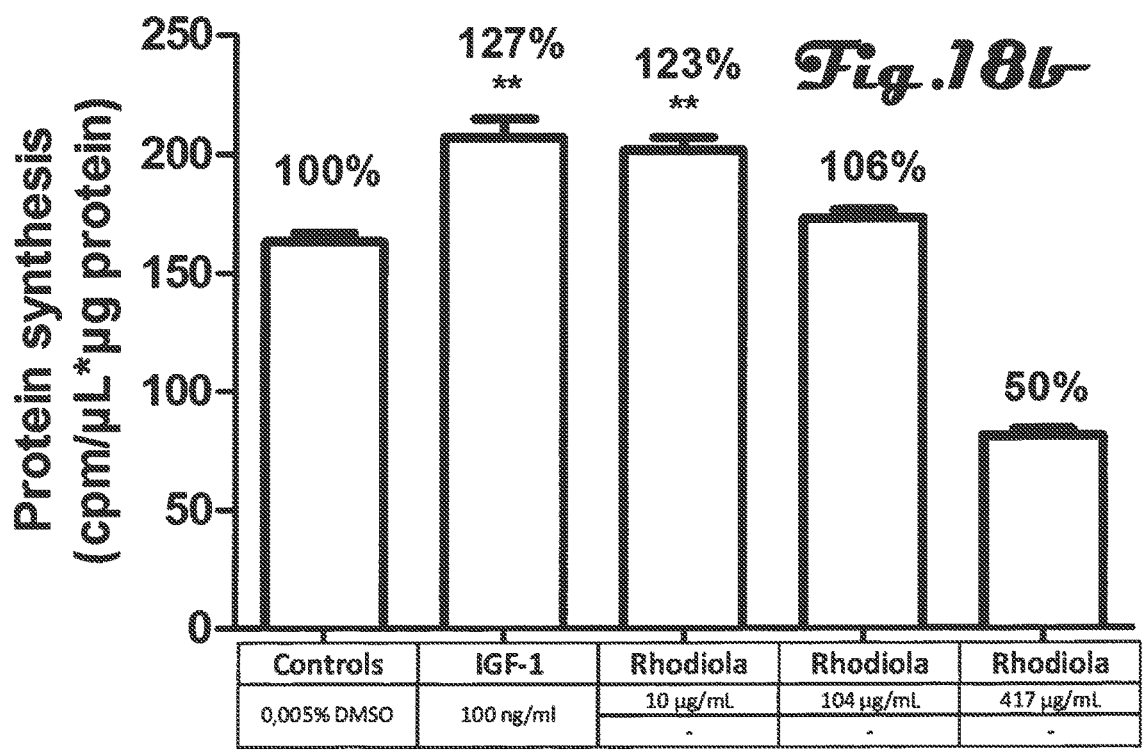

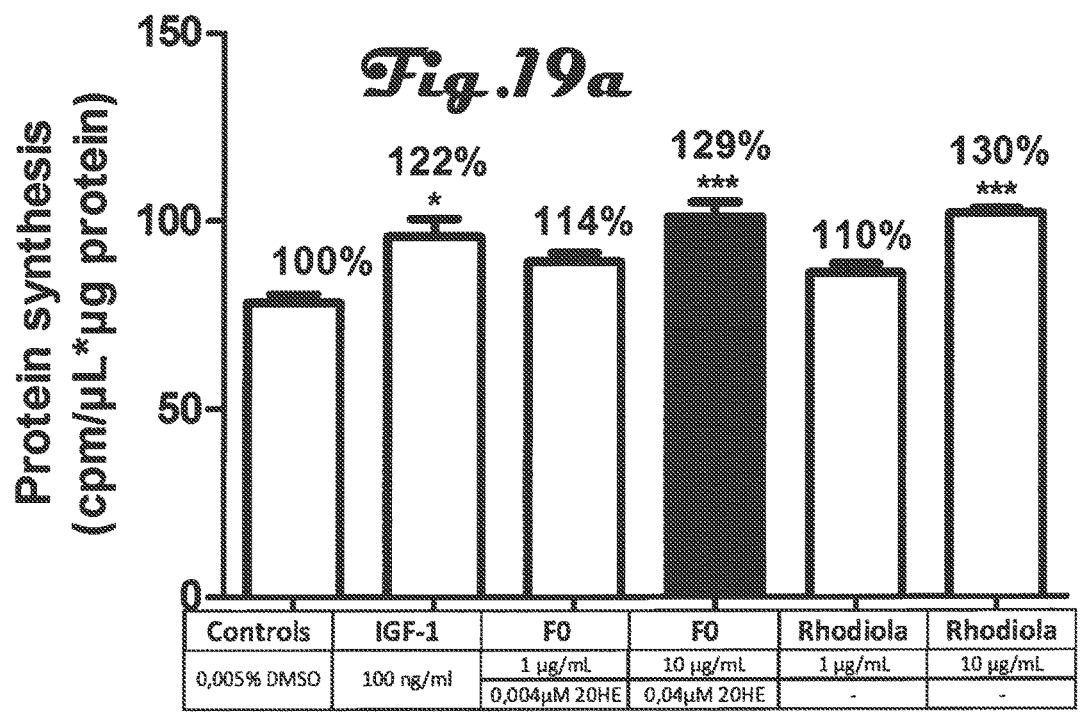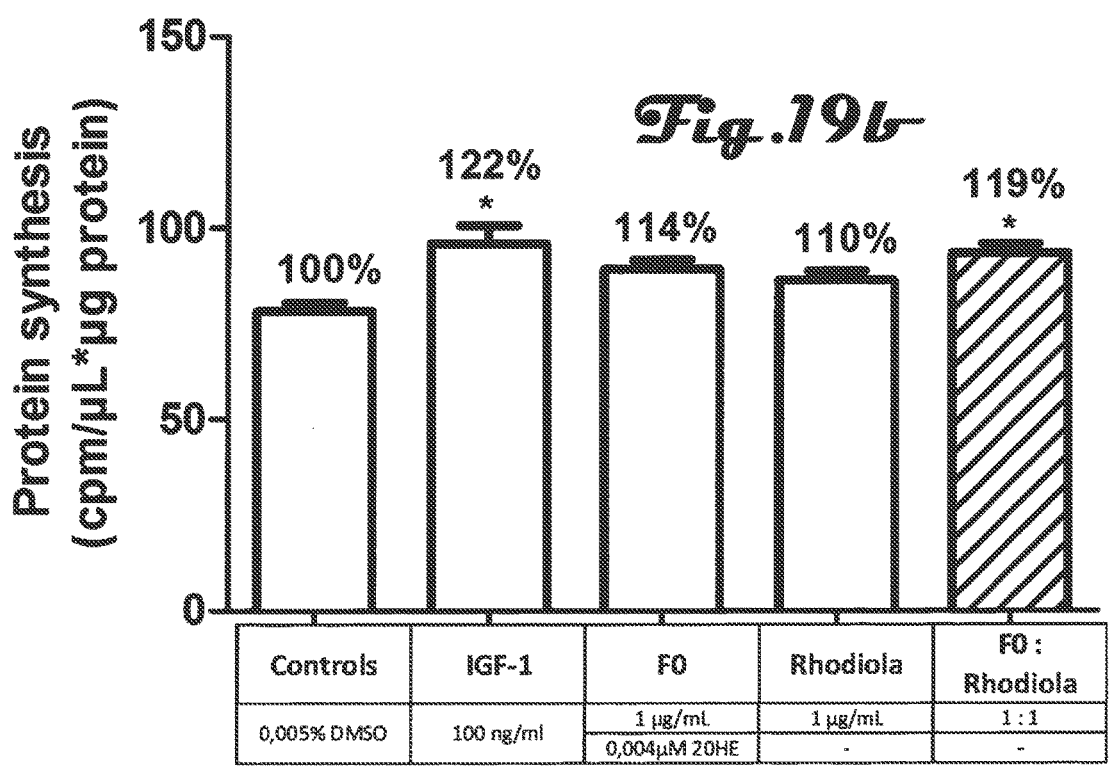

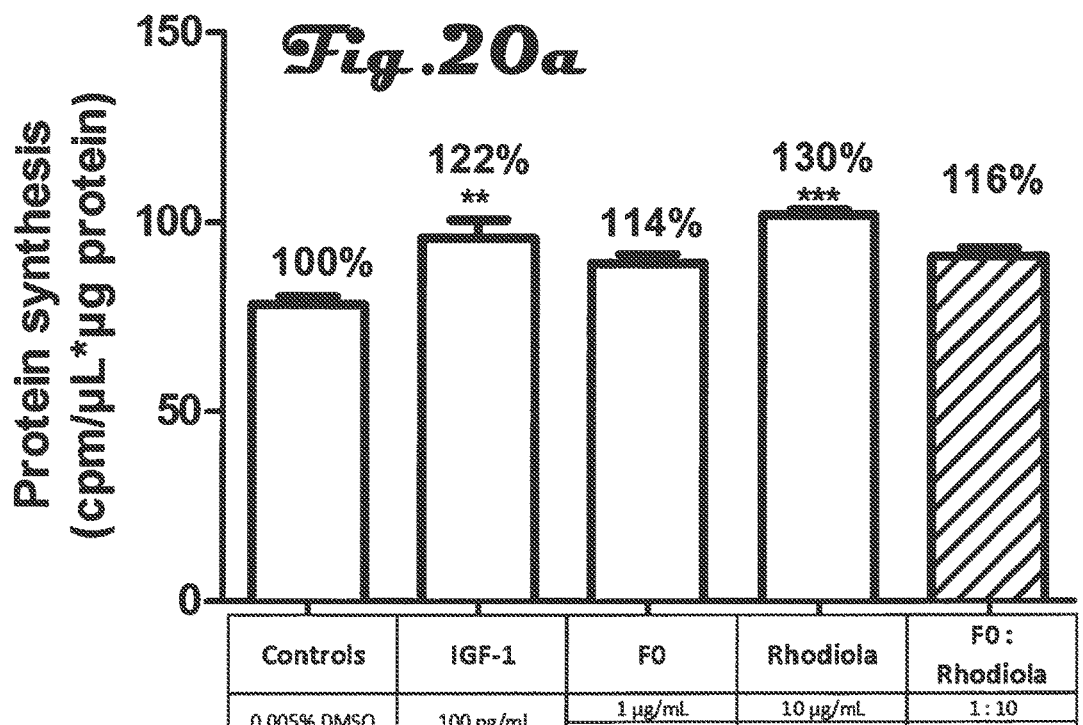
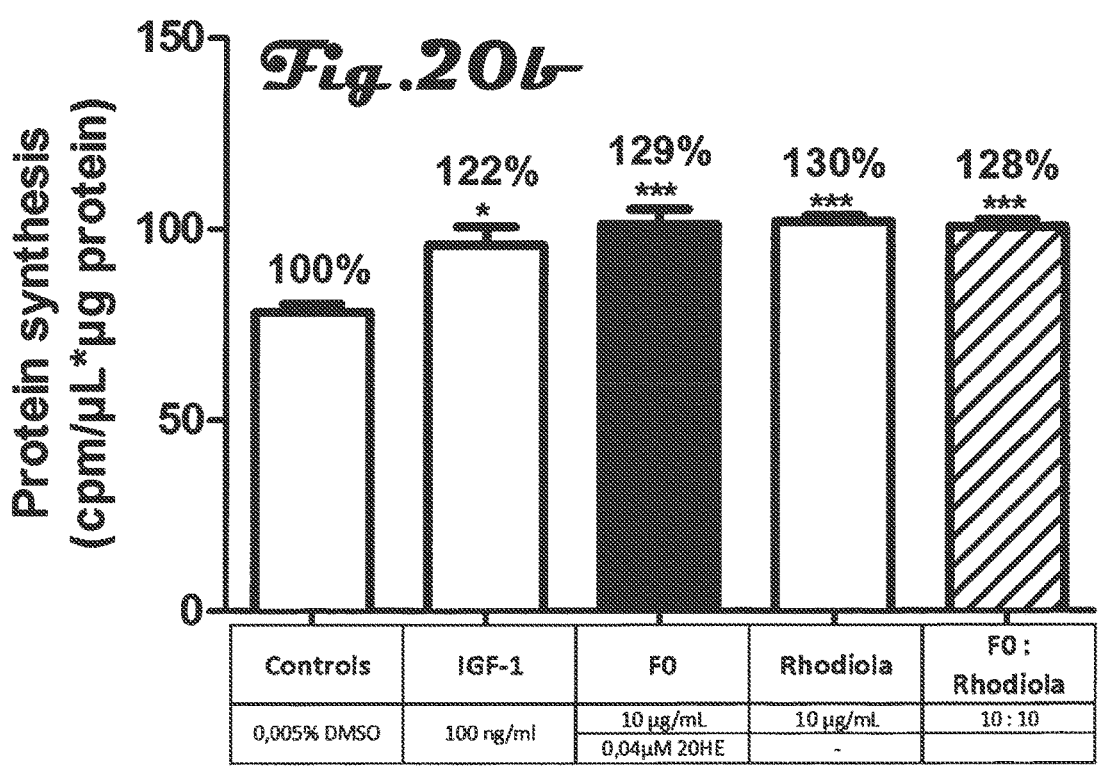

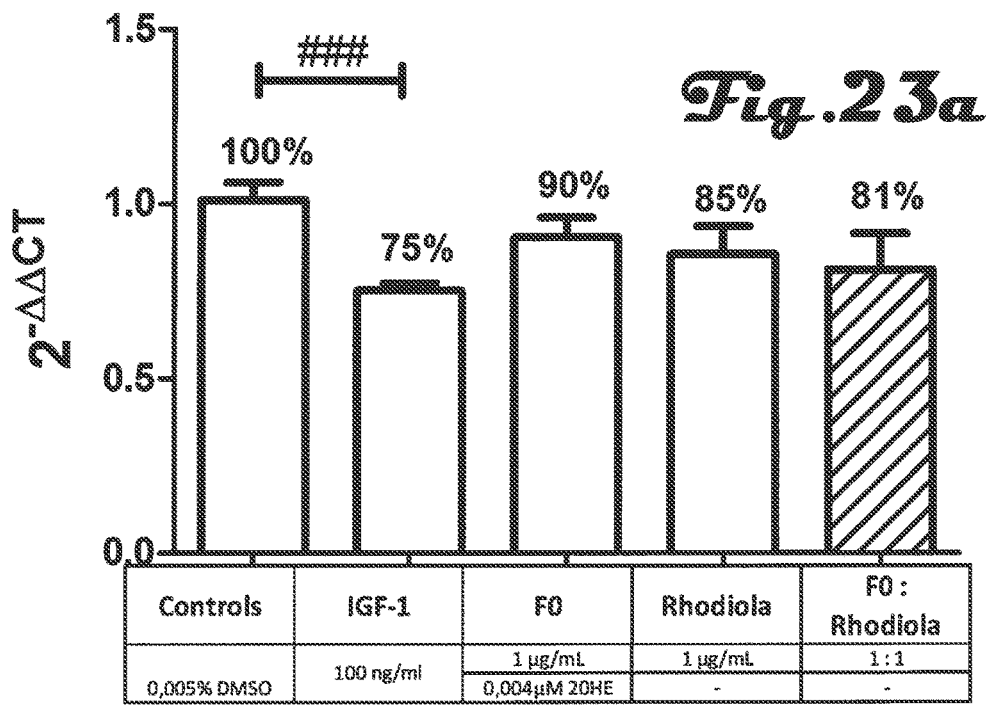
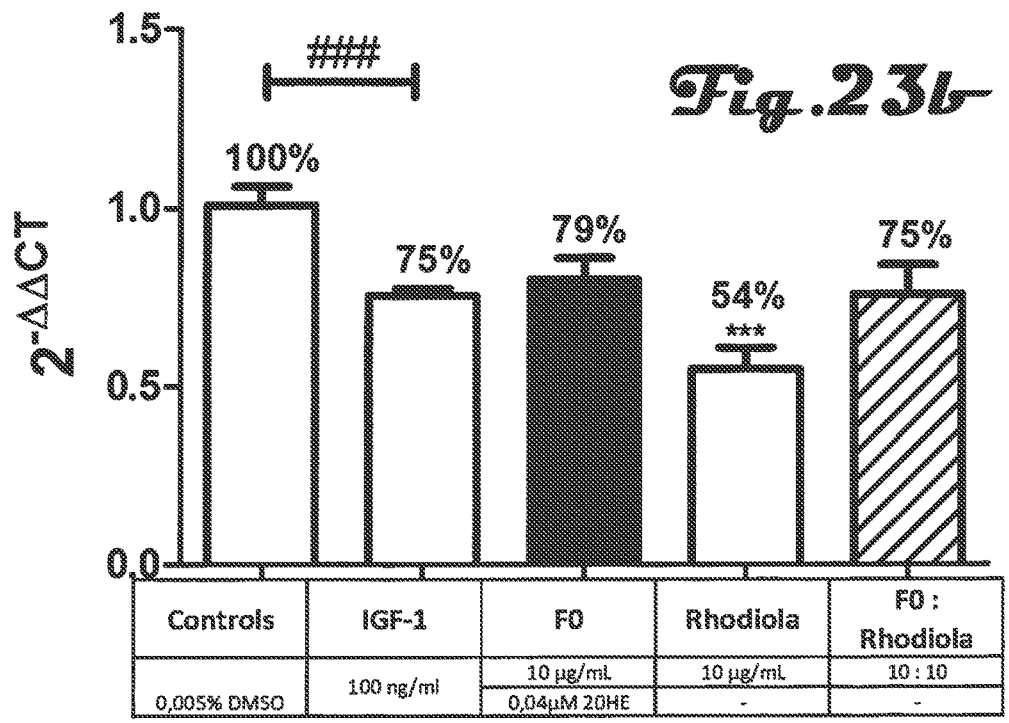

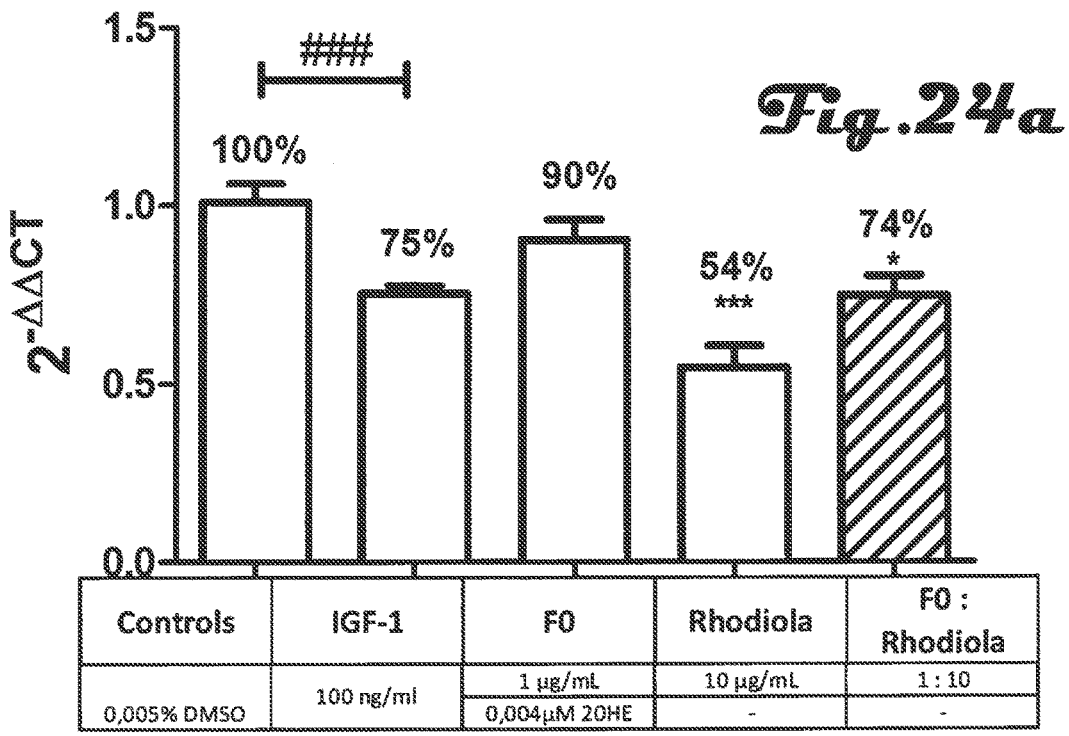
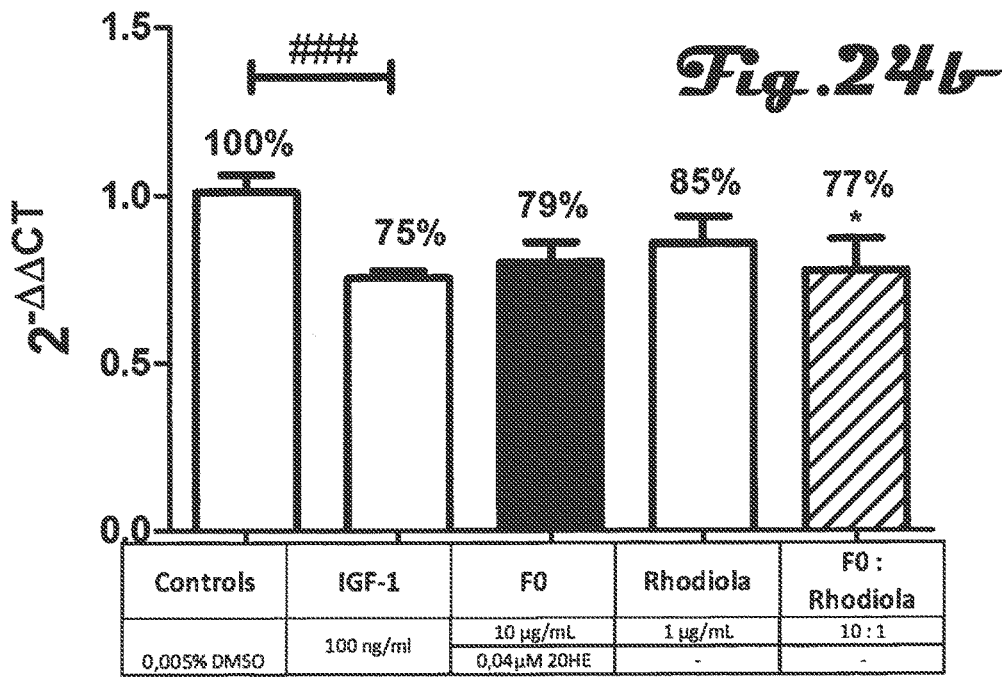

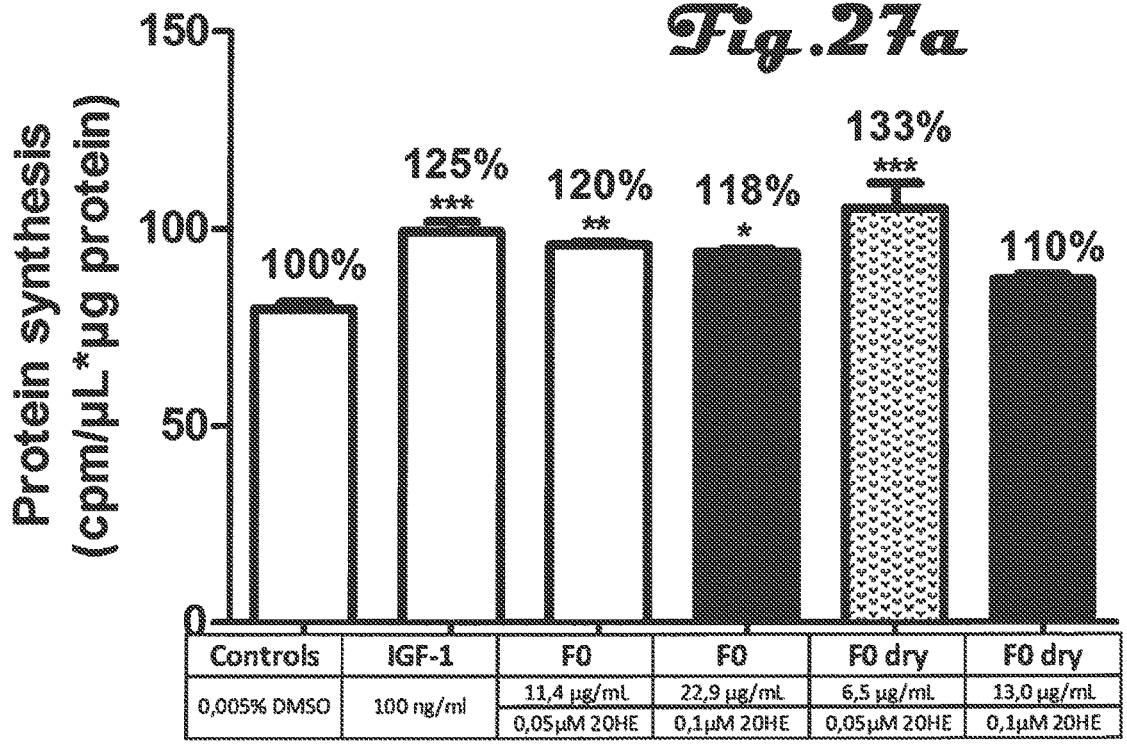
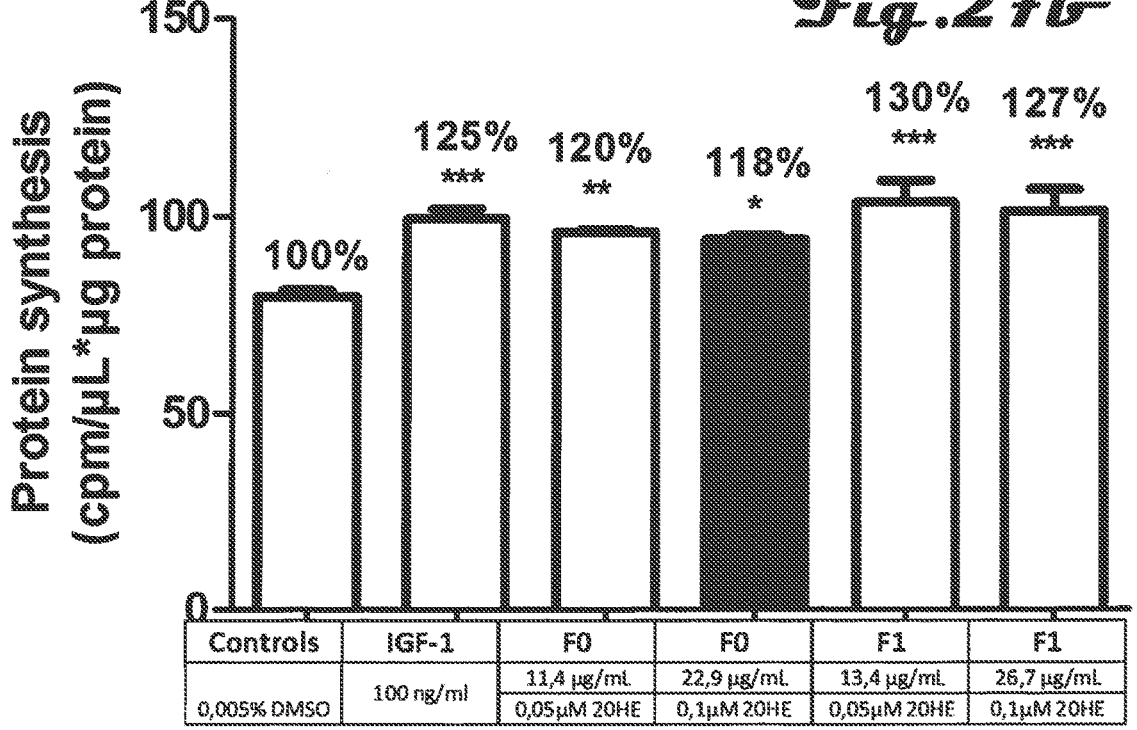

| Fraction | Best stimulation of protein synthesis |
|---|---|
| F1 step 1 | No activation |
| purified F3 step 1 | No activation |
| F0 EtOH 50% step 3 | 120% at 11,4µg/mL |
| purified F5' step 3 | No activation |
| F7 EtOH 70% step 1 | 129% at 3µg/mL |
| purified F5 step 1 | 123% at 300µg/mL |

EDL WEIGHT D44

EDL WEIGHT D44

COMPOSITIONS AND METHODS FOR IMPROVED MUSCLE METABOLISM

FIELD OF THE INVENTION

The present disclosure provides compositions and methods for increasing muscle protein synthesis, reducing muscle proteolysis, increasing muscle mass and/or strength, and improving aerobic/anaerobic sport performance. Useful compositions include, but are not limited to, *Rhaponticum* and *Rhodiola* extracts, and combinations thereof.

SUMMARY OF THE INVENTION

In one aspect, the invention includes a composition including a *Rhaponticum* extract. In some embodiments, the *Rhaponticum* extract comprises at least 0.01%, 0.05%, 0.1%, 0.2%, 0.3%, 0.4%, 0.5%, 0.75%, 1%, 2%, 3%, 4%, 5%, 6%, 7%, 8%, 9%, or 10% ecdysteroids including, for example, about 0.1 to 10% ecdysteroids or about 0.4% to 5% ecdysteroids. In some embodiments the *Rhaponticum* extract composition comprises at least 0.01%, 0.05%, 0.1%, 0.2%, 0.3%, 0.4%, 0.5%, 0.75%, 1%, 2%, 3%, 4%, 5%, 6%, 7%, 8%, 9%, or 10% of 20-hydroxyecdysone including, for example, 0.1% to 5.0% of 20-hydroxyecdysone.

In another aspect, the invention includes a composition including a *Rhodiola* extract. In some embodiments, the *Rhodiola* extract comprises at least 0.5%, 0.75%, 1%, 2%, 3%, 4%, 5%, 6%, 7%, 8%, 9%, or 10% salidrosides including, for example, about 1% to 4%. In some embodiments, the *Rhodiola* extract composition comprises at least 0.1%, 0.2%, 0.3%, 0.4%, 0.5%, 0.75%, 1%, 2%, 3%, 4%, 5%, 6%, 7%, 8%, 9%, or 10%, rosavins including, for example, about 3% to 6% rosavins. In some embodiments, the composition comprises at least 0.1%, 0.2%, 0.3%, 0.4%, 0.5%, 0.75%, 1%, 2%, 3%, 4%, 5%, 6%, 7%, 8%, 9%, or 10%, rosavin including, for example, about 2% to 5% rosavin or 1% to 5% rosavin. In some embodiments, the *Rhodiola* extract composition comprises at least 50%, 55%, 60%, 65%, 70%, 75%, 80%, 85%, 90%, 95% or 99% *Rhodiola* extract including, for example about 50% to 99%, 60%-95%, 70%-95% *Rhodiola* extract.

In one aspect, the invention includes a composition including a *Rhaponticum* extract and a *Rhodiola* extract. In some embodiments, the *Rhaponticum* extract comprises at least 0.01%, 0.05%, 0.1%, 0.2%, 0.3%, 0.4%, 0.5%, 0.75%, 1%, 2%, 3%, 4%, 5%, 6%, 7%, 8%, 9%, or 10% ecdysteroids including, for example, about 0.1 to 10% ecdysteroids or about 0.4% to 5% ecdysteroids. In some embodiments the composition comprises at least 0.01%, 0.05%, 0.1%, 0.2%, 0.3%, 0.4%, 0.5%, 0.75%, 1%, 2%, 3%, 4%, 5%, 6%, 7%, 8%, 9%, or 10% of 20-hydroxyecdysone including, for example, 0.1% to 5.0% of 20-hydroxyecdysone.

In some embodiments, the *Rhodiola* extract comprises at least 0.5%, 0.75%, 1%, 2%, 3%, 4%, 5%, 6%, 7%, 8%, 9%, or 10% salidrosides including, for example, about 1% to 4%. In some embodiments, the composition comprises at least 0.1%, 0.2%, 0.3%, 0.4%, 0.5%, 0.75%, 1%, 2%, 3%, 4%, 5%, 6%, 7%, 8%, 9%, or 10%, rosavins including, for example, about 3% to 6% rosavins. In some embodiments, the composition comprises at least 0.1%, 0.2%, 0.3%, 0.4%, 0.5%, 0.75%, 1%, 2%, 3%, 4%, 5%, 6%, 7%, 8%, 9%, or 10%, rosavin including, for example, about 2% to 5% rosavin. In some embodiments, the composition comprises at least 50%, 55%, 60%, 65%, 70%, 75%, 80%, 85%, 90%, 95% or 99% *Rhodiola* extract including, for example about 50% to 99%, 60%-95%, 70%-95% *Rhodiola* extract.

In another aspect, the invention includes compositions having (i) at least 0.1%, 0.2%, 0.3%, 0.4%, 0.5%, 0.75%, 1%, 2%, 3%, 4%, 5%, 6%, 7%, 8%, 9%, or 10% ecdysteroids including, for example, about 0.1 to 10% ecdysteroids or about 0.4% to 5% ecdysteroids and (ii) at least 0.5%, 0.75%, 1%, 2%, 3%, 4%, 5%, 6%, 7%, 8%, 9%, or 10% salidrosides including, for example, about 1% to 4%. In some embodiments the composition comprises at least 0.1%, 0.2%, 0.3%, 0.4%, 0.5%, 0.75%, 1%, 2%, 3%, 4%, 5%, 6%, 7%, 8%, 9%, or 10% of 20-hydroxyecdysone including, for example, 0.1% to 5.0% of 20-hydroxyecdysone. In some embodiments, the composition comprises at least 0.1%, 0.2%, 0.3%, 0.4%, 0.5%, 0.75%, 1%, 2%, 3%, 4%, 5%, 6%, 7%, 8%, 9%, or 10%, rosavins including, for example, about 3% to 6% rosavins. In some embodiments, the composition comprises at least 0.1%, 0.2%, 0.3%, 0.4%, 0.5%, 0.75%, 1%, 2%, 3%, 4%, 5%, 6%, 7%, 8%, 9%, or 10%, rosavin including, for example, about 2% to 5% rosavin.

In other embodiments, any of the foregoing compositions may be included in a pharmaceutical formulation. The composition may be formulated in any convenient and suitable formulation depending upon the route of intended administration. Suitable formulations for oral administration include, for example, a tablet, pill, capsule, powder, solution, suspension, syrup, or elixir. Optionally, the composition further contains a pharmaceutically-acceptable excipient or carrier, or other pharmaceutically-active or non-active ingredient.

Other aspects of the invention include methods for increasing protein synthesis, increasing muscle strength, and/or reducing protein proteolysis in a subject by administering to the subject any of the compositions or pharmaceutical formulations described above. Further aspects include methods for treating conditions associated with or characterized by muscle atrophy in a subject by administering to the subject any of the compositions or pharmaceutical formulations described above. The composition or formulation may be administered to the subject by any appropriate route of administration. In one embodiment, the composition is orally administered. In some embodiments, the subject is administered a daily dose of at least 1 mg/kg/day, 5 mg/kg/day, 10 mg/kg/day, 20 mg/kg/day, 30 mg/kg/day, 40 mg/kg/day, 50 mg/kg/day, 75 mg/kg/day, 100 mg/kg/day, 200 mg/kg/day, 400 mg/kg/day, 600 mg/kg/day, 800 mg/kg/day, 1000 mg/kg/day, 2000 mg/kg/day, 3000 mg/kg/day, 5000 mg/kg/day or more per day. In one embodiment, the oral formulation is about 30-1000 mg/kg/day. In another embodiment, the oral formulation is about 50-100 mg/kg/day, about 5-50 mg/kg/day, or less than 200 mg/kg/day. In further embodiments, the oral formulation can be about 200-500 mg/day, or about 50-2000 mg/day. The total daily dose may be administered as a unitary dosage or split into multiple dosages administered at different times (e.g., twice, three times, four times, or more per day).

In various embodiments, dosage can be modified based on the type of subject and/or the mass of the subject. For example, in some embodiments a suitable dosage for a human subject can be 50-2000 mg/day or 200-500 mg/day. In some embodiments, a desirable dosage for a human subject or ruminant subject can be 5-50 mg/kg/day or less than 200 mg/kg/day.

In some embodiments, a subject can be treated for conditions including sarcopenia, sarcopenic obesity, a cancer, multiple sclerosis, muscular dystrophy, a bone fracture requiring immobilization (e.g., splint or cast), amyotrophic laterals sclerosis (ALS), a peripheral neuropathy, stroke, or cachexia. Subjects can have or be diagnosed as having such a condition and such a condition can be idiopathic or secondary to another condition. In some embodiments, the subject is a mammal including, for example, a human or an animal (e.g., canine, feline, ovine, bovine, ruminant, etc.). Accordingly, in various embodiments, the compositions described herein can be used in food, feed products, or nutritional supplements for humans or animals.

BRIEF DESCRIPTION OF THE DRAWINGS

FIG. 1a is a graph of total phenolics identified in the extract of Example 11;

FIG. 1b is a graph of total organic acids identified in the extract of Example 11;

FIG. 2 is a graph of total free carbohydrates identified in the extract of Example 11;

FIGS. 3a, 3b, 4a, 4b, 5a, 5b, 6a, 6b, 7a, and 7b are bar graphs depicting determination of S6K1 phosphorylation on threonine 389 in C2C12 myotubes after incubation with 5 different preparations of *Rhaponticum* extract at three concentrations and with low and high amino acid;

FIGS. 8a, 8b, 9a, 9b, 10a, 10b, 11a, 11b, 12a, 12b are bar graphs depicting determination of Akt phosphorylation on threonine 308 in C2C12 myotubes after incubation with 5 different preparations of *Rhaponticum* extract at three concentrations and with low and high amino acid;

FIGS. 13a, 13b, 14a, 14b, 15a, 15b, 16a, 16b, 17a, 17b are bar graphs depicting determination of protein synthesis in C2C12 myotubes after incubation with 5 different preparations of *Rhaponticum* extract at three concentrations and with low and high amino acid;

FIGS. 18a and 18b are bar graphs depicting determination of protein synthesis in C2C12 myotubes after incubation with *Rhaponticum* F0 and *Rhodiola* extracts at three concentrations;

FIGS. 19a, 19b, 20a, 20b and 21 are bar graphs depicting determination of protein synthesis in C2C12 myotubes after incubation with *Rhaponticum* F0 and *Rhodiola* extracts alone or in combination at two concentrations;

FIGS. 23a, 23b, 24a, and 24b are bar graphs that depict the effect of co-incubation of *Rhaponticum* F0 and *Rhodiola* extracts on myostatin gene expression in C2C12 myotubes;

FIGS. 27a, 27b and 28 are bar graphs that depict determination of protein synthesis in C2C12 myotubes after incubation with different preparation of *Rhaponticum* extracts at two concentrations;

Figure 6A:
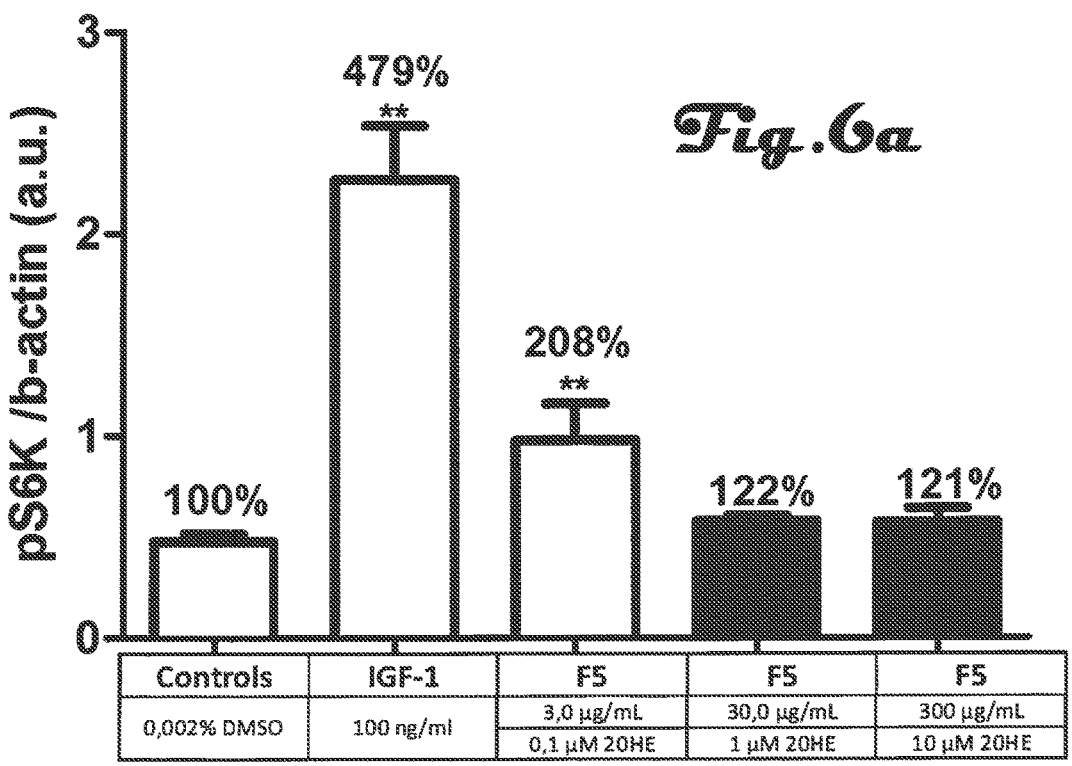
Figure 6B:
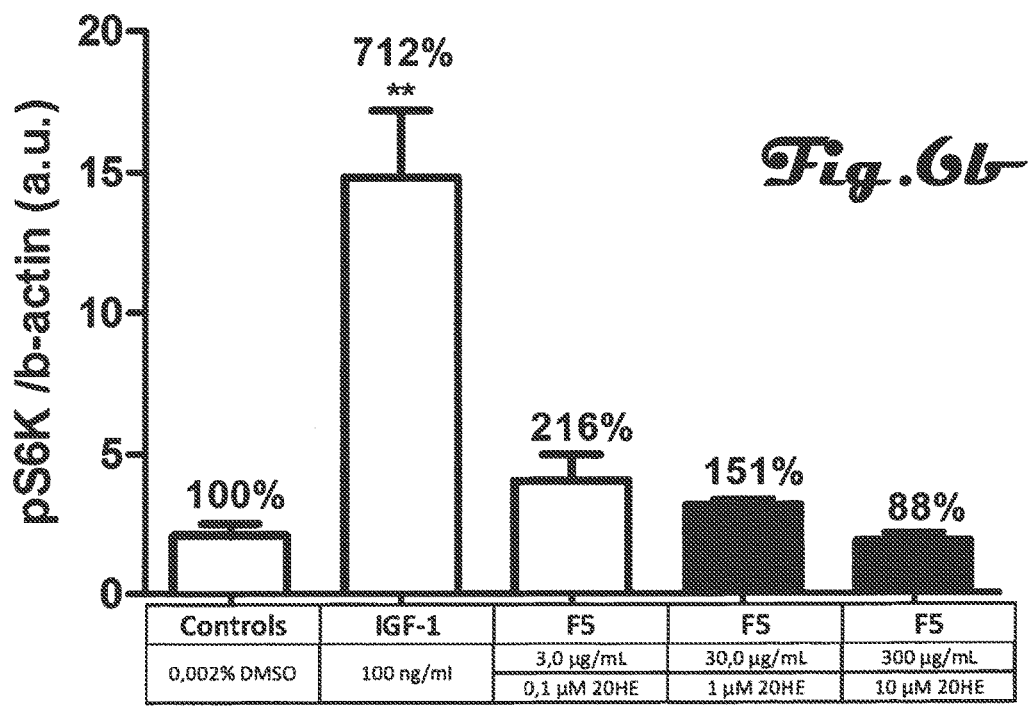
Figure 8A:
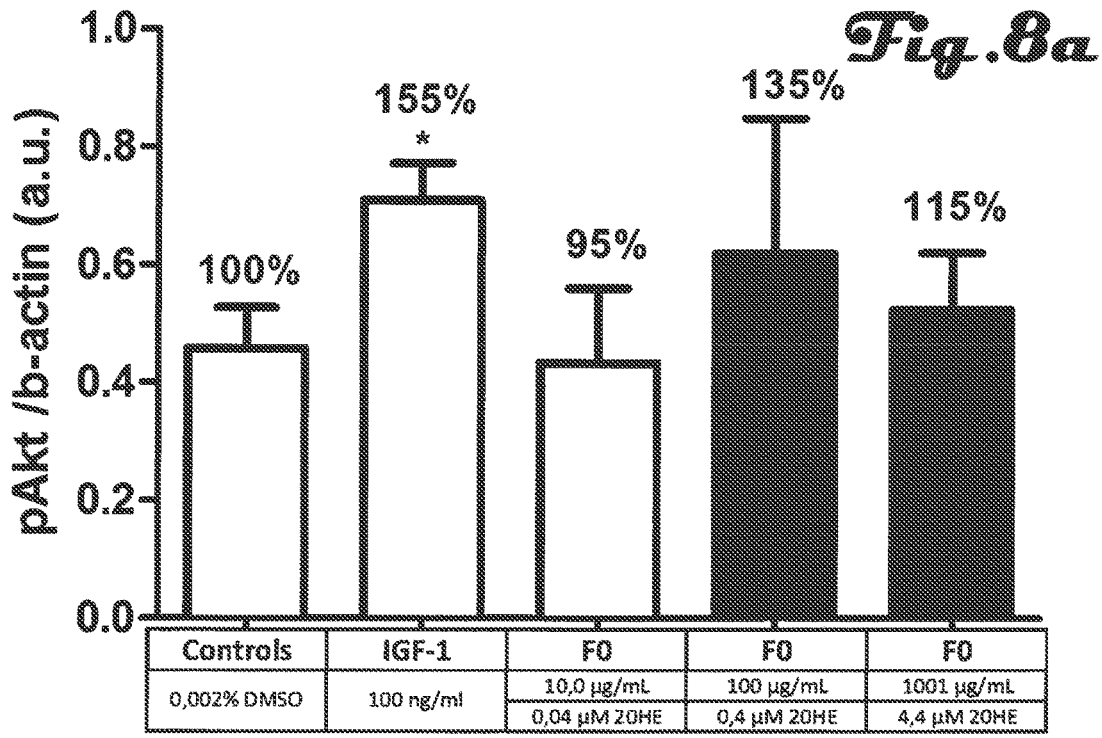
Figure 8B:
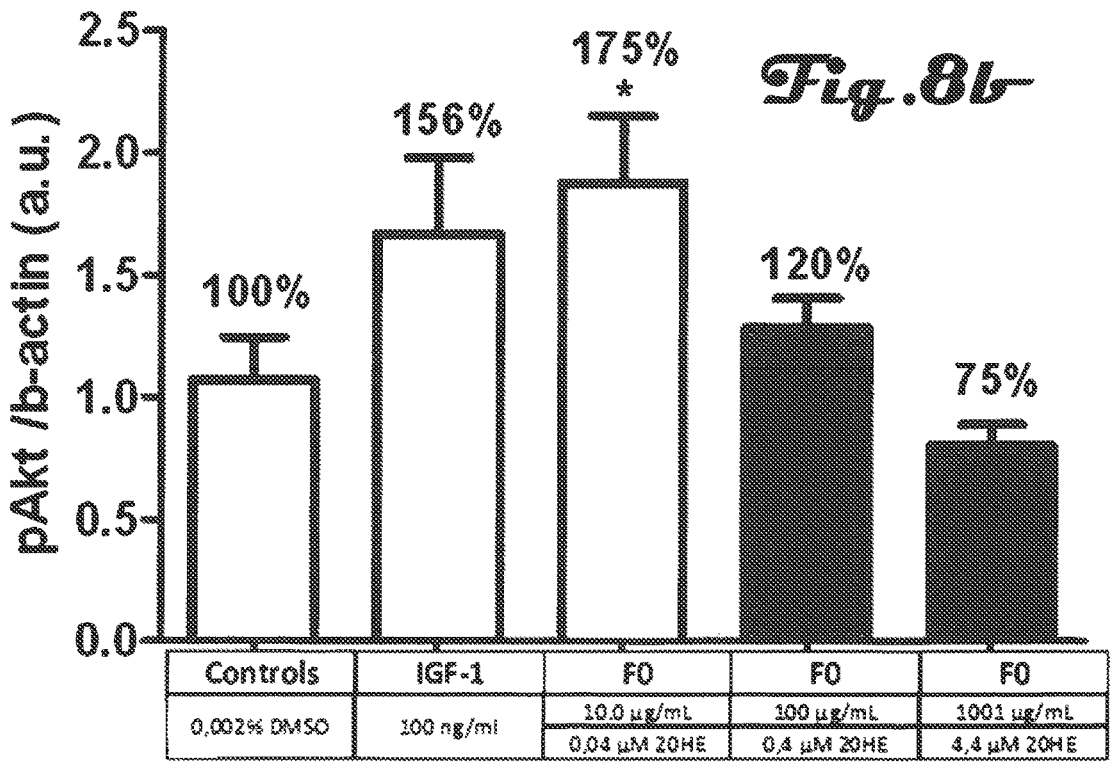
Figure 10A:
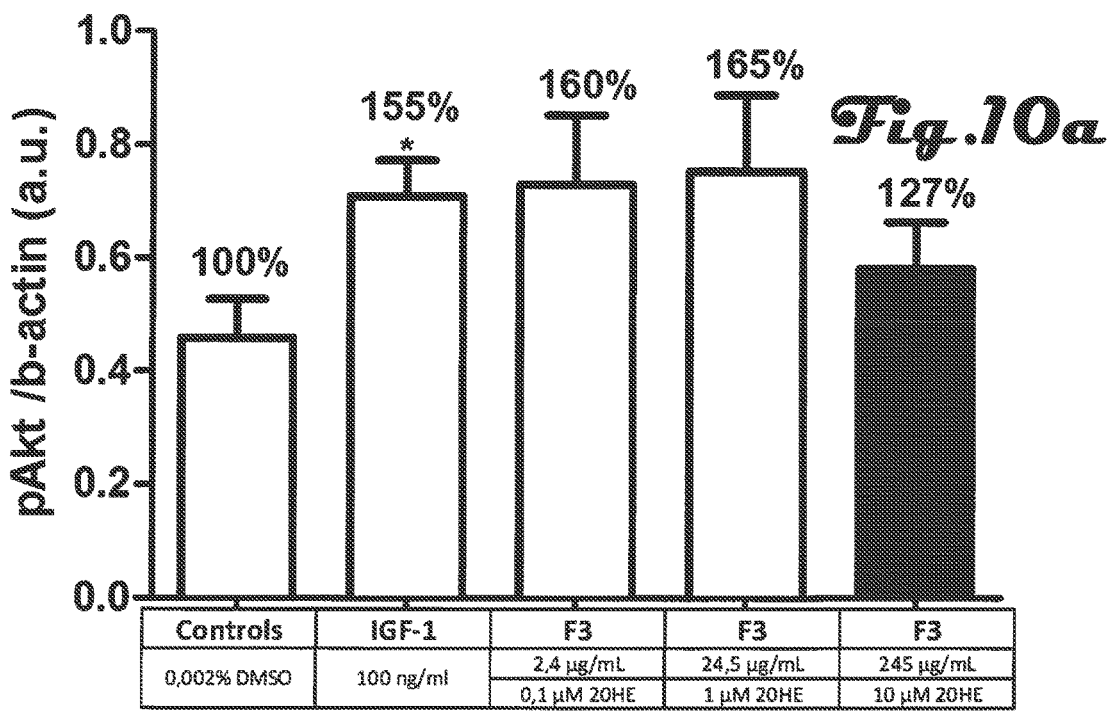
Figure 10B:
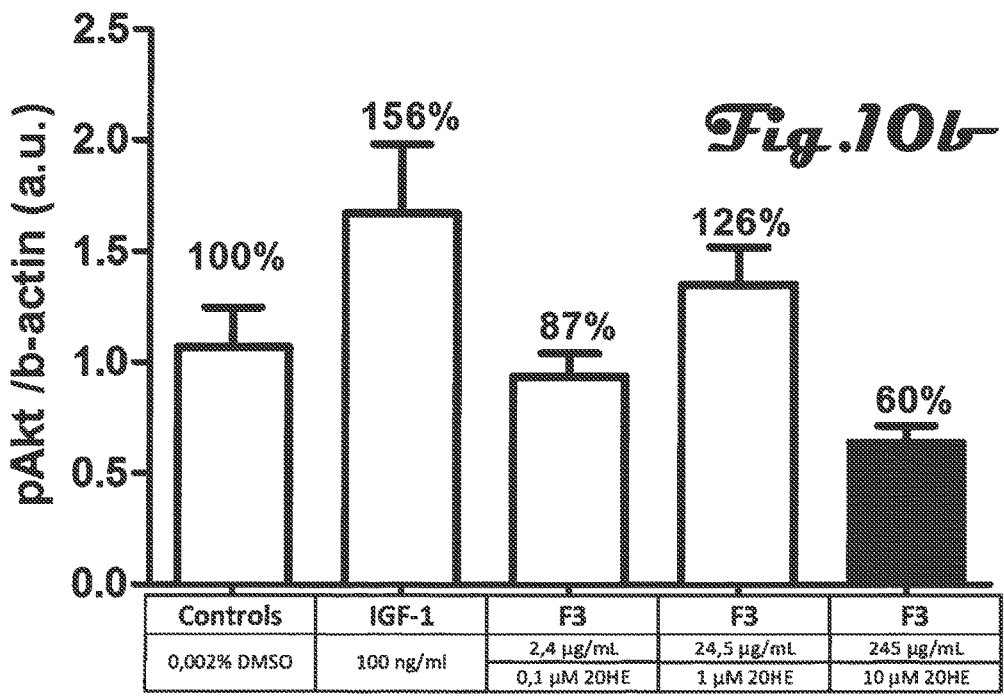
Figure 11A:
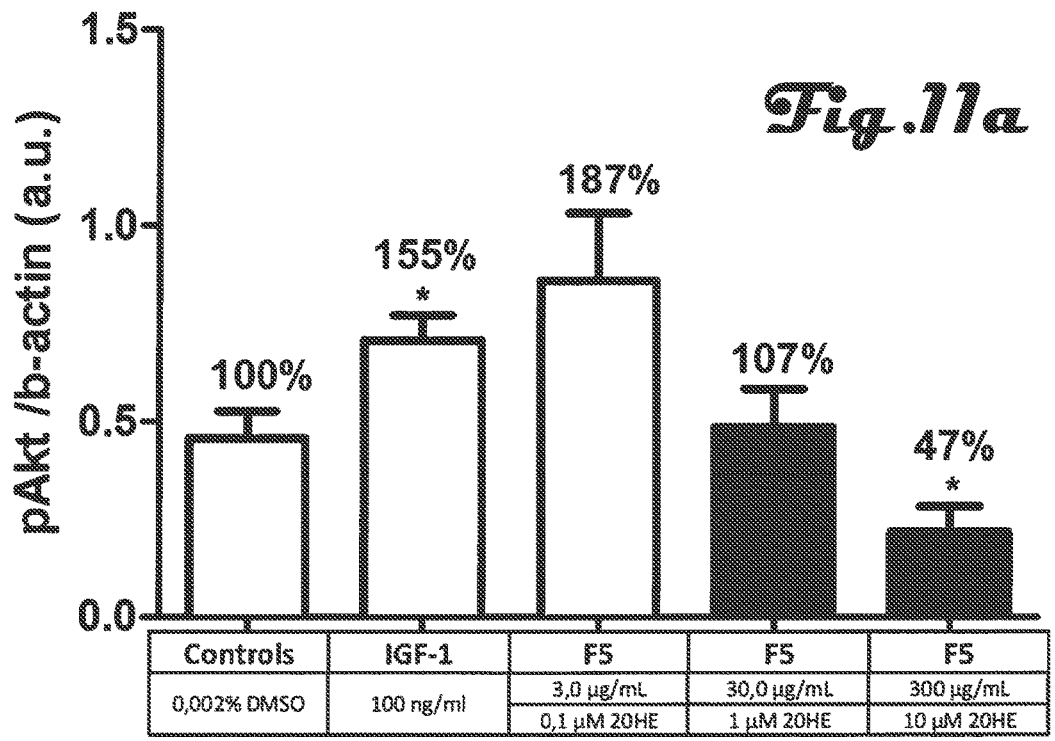
Figure 11B:
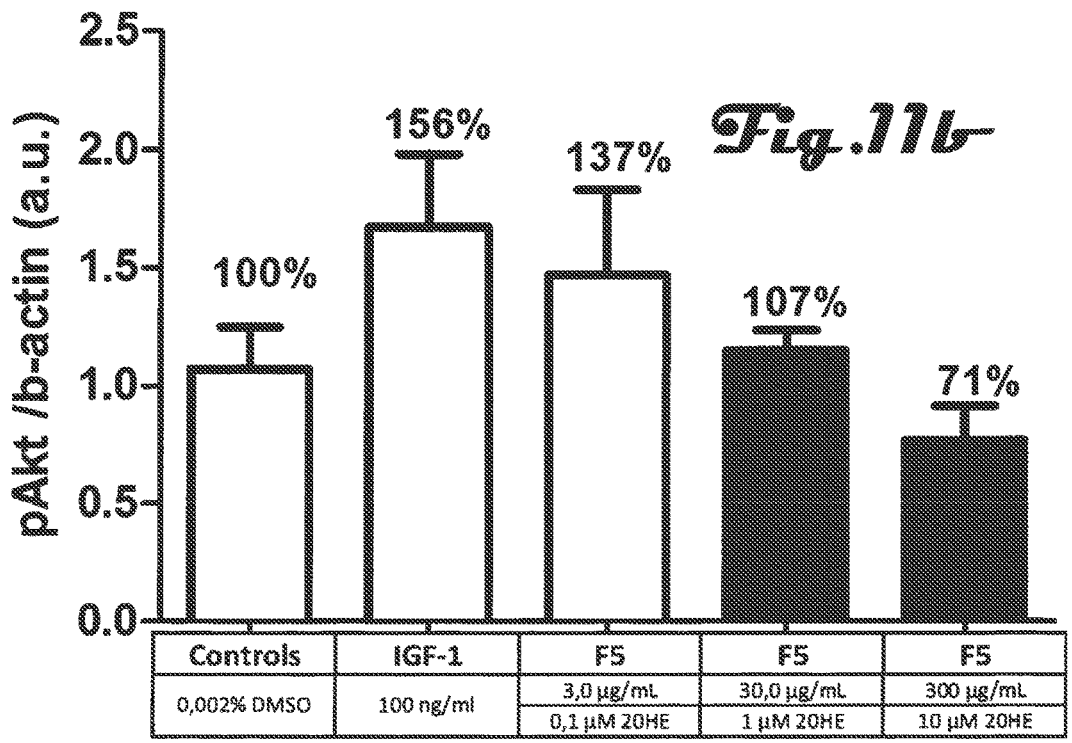
Figure 13A:
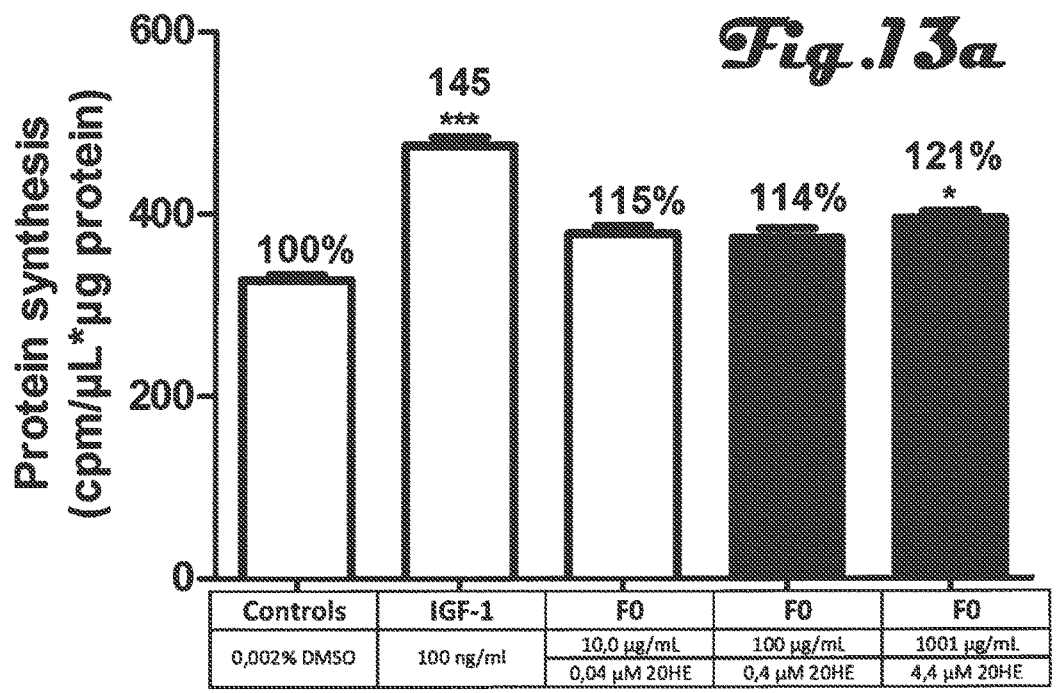
Figure 13B:
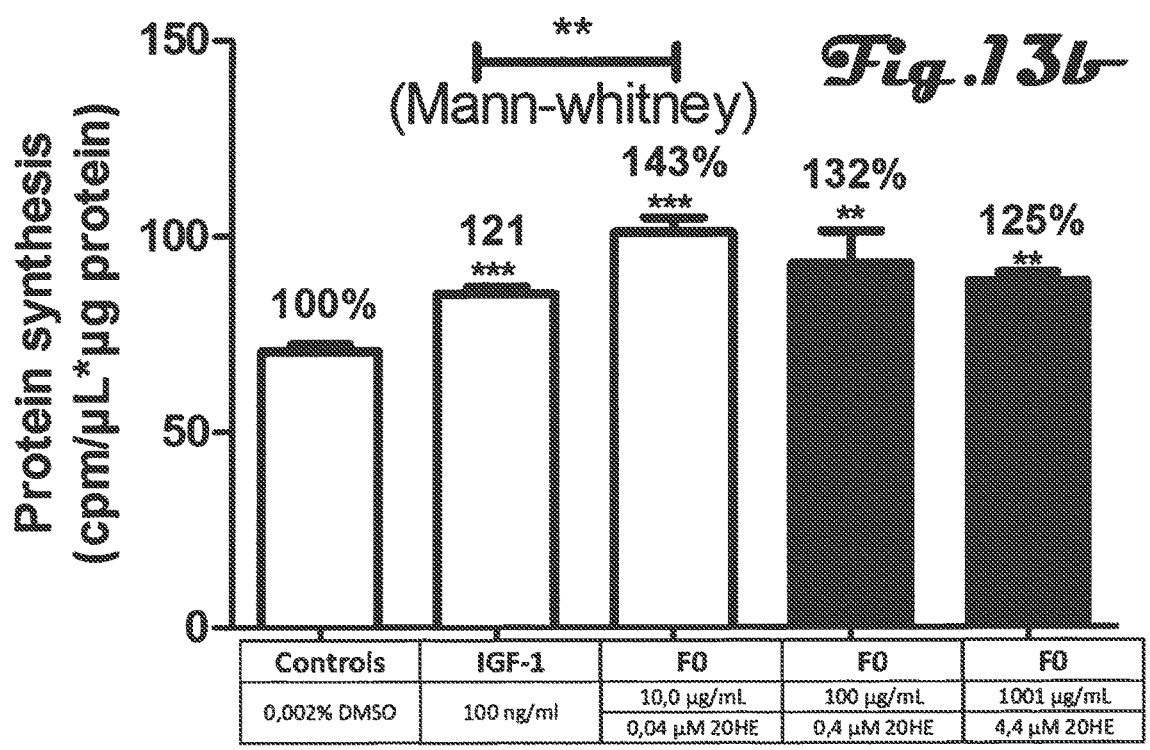
Figure 21:
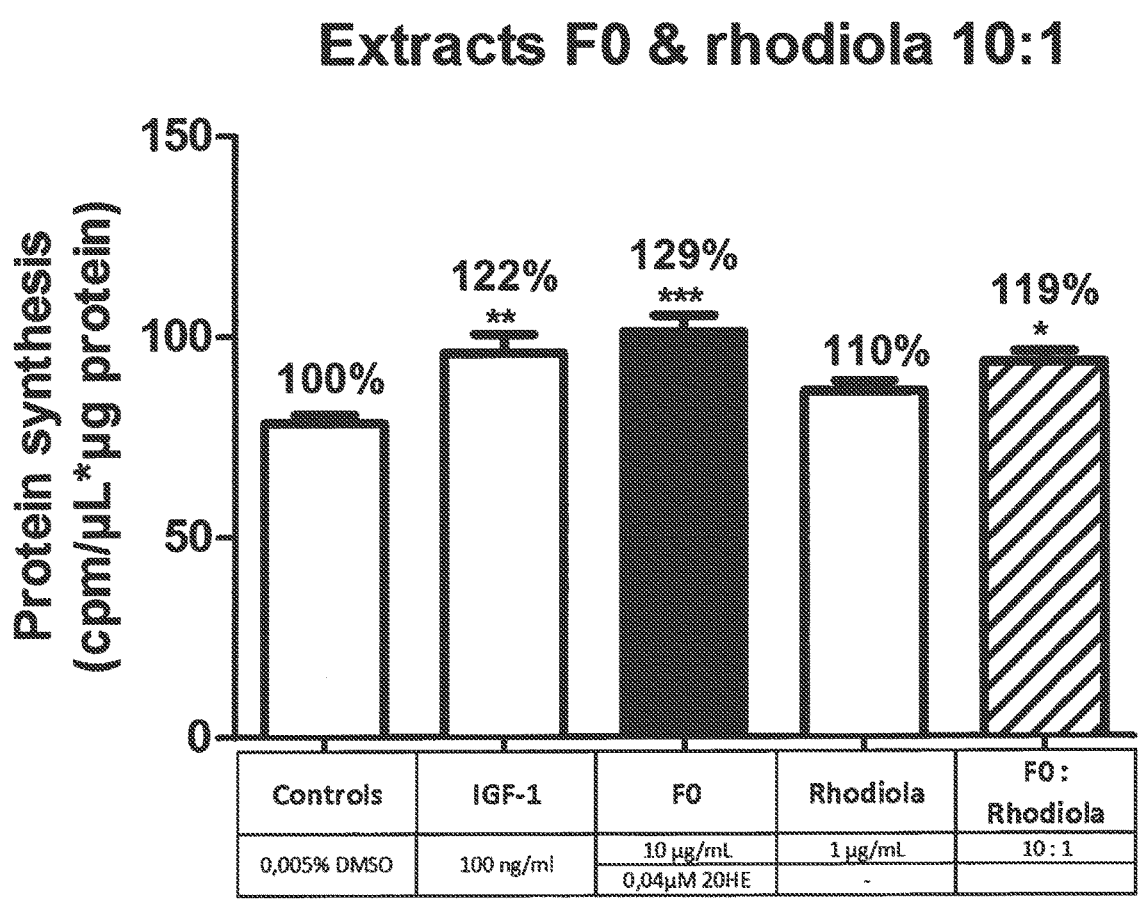

It also should be noted that the figures are only intended to facilitate the description of the preferred embodiments. The figures do not illustrate every aspect of the described embodiments and do not limit the scope of the present disclosure.

DETAILED DESCRIPTION

The present disclosure provides example embodiments of novel compositions for pharmaceutical or nutraceutical use in a mammal, preferably in a human, to increase protein synthesis, muscle mass, and/or muscle strength. The working examples demonstrate that combination of *Rhodiola* and *Rhaponticum* extracts, and related synthetic compositions, can increase protein synthesis, reduce proteolysis (inhibit the expression of Atrogin-1 and myostatin), increase muscle mass and muscle strength. In various embodiments, compositions are provided, comprising an extract of *Rhodiola rosea* and/or an extract of *Rhaponticum* carthamoides. Synthetic compositions (i.e., compositions in which one or more ingredients are not derived from plant extracts) are also disclosed.

*Rhaponticum* Extracts

The extract of *Rhaponticum* may be derived from any *Rhaponticum* species including (but not limited to) *Rhaponticum acaule* (L.) DC., *Rhaponticum aulieatense* Iljin, *Rhaponticum australe* (Gaudich.), *Rhaponticum berardioides* (Batt.), *Rhaponticum canariense* DC., *Rhaponticum carthamoides* (Willd.), *Rhaponticum coniferum* (L.) Greuter, *Rhaponticum cossonianum* (Ball) Greuter, *Rhaponticum cynaroides* Less., *Rhaponticum exaltatum* (Willk.) Greuter, *Rhaponticum fontqueri*, *Rhaponticoides hajastana* (Tzvelev) M. V. Agab. & Greuter, *Rhaponticum heleniifolium* Godr. & Gren., *Rhaponticoides iconiensis* (Hub.-Mor.) M. V. Agab. & Greuter, *Rhaponticum insigne* (Boiss.)

Wagenitz, *Rhaponticum integrifolium* C. Winkl., *Rhaponticum karatavicum* Iljin, *Rhaponticum longifolium* (Hoffmanns. & Link) Dittrich, *Rhaponticum lyratum* C. Winkl. ex Iljin, *Rhaponticum namanganicum* Iljin, *Rhaponticum nanum* Lipsky, *Rhaponticum nitidum* Fisch, *Rhaponticum pulchrum* Fisch. & C. A. Mey. *Rhaponticum repens* (L.) Hidalgo, *Rhaponticum scariosum* Lam., *Rhaponticum serratuloides* (Georgi) Bobrov, *Rhaponticum uniflorum* (L.) DC. In some embodiments, the herbal extract of *Rhaponticum* is made from a plant selected from the family of Asteraceae, the genus *Rhaponticum* and more specifically the specie *Rhaponticum Carthamoides*.

An extract may be prepared from any part(s) of the *Rhaponticum* plant, however, the root is particularly useful. *Rhaponticum* root may be extracted with a solvent from the group of ethanol, methanol, water, ethanol in water, ethyl acetate, acetone, hexane, or any other conventional extraction solvent, preferably ethanol in water or water, more preferably ethanol in water 10 to 90% v/v, and even more preferably ethanol in water 30 to 70% (v/v). In one embodiment, extraction consists in mixing grinded *Rhaponticum* root with solvent at a solvent:plant ratio of between 1:1 to 30:1 and the plant may undergo a single, or alternatively, double extraction (or more extractions) process. Extraction duration is preferably >1 hr, most preferably 1.5 hrs. In a preferred embodiment, *Rhaponticum* root is mixed with ethanol in water (50% v/v) at a ratio of 10:1 and undergoes 3 successive extractions. After extraction, the combined mixture may be filtered and/or centrifuged and the supernatant concentrated to 30 to 70% DM, most preferably 50% DM, and finally dried to solid form, with <10% moisture, such as in the form of a powder. One of skill in the art will recognize multiple processes of preparing plant extracts and that can be used for the present disclosure, in addition to the particular processes disclosed herein.

Components of interest in *Rhaponticum* are ecdysteroids, in particular 20-hydroxyecdysone ($(2\beta,3\beta,5\beta,22R)$-2,3,14,20,22,25-Hexahydroxycholest-7-en-6-one). This compound can be used as a reference for determination of the quality of the preparations, although it may not be the sole compound bringing effects and a mixture of compounds is likely to render the extract more effective than 20HE alone (Timofee et al, Voldov et al).

In some embodiments, the extract of *Rhaponticum* comprises at least 0.01% total ecdysteroids, about 0.05% to 99%, 98%, 97%, 96%, 95%, 90%, 80%, 70%, 60%, 50%, 40%, 30%, 20%, or 10% total ecdysteroids based on the total weight of the extract (w/w), more preferably at least about 0.1 to 10% total ecdysteroids, most preferably 0.4% to 5% total ecdysteroids based on the total weight of the extract (w/w).

In some embodiments, the extract of *Rhaponticum* comprises at least 0.01% 20-hydroxyecdysone (20HE) based on the total weight of the extract (w/w), about 0.05% to 99%, 98%, 97%, 96%, 95%, 90%, 80%, 70%, 60%, 50%, 40%, 30%, 20%, or 10% 20HE, more preferably at least about 0.1% to 5.0% 20HE based on the total weight of the extract (w/w).

In addition, the extract of *Rhaponticum* may also comprise ecdysteroids other than ecdysterone, such as by way of a non-limiting example, the following ecdysteroids: polypodine B, Makisterone A, 2-Deoxyecdysterone, Integristerone A, Integristerone B, Taxisterone, Ajugasterone C, α-ecdysone, Lesterone, Rapisterone D, Inokosterone, Rapisterone, 20-hydroxyecdysone 2,3;20,22-diacetonide; 20-hydroxyecdysone 2,3-monoacetonide; 20-hydroxyecdysone 20,22-monoacetonide; 22-oxo-20-hydroxyecdysone, 24(28)-dehydromakisterone A; (24z)-29-hydroxy-24(28)-dehydromakisterone C; carthamosterone; rubrosterone, dihydrorubrosterone; posterone, isovitexirone, leuzeasterone, makisterone C, polypodine B 20,22-acetonide; rapisterone B, rapisterone C, rapisterone D 20-acetate, 24(24')(z)-dehydroamarasterone B, polypodine B-22-benzoate; carthamosterone A, carthamosterone B; Amarasterone A; carthamoleusterone; 24(28)-dehydroamarasterone B, 22-deoxy-28-hydroxymakisterone C; 3-epi-20-hydroxyecdysone; 24-epi-makisterone A, 14-epi-ponasterone A 22-glucoside; 5-α-20-hydroxyecdysone; 20-hydroxyecdysone 2-acetate, 20-hydroxyecdysone 3-acetate; 1β-hydroxymakisterone C; 26-hydroxymakisterone C; 15-hydroxyponasterone A; inokosterone 20,22-acetonide, turkestone.

The extract of *Rhaponticum* may also comprise the following ecdysteroids: abutasterone25-acetoxy-20-hydroxyecdysone 3-o-; beta;-d-glucopyranoside; acetylpinnasterol; achyranthesterone; ajugacetalsterone a; ajugacetalsterone b; ajugalide e; ajugasterone b; ajugasterone b; ajugasterone c 3; 22-diacetonide; ajugasterone c 22-ethylidene; acetal; ajugasterone c 22-monoacetonide; ajugasterone d; amarasterone a; amarasterone b; asteraster b; atrotosterone a; atrotosterone b; atrotosterone c; blechnoside a; blechnoside b; bombycosterol; bombycoster 3-phosphate; brahuisterone; calonysterone; calvaster a; calvaster b; canescenstterone; capitasterone; carpesterol; castasterone; cheilanthone a; cheilanthone b; coronatasterone; cyanosterone a; cyasterone; cyasterone 3-acetate; cyasterone 22-acetate; cyasterone 3-monoacetonide; cyathisterone; dacryhainansterone; decumbesterone a; dehydroajugalactone; dehydroajugalactone; dehydroamarasterone b; dehydrocyasterone 2-glucoside; 3-dehydroecdysone; 2-dehydro-3-epi-20-hydroxyecdysone; and/or 22-dehydro-12-hydroxycyasterone, dehydro-20-hydroxyecdysone; 3-dehydro-20-hydroxyecdysone; dehydro-242-hydroxymakisterone c dehydro-12-hydroxy-29-nor-cyasterone; dehydro-12-hydroxy-29-nor-sengosterone; dehydro-12-hydroxy-sengosterone; (28)-dehydromakisterone a; 2-dehydropoststerone; 24-dehydroprecyasterone; 2-deoxycastasterone; 22-deoxy-21-dihydroxyecdysone; 22-deoxy-26-dihydroxyecdysone; 2-deoxy-26-dihydroxyecdysone; 3-deoxy-1(alpha) 20-dihydroxyecdysone; 2-deoxy-20-dihydroxyecdysone 2-deoxypolypodine b; 2-deoxyecdysone; deoxyecdysone; 2-deoxyecdysone 3-acetate; 2-deoxyecdysone 22-acetate; 2-deoxyecdysone 22-adenosine-monophosphate; 2-deoxyecdysone 22-benzoate; 2-deoxyecdysone 3-4-(1-(beta)-d-glucopyranosyl)-ferulate; 2-deoxyecdysone 22-(beta)-d-glucoside; 25-deoxyecdysone 22-o-(beta)-d-glucopyranoside; 2-deoxyecdysone 22-phosphate; 2-deoxyecdysone 25-rhamnoside; (5(alpha))-2-deoxy-21-hydroxyecdysone; 2-deoxy-20-hydroxyecdysone; 22-deoxy-26-hydroxyecdysone; 14-deoxy-20-hydroxyecdysone; 2-deoxy-21-hydroxyecdysone; 2-deoxy-20-hydroxyecdysone 25-acetate; 2-deoxy-20-hydroxyecdysone 22-acetate; (5(alpha))-2-deoxy-20-hydroxyecdysone 3-acetate; 2-deoxy-20-hydroxyecdysone 3-acetate; 2-deoxy-20-hydroxyecdysone 22-benzoate; and/or 2-deoxy-20-hydroxyecdysone 3-crotonate.

The extract of *Rhaponticum* may comprise polyphenols (in particular gallic acid and polymer as procyanidin B1).

The extract of *Rhaponticum* may comprise phenolic compounds (in particular cynarin and chlorogenic acid).

The extract of *Rhaponticum* may comprise flavonoids such as patuletin, 6-hydroxykaempferol-7-glukoside, quercetagitrin, quercetin, quercetagetin, luteolin, kaempferol, isorhamnetin, quercetin-3-methyl ether, quercetin-5-o-β-D- galactoside, isorhamnetin 5-o-α-L-rhamnoside, quercetagetin-7-o-β-glucopyranoside; apigenin, ariodictyol, eriodictyol-7-β-glucopyranoside, hesperin, chrysanthemin, Cyanin.

The extract of *Rhaponticum* may comprise lignans (carthamogenin, carthamoside, trachelogenin, tracheloside).

The extract of *Rhaponticum* may comprise tannins (ellagic acid).

The extract of *Rhaponticum* may comprise serotonine phenylpropanoids.

The extract of *Rhaponticum* may comprise polyacetylenes.

The extract of *Rhaponticum* may comprise sesquiterpene lactones.

The extract of *Rhaponticum* may comprise triterpenoid glycosides (rhaponticosides A to H).

The extract of *Rhaponticum* may comprise triterpenoids (parkeol, parkeyl acetate).

Rhodiola Extracts

The present disclosure also includes an extract of *Rhodiola*, a high altitude growing plant having about 200 species, including *R. rosea* and *R. crenulata* (Kelly, Altern. Med. Rev. 6:293-302, (2001); Ming et al., Phytother. Res. 19:740-743, (2005)). *Rhodiola rosea* is an adaptogen which helps the body adapt to and resist a variety of physical, chemical, and environmental stresses.

The extract of *Rhodiola* used in the compositions of the present disclosure can be made from any plant in the group of *Rhodiola rosea, Rhodiola crenulata, Rhodiola sachalinensis Rhodiola sacra, Rhodiola algida, Rhodiola dumulosa, Rhodiola kirilowii, Rhodiola henryi, Rhodiola yunannensis*. An extract can be made from any portion of the *Rhodiola* plant, however, extracts prepared from the root and rhizome are particularly useful.

*Rhodiola* species can contain phenylpropanoids such as rosavin ((2E)-3-phenylprop-2-en-1-yl 6-O-α-L-arabinopyranosyl-α-D-glucopyranoside), rosin ((2R,3S,4S,5R,6R)-2-(hydroxymethyl)-6-[(E)-3-phenylprop-2-enoxy]oxane-3,4,5-triol) and rosarin ((2E)-3-phenyl-2-propenyl6-O—.alpha.-L-arabinofuranosyl-(9CI); [(E)-3-Phenyl-2-propenyl]6-O-α-L-arabinofuranosyl-β-D-glucopyranoside; [(E)-3-Phenyl-2-propenyl]6-O-(α-L-arabinofuranosyl)-β-D-glucopyranoside). *Rhodiola* species can also contain phenylethanol derivatives such as salidroside/rhodioloside (2-(4-hydroxyphenyl)ethyl β-D-glucopyranoside) and tyrosol (4-(2-Hydroxyethyl)phenol). *Rhodiola* species can further contain flavanoids (e.g., rodiolin, rodionin, rodiosin, acetylrodalgin and tricin); monoterpernes (e.g., rosiridol and rosaridin); triterpenes (e.g., daucosterol and beta-sitosterol); phenolic acids (e.g., chlorogenic, hydroxycinnamic and gallic acids); tannins, essential amino acids and minerals. Active ingredients like p-tryosol, salidroside, rosavin, pyridrde, rhodiosin and rhodionin are found in most of the *Rhodiola* species, but vary in the amounts. One bioactive ingredient of interest in *Rhodiola rosea* is salidroside. Rosavins (e.g., the sum of rosarin, rosin and rosavin) are another bioactive constituent identified from the plant. Salidroside and/or rosavins can be used as references for determination of the quality of the preparations.

In some embodiments, the extract of *Rhodiola* comprises at least about 0.10% to 90%, 80%, 70%, 60%, 50%, 40%, 30%, 20%, or 10% salidrosides based on the total dry weight of the extract; more preferably at least about 1% to 4% salidrosides. In some embodiments, the extract of *Rhodiola* comprises at least about 0.10% to about 90%, 80%, 70%, 60%, 50%, 40%, 30%, 20%, or 10% rosavin more preferably at least about 2.0 to 5% rosavin based on the total weight of the extract. In some embodiments, the extract of *Rhodiola* comprises at least about 0.10% to 90%, 80%, 70%, 60%, 50%, 40%, 30%, 20%, or 10% rosavins (e.g., the sum of rosarin, rosavin and rosin), more preferably at least about 3 to 6% or 1 to 6% rosavins based on the total weight of the herbal extract.

Extract Combinations

In some embodiments, the extract of *Rhodiola* comprises about 1 to 99%, 98%, 97%, 96%, 95%, 90%, 80%, 70%, 60%, 50%, 40%, 30%, 20%, or 10% w/w (e.g. about 1%, about 10%, about 20%, about 30%, about 40%, about 50%, about 60%, about 70%, about 80%, about 90% or about 99% w/w) based on the total weight of the composition and the extract of *Rhaponticum* comprises about 99% to 1% w/w (e.g. about 1%, about 10%, about 20%, about 30%, about 40%, about 50%, about 60%, about 70%, about 80%, or about 90% or about 99% w/w) based on the total weight of the composition.

The extract of *Rhodiola* may comprise about 50-99% w/w and the extract of *Rhaponticum* comprises about 1-50% w/w of the total weight of the composition. The extract of *Rhodiola* may comprise about 1-50% w/w and the extract of *Rhaponticum* comprises about 50-99% w/w of the total weight of the composition. Various suitable example proportions of *Rhodiola* and *Rhaponticum* are as follows:

The extract of *Rhodiola* is about 90% w/w and the extract of *Rhaponticum* is about 10% w/w of the total weight of the composition. The extract of *Rhodiola* comprises about 10% w/w and the extract of *Rhaponticum* comprises about 90% w/w of the total weight of the composition. The extract of *Rhodiola* is about 60% w/w and the extract of *Rhaponticum* is about 40% w/w of the total weight of the composition. The extract of *Rhodiola* comprises about 40% w/w and the extract of *Rhaponticum* comprises about 60% w/w of the total weight of the composition The extract of *Rhodiola* is about 50% w/w and the extract of *Rhaponticum* is about 50% w/w of the total weight of the composition. In some embodiments, the mass ratio of *Rhaponticum* and *Rhodiola* can be about between 60:40 and 80:20. In one embodiment, the mass ratio of *Rhaponticum* and *Rhodiola* can be about 75:25.

In one embodiment, compositions are provided which comprise an extract of *Rhodiola rosea* (root) at about 50% w/w and an extract of *Rhaponticum carthamoides* (root) at about 50% w/w based on the total weight of the extract components/of the composition. The extract of *Rhodiola* contains 1-4% salidrosides, 2-5% rosavin and 3-6% rosavins and the extract of *Rhaponticum* contains 0.37% 20HE and 0.78% total ecdysterones. In some embodiments, the composition can comprise about 0.1% to 10% ecdysterones or about 0.5% to 3% ecdysterones.

Any suitable combination of proportions of the herbal extracts of *Rhodiola rosea* and *Rhaponticum carthamoides* are envisioned to be encompassed by the compositions disclosed herein. The percentages provided herein refer to the w/w ratio of the dry weight of the extract portion on the total weight of the composition.

Pharmaceutical Formulations

As described herein, various species of plants, herbs or portions thereof may be selected as part of compositions and methods for treating disease and promoting improved muscle metabolism. Extracts of such species may be prepared in various suitable ways. In one embodiment, an extract of plants, herbs or portions thereof may be achieved via water and/or alcohol, or both, and then drying to a fine powder. In another embodiment, extraction may be performed via super-critical $CO_2$ extraction.

Compositions of the present disclosure may be, for example, in the form of solid, liquid, or aerosol formulations comprising at least the two extracts in any proportions (one or more of the extracts) as disclosed herein. Compositions of the disclosure may further comprise other components, for example but not limited to, vitamins, pharmaceuticals or excipients added to a formulation at an amount of 0.1 to 99%, 98%, 97%, 96%, 95%, 90%, 80%, 70%, 60%, 50%, 40%, 30%, 20%, or 10% w/w of the final product and the ratios of the extracts may therefore vary accordingly. Such compositions can be manufactured in various formulations, which are administered to a mammal to promote muscle growth and muscle strength.

In one embodiment, the inventive composition is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers.

Liquids for administration may be solutions or suspensions. In one example, the composition of the invention of provided as a dry powder. The subject dissolves or suspends the powder in a beverage of choice (e.g., water, soft drink, fruit juice, etc.) and then consumes that beverage. Alternatively, the inventive compositions are provided in liquid form. In the case of tablets, molded substances, or capsules, the dosage form should be adaptable to uneven dosing. Units having different dose levels can be prepackaged, for example in blister packs, and labeled for time of ingestion. Intervals can be BID, TID, QID or more frequent. In the case of capsules, one or more delayed action pellets can be included with long acting beads. Undoubtedly there are other alternative ways to formulate. As an example, long acting microparticles and suitable amounts of one or more amounts of particles with more delayed action microparticles may be mixed and encapsulated. Matrix substrates can be used to form 2, 3, or 4 multilayered tablets or press coated tablets. Press coated tablets can have delayed action cores. Differently formulated multilayered and press coated tablets, which may include coated and uncoated tablets packaged to specify time of use, can be used. Long acting and delayed action microparticles can likewise be suspended in parenteral fluids to provide uneven dosing.

In some embodiments, an extract such as drying and powdering of such a selected species may be prepared. In further embodiments, an extract may be concentrated before drying, which may be desirable to reduce bulk of the extract. Such concentrations may reduce the bulk of the extract while preserving the full-spectrum of characteristics and levels of marker compounds of the native plant, herb, or portion thereof.

In further embodiments, a low-temperature water processing technique may be used. Such a process may be desirable because it may capture a large portion of supporting constituents like polysaccharides, flavonoids, terpene and valuable volatiles, oils and resins (part of which are typically only captured by alcohol or hexane, both of which leave unwanted traces). The extracted plant material may then be concentrated, and the concentrated liquid may be dried using, e.g. an ultra high speed spray dryer that produces a fine powder, or the like. In some embodiments, concentration of the herbal extract to be dried to a powder may reduce the bulk of the herbal powder without substantially changing the composition of the plant's constituent parts. Such a method may be desirable to reduce unwanted chemical traces that may be introduced into the herbal material, and a more pure, full-spectrum herbal powder may therefore be obtained. For example, concentrations ratios from 10-to-1 to 20-to-1 may be obtained, which may significantly reduce the bulk of the material and provide convenient dosing in capsules.

"Pharmaceutically acceptable carrier" is a substance that may be added to the active ingredients to help formulate or stabilize the preparation and causes no significant adverse toxicological effects to the patient. Examples of such carriers are well known to those skilled in the art and include water, sugars such as maltose or sucrose, albumin, salts such as sodium chloride, etc. Other carriers are described for example in Remington's Pharmaceutical Sciences by E. W. Martin. Such compositions will contain a therapeutically effective amount of *Rhodiola* and *Rhaponticum* extracts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. The composition is preferably formulated for oral ingestion. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In some cases, it will include isotonic agents, for example, sugars, polyalcohols such as mannitol, sorbitol, or sodium chloride in the composition.

As used herein, "carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecule weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and PLURONIC.

Pharmaceutically acceptable carriers also include natural and non-natural carriers such as maltodextrin, gum arabic (E414), silicon dioxide (E551), dextrine de tapioca, dextrines, gum acacia, and the like.

The invention also includes synthetic formulations having the same active ingredients, in the same proportions, as listed above. These ingredients may be purified or synthesized and be included in the compositions and formulations without the inclusion of any other naturally-occurring plant material that is normally present in an extract.

Methods for Use

The *Rhodiola* extract may be used to increase protein synthesis and decrease myostatin and/or atrogin gene expression in skeletal muscle cells. The *Rhaponticum* extract may be used to increase protein synthesis, increase phosphorylation of the Akt pathway members, increase S6K1 phosphorylation, and/or reduce myostatin and/or atrogin gene expression in skeletal muscle cells.

In a further embodiment, the combination of *Rhodiola* and *Rhaponticum* extracts may be administered in amounts that enhance their functions compared to that of each one when administered alone.

In yet another aspect, a method for improving muscle mass and muscle strength in a mammal is provided, comprising administering to the mammal an effective amount of the composition described herein. The mammal is preferably a human, more preferably an athlete. In a further aspect of the disclosure, a method for promoting aerobic and anaerobic sport/physical performance in a mammal is provided, comprising administering to the mammal an effective amount of the composition disclosed herein. In yet another aspect, a method for treating conditions associated with or characterized by muscle atrophy in a mammal is provided, comprising administering to the mammal an effective amount of the composition described herein.

In some embodiments, the composition is orally administered to a mammal, preferably a human, at a daily dose of about 1-5000 mg/day, preferably at about 30-1000 mg/day, more preferably about 50-1000 mg/day, and even more preferably about 100-600 mg/day or 200-500 mg/day. Lower doses of about 0.5 mg/day or a dose higher than 5000 mg/day may be provided. In some embodiments, multiple daily doses of 10, 50, 100, 200, 300, 400, 500, 600, 700, 800 or more mg per dose are provided. mg/kg/day Dosing intervals are conventionally QD (once a day), BID (twice a day), TID (three times a day), QID (four times a day) or more frequent including 5, 6, 7, 8, 9, 10, or more doses per day. Time of administration may be based on half-life, formulation of the dosage form being utilized, systemic reactivity, convenience, whether self administered or regimented, and whether the substance is therapeutic, nutritional, steroidal, or anti-infective.

Unless a composition is control-released, or has a long half-life permitting QD administration, the time interval between ingestion of doses may be uneven. For example, if a substance is ingested upon arising and when retiring, the intervals are probably 16 and 8 hours. If taken upon arising, mid-day, and when retiring, intervals may be 5, 11 and 8 hours. If taken evenly spaced during awake hours, intervals might be 5.33, 5.33, 5.33 and 8 hours. In such cases, rational dosing should be uneven to be consistent with uneven time intervals.

Neutraceuticals and certain drugs, and steroids, antibiotics and like substances may best be taken on a full stomach. Such daytime intervals may be uneven and time between last daytime dose and next morning dose different.

For the prevention or treatment of disease or promotion of improved bodily function, the appropriate dosage of an active agent, will depend on the type of disease to be treated or function being targeted, as defined above, the severity and course of the disease, whether the agent is administered for preventive or therapeutic purposes, previous therapy, the subject's clinical history and response to the agent, and the discretion of the attending physician. The agent is suitably administered to the subject at one time or over a series of treatments. Dosages and desired drug concentration of compositions may vary depending on the particular use envisioned. The determination of the appropriate dosage or route of administration is well within the skill of an ordinary artisan. Animal experiments provide reliable guidance for the determination of effective does for human therapy.

As used herein, the terms "treating," "treatment," "therapy," and the like, as used herein refer to curative therapy, prophylactic therapy, and preventive therapy, including therapy of healthy subjects. An example of "preventive therapy" is the prevention or lessened targeted pathological condition or disorder. Those in need of treatment include those already with the disorder as well as those prone to have the disorder or those in whom the disorder is to be prevented. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption but, rather, is cyclic in nature. Administration "in combination with" one or more further therapeutic agents includes simultaneous (concurrent) and consecutive administration in any order. In some embodiments, compositions and methods disclosed herein can be used for treating conditions associated with or characterized by muscle atrophy including sarcopenia, sarcopenic obesity, a cancer, multiple sclerosis, muscular dystrophy, a bone fracture requiring immobilization (e.g., splint or cast), amyotrophic laterals sclerosis (ALS), a peripheral neuropathy, stroke, cachexia, or the like. Such conditions can be idiopathic, secondary to a diagnosed condition, or the like.

As used herein, a "therapeutically-effective amount" is the minimal amount of active agent (e.g., a composition comprising *Rhodiola* and *Rhaponticum* extracts) which is necessary to impart therapeutic benefit to a subject. For example, a "therapeutically-effective amount" to a subject suffering or prone to suffering or to prevent it from suffering is such an amount which induces, ameliorates, or otherwise causes an improvement in the pathological symptoms, disease progression, physiological conditions associated with or resistance to succumbing to the aforedescribed disorder.

The following examples are included to demonstrate preferred embodiments. It should be appreciated by those of skill in the art that the techniques disclosed in the examples which follow represent techniques discovered to function well, and thus may be considered to constitute preferred modes for its practice. Those skilled in the art, however, should in light of the disclosure, appreciate that many changes can be made in the specific embodiments which are disclosed and still obtain a like or similar result without departing from the spirit and scope of the embodiments.

Extract Preparation

Extracts may be prepared using an organic solvent extraction process. For example, *Rhaponticum carthamoides* roots may be ground (e.g., to a size of 4 mm mesh) and the ground material mixed with a solvent including, but not limited to, 100% water, ethanol 1% to 99% in water (v/v), methanol 1% to 99% in water (v/v), ethyl acetate, acetone, hexane or any other organic solvent conventionally used for extraction (e.g. EtOH 50%) in a reactor or any container having a function of extraction. A suitable ratio of solvent:plant is between about 1:1 to 30:1, more preferably between 5:1 and 15:1 (e.g. 10:1 (v/w)). The raw material is extracted, for instance under reflux with agitation but can be by means of maceration, with or without reflux, with or without agitation and with or without pressure applied. The extraction temperature will usually depend on the solvent used. The extraction time is preferably at least than 1 h (e.g. 1 h30).

After the extraction time, the mixture may be filtered or centrifuged in order to separate the liquid of the solid phase (cake). In the filtration step, filters of 25 micron may be used.

The extraction step may be repeated more times to achieve more than one cover (e.g. repeated 2 times to achieve a total of 3 covers) and the filtrates combined. The solid phase is discarded.

The combined filtrates may be concentrated under vacuum (e.g. 0.8 Pa) to between 30% and 70% DM (preferably 50% DM). Any type of solvent evaporation system may be used. The resulting extraction past is called the "native extract."

The native extract is then dried to a % DM content of about 90% to 99% (e.g. 97%) but may be dried to a lower % DM. This step can be carried out by any drying process including, but not limited to, atomization, air drying, oven-drying, sun drying, etc. with or without carrier.

Example 1: *Rhaponticum* Extraction with Ethanol 50% (v/v) (F0)

Figures 29A, 29B:
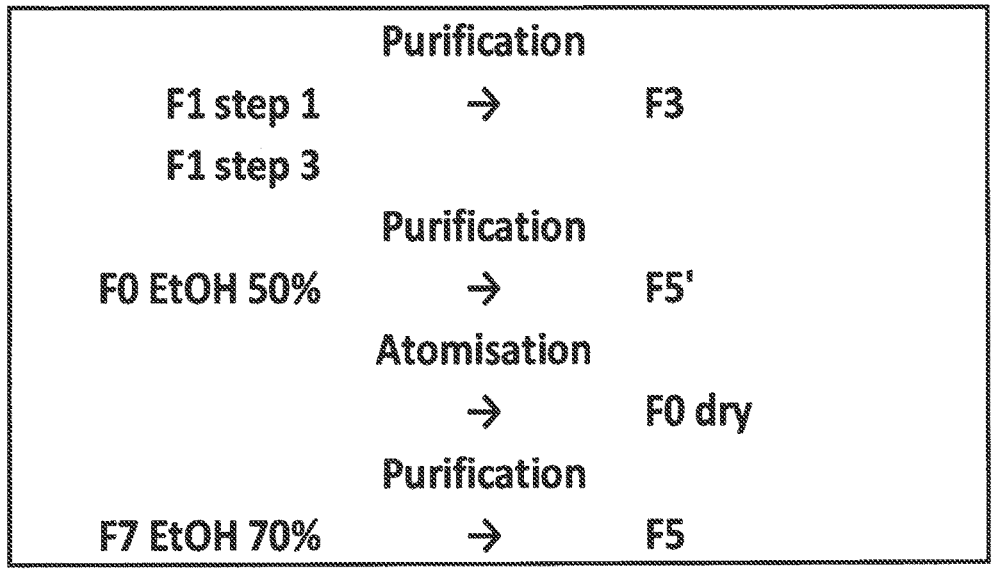
FIG. 29a is a flow chart representing an extraction process for *Rhaponticum* root.
FIG. 29b is a flow chart representing fractions obtained with different solvents.

A schematic version of the following extraction process is shown in FIG. 29a. The *Rhaponticum* raw herb (root, 65 kg dry basis) was weighed and ground into coarse powder. The powder was put into an extraction chamber/a reactor and 700 L of ethanol 50% in water (v/v, 50% alcohol) was added to the raw material, which is an approximate ratio of 10:1 (v/w)). The mixture was heated under reflux with agitation for 1.5 hours, at a temperature of 80-90° C. After 1.5 hours, the liquid was filtered and kept aside. The residue (solid phase) was recovered and the extraction step was repeated two more times (to achieve a total of three covers).

The filtrates were combined before being concentrated under vacuum (0.8 Pa) to 30-60% DM (e.g. 39% DM). A total of 25 kg of the concentration paste (called "F0-native extract") was obtained and analyzed for bioactive ingredients.

In this process, the ethanol may be recollected from the filtrate and reused in the extraction step, making sure the solvent is always at 50% alcohol.

The concentrated extraction paste was then dried by atomization to give a dried powder (less than 10% moisture) (F0-EtOH 50% dried powder). A dry powder sample was obtained and used for bioactive ingredient analysis, microbial analysis, heavy metals analysis, pesticides analysis, and nutritional analysis.

Example 2: Centrifugation and Filtration Steps (F0 as Depicted in FIG. 29a)

12 kg of *Rhaponticum* native extract (at 39% DM) prepared according to Example 1 was diluted with water to 10% DM, then centrifuged. The yield was 43 kg of diluted native extract at approx. 10% DM (F0-Native diluted and centrifuged).

On 42 kg of this diluted native extract (at 10% DM) was performed ultrafiltration (UF) at 5 kDa then at 1 kDa to obtain 3 fractions: >5 kDa, 1-5 kDa and <1 kDa. Fractions were dried under vacuum or atomization (yield were 1.55 kg, 0.90 kg and 1.15 kg, respectively) (F0-Native UF). A sample was sent for bioactive analysis.

Example 3: Purification Step (F5' as Depicted in FIG. 29a)

1 kg of *Rhaponticum* diluted native extract (at approx. 10% DM) prepared according to Example 2 (F0-Native diluted and centrifuged) was purified on an adsorbent resin column D-101 (resin volume 1 L). The eluate was concentrated, and dried to give fine powder ((14.5 g of purified extract powder obtained) (F5'-Purified EtOH50% extract).

Example 4: *Rhaponticum* Extraction Process with Ethanol 70% (v/v) (F5 & F7)

A known amount of *Rhaponticum* root ground to coarse powder was mixed with water at a solvent:plant ratio of 10:1 (v/w) and extracted without reflux at 80° C. for 2 hrs. A single extraction was done. The solid phase was discarded and the liquid phase is recovered and filtered to 25 µm.

Part of the filtrate was concentrated using a Rota evaporator to remove most of the solvent and finally dried under vacuum to <10% moisture. The extract was a powder (F7: EtOH 70% extract).

The other part of the filtrate was purified on adsorbent resin column as described in Example 3, concentrated and dried under vacuum to <10% moisture. The extract was a powder (F5-Purified EtOH 70% extract).

Example 5: *Rhaponticum* Extraction Process with Water (F1 & F3)

The same procedure was repeated as in Example 4 except that water is used instead of EtOH 70%:

A known amount of *Rhaponticum* root ground to coarse powder was mixed with water at a solvent:plant ratio of 10:1 (v/w) and extracted without reflux at 80° C. for 2 hrs. A single extraction was done. The solid phase was discarded and the liquid phase was recovered and filtered to 25 µm.

Part of the filtrate was concentrated using a Rota evaporator to remove most of the water and finally dried under vacuum to <10% moisture. The extract was a powder (F1: Aqueous extract).

The other part of the filtrate was purified on adsorbent resin column as described in Example 3, concentrated and dried under vacuum to <10% moisture. The extract was a powder. (F3-Purified aqueous extract).

Example 6: *Rhaponticum* Extraction Process with Acetone (F2 & F4)

The same procedure was repeated as in Example 4 except that acetone is used instead of EtOH 70%:

A known amount of *Rhaponticum* root ground to coarse powder was mixed with acetone at a solvent:plant ratio of 10:1 (v/w) and extracted without reflux at 80° C. for 2 hrs. A single extraction was done. The solid phase was discarded and the liquid phase was recovered and filtered to 25 µm.

Part of the filtrate was concentrated using a Rota evaporator to remove most of the solvent and finally dried under vacuum to <10% moisture. The extract was a powder. (F2: Acetone extract).

The other part of the filtrate was purified on adsorbent resin column, concentrated and dried under vacuum to <10% moisture. The extract was a powder. (F4-Purified acetone extract).

Example 7: *Rhodiola rosea* Herbal Extract Preparation

Dried *Rhodiola rosea* material was extracted using aqueous alcohol. For example, in some preparations, aqueous ethanol at 50% or at 70% ethanol was preferred. The obtained extract was then filtered and the supernatant was concentrated. The filtered extract was centrifuged and the clear supernatant was purified by column. Ethanol was used to elute the column. The obtained ethanol elution was then concentrated. Some preparations included an optional drying step.

Example 8: Salidrosides and Total Rosavins Dosage in *Rhodiola rosea* Herbal Extract The amount of various compounds, including salidrosides, and total rosavins (rosarin, rosavin and rosin), was determined in *Rhodiola rosea* root extract using the HPLC method developed by: M. Ganzera et al., "Analysis of the marker compounds of *Rhodiola rosea* L. (Golden root) by reversed phase high performance liquid chromatography" Chem. Pharm. Bull. 49(4) 465-467 (2001). Briefly, quantification of target compounds was performed on an HPLC Agilent 1100 HPLC system equipped with a UV detector. The separation of compounds was carried out on ACE C18 HPLC column (250×4.6 mm, 5 μm) set at 45° C. The mobile phase consisted of acetonitrile (eluent A) and Phosphate buffer pH 7 (eluent B). The gradient was as follow: 11% isocratic A (10 min), 11-30% A (20 min), 30-80% A (5 min), 80% isocratic A (10 min), 80-11% A (5 min). The total run time was 50 min. Injection volume was 5 μL and flow rate was 1 mL/min. UV monitoring was performed at 225 nm for salidrosides detection and 250 nm for rosavins detection. The amount of target compounds were quantified by comparing peak area of the sample with peak area of reference compound of known concentration.

TABLE 1

Salidrosides and total rosavins (rosarin, rosavin and rosin) in *Rhodiola rosea* root extract.

| Active | A007/001/D14 | A139/047/A14 | Range |
|---|---|---|---|
| Salidroside (%) | 3.414 | 2.595 | 1 to 4% |
| Rosarin (%) | 0.746 | 0.751 | 0.7 to 0.8% |
| Rosavin (%) | 3.121 | 2.996 | 2 to 5% |
| Rosin (%) | 0.337 | 0.514 | 0.3 to 0.6% |
| Total Rosavins (%) | 4.204 | 4.261 | 3 to 6% |

Example 9: 20HE Analysis in the Different *Rhaponticum* Root Extracts

The amount of beta-ecdysone (20HE) in the different *Rhaponticum* extracts prepared as in Examples 1 to 6 was determined using an Agilent 1100 HPLC system equipped with a UV-Vis detector. Compound separation was carried out on a Zorbax Eclipse Plus C18 HPLC column (2.1×50 mm-1.8 micron) with column temperature set at 35° C. The mobile phase consisted of methanol (eluent A) and 0.1% formic acid in water (eluent B). The flow rate was 0.4 mL/min. The gradient was linear with ramp 10 to 100% A in 15 min. The injection volume was 2 μL. UV monitoring was performed at 250 nm, bw 8 nm. The amount of target compounds was quantified by comparing peak area of the sample with peak area of reference compound of known concentration.

TABLE 2

Concentration of 20-Hydroxyecdysone (20-HE) in the different fractions of *Rhaponticum carthamoides* extracted with ethanol (50%), ethanol (70%), water or acetone, with or without subsequent purification on column.

| Fractions | Extraction Example | 20HE % odb measured | Range (% odb) |
|---|---|---|---|
| Extraction solvent EtOH 50% (F0 & F5') | | | |
| F0-Native extract (labo-60% DM)* | Example 1 | 0.18-0.21* | 0.1-0.3* |
| F0-Native extract (pilot-38% DM)* | Example 1 | 0.14* | 0.1-0.3* |
| F0- EtOH 50% dried powder | Example 1 | 0.37-0.40 | 0.3-0.5 |
| F0- native diluted & centrifuged (7% DM) | Example 2 | 0.13 | 0.1-0.3 |
| F5'-Purified EtOH 50% extract | Example 3 | 2.31-2.52 | 2.0-3.0 |
| Ultra Filtration | | | |
| UF >5 kDa | Example 2 | 0.53 | 0.5-1.0 |
| UF 1-5 kDa | Example 2 | 0.33 | 0.1-0.5 |
| UF <1 kDa | Example 2 | 0.38 | 0.1-0.5 |
| Extraction solvent EtOH 70% (F5 & F7) | | | |
| F7- 70% EtOH extract | Example 4 | 0.37-0.48 | 0.2-0.5 |
| F5- purified 70% EtOH extract | Example 4 | 0.89-1.60 | 0.8-2.0 |
| Extraction solvent Water (F1 & F3) | | | |
| F1- aqueous extract | Example 5 | 0.18-0.38 | 0.1-0.5 |
| F3- purified aqueous extract | Example 5 | 1.48-1.96 | 1.2-2.0 |
| Extraction solvent Acetone | | | |
| F2- acetone extract | Example 6 | 0.63 | 0.5-0.7 |
| F4 - Purified acetone extract | Example 6 | 3.30 | >3.0 |

*values are expressed on sample as analyzed and not on dry basis

Example 10: Ecdysteroids Analysis of Ethanolic *Rhaponticum* Root Extract

Dried extract of *Rhaponticum carthamoides* root (F0-EtOH 50% dried powder) was obtained by extraction with 50% (v/v) ethanol in water as described in Example 1. Identification of ecdysteroids was performed using an HPLC system equipped with a Photodiode Array Detector. The separation was carried out on an Atlantis C18 HPLC column (150×3 mm-3 μm) set at 40° C. The mobile phase consisted of methanol with 0.1% acetic acid (v/v, eluent A) and 0.1% (v/v) acetic acid in water (eluent B). The flow rate was 0.6 mL/min. The gradient program was as follow: 20% isocratic A (5 min), 20-40% A (25 min), 40-70% A (15 min), 70-85% A (15 min). Total run time is 60 min. Monitoring was performed at 242 nm.

TABLE 3

Ecdysteroids identified in ethanolic (50% v/v) extract of *Rhaponticum carthamoides* root dried to powder form (moisture <10%)

| Retention time | Formula | Compounds | % |
|---|---|---|---|
| 20.2 | $C_{27}H_{42}O_7$ | | 0.005% |
| 20.8 | $C_{27}H_{44}O_9$ | Integristerone B | Nq |
| 24.9 | $C_{27}H_{42}O_7$ | Isovitexirone | 0.007% |
| 30.5 | $C_{27}H_{44}O_8$ | | Nq |
| 30.7 | $C_{27}H_{44}O_7$ | 20-Hydroxyecdysone | 0.395% |
| 31.1 | $C_{29}H_{42}O_8$ | | Nq |
| 32.1 | $C_{27}H_{44}O_7$ | | 0.006% |
| 33.7 | $C_{27}H_{42}O_7$ | 22-Oxo-20-hydroxyecdysone | 0.012% |
| 35.3 | $C_{27}H_{44}O_7$ | | 0.013% |
| 35.6 | $C_{28}H_{44}O_6$ | | Nq |
| 35.7 | $C_{28}H_{46}O_7$ | Makisterone A | 0.003% |
| 36 | $C_{28}H_{44}O_7$ | 24(28)-Dehydromakisterone A | 0.004% |
| 37.3 | $C_{27}H_{44}O_7$ | | 0.158% |
| 38.3 | $C_{29}H_{44}O_6$ | | 0.144% |
| 38.6 | $C_{29}H_{46}O_8$ | | Nq |

TABLE 3-continued

Ecdysteroids identified in ethanolic (50% v/v) extract of
Rhaponticum carthamoides root dried to powder form (moisture <10%)

| Retention time | Formula | Compounds | % |
|---|---|---|---|
| 39.8 | $C_{27}H_{44}O_6$ | Alpha-ecdysone | 0.006% |
| 40.4 | $C_{29}H_{48}O_7$ | | 0.030% |
| 41.2 | $C_{27}H_{44}O_7$ | | Nq |
| 44.5 | $C_{29}H_{44}O_6$ | | 0.005% |

Nq: non quantifiable.
Total ecdysterones (as 20-Hydroxyecdysone) = 0.788%.

A total of 19 ecdysteroids were identified in the *Rhaponticum* root extract. Some were identifiable only by their chemical structures.

Example 11: Phytochemical and Physicochemical Analysis of Ethanolic Extract of Ethanolic *Rhaponticum* Root Extract (Excluding Ecdysteroids)

The dried extract of *Rhaponticum* carthamoides root (F0-EtOH 50% dried powder) was obtained by extraction with 50% (v/v) ethanol in water as described in Example 1 and analyzed for phyto-compounds other than ecdysteroids and physical analysis. Graphs of total phenolics, total organic acids and total free carbohydrates identified in the composition are depicted in FIGS. 1a, 1b and 2.

TABLE 5

Physical analysis (spectrophotometry and gravimetry)
of ethanolic (50% v/v) extract of *Rhaponticum carthamoides*
root dried to powder form.

| OPC As Folin denis | Phenolic As Folin C. | Total fiber AOAC method | Proteins Kehjdal | Ash EuP. | Water (Balance IR.) |
|---|---|---|---|---|---|
| 0.7% | 13.4% | 6.7% | 2.7% | 16.7% | 3.95% |

Total Ash, Fiber, protein, water and HPLC/GC results give 70.6% of the extract identified, compounds such as acetylene thiophenes and sterol are found in low amounts (identified but not quantified).

Methods of Using *Rhaponticum* and *Rhodiola* Extracts

The following examples evaluated the effect of *Rhaponticum* extract and *Rhodiola* extract, alone and in combination, on protein synthesis and metabolic signaling pathways.

Example 12: Phosphorylation of S6K1 on Threonine 389 and of Akt on Threonine 308 of Different Preparations of *Rhaponticum* Carthamoides Extracts (Step 1 as Depicted in FIG. 29a)

A study was designed to evaluate the ability of *Rhaponticum* extract to stimulate protein synthesis and metabolic pathways at level of Akt. The serine/threonine kinase Akt (protein kinase B) is activated by a variety of stimuli through phosphorylation on $Thr^{308}$ and $Ser^{473}$. Once phosphorylated Akt migrates to the nucleus where it is involved in a variety of cellular processes such as glucose transport, protein synthesis or lipid and triglyceride storage.

The ability of *Rhaponticum* extract to stimulate protein synthesis at level of S6 kinase 1 also was evaluated. The sp70 S6 kinase is a ubiquitous cytoplasmic protein that is activated in response to cytokines. It lies downstream of the mTOR/PI3K pathway and is phosphorylated on multiple residues including threonine 389. Phosphorylation of Thr389, however, most closely correlates with p70 kinase activity in vivo. Once activated, the p70 S6 kinase phosphorylates the S6 protein on the 40S ribosomal protein (rpS6) that leads to protein synthesis process.

C2C12 cells were originally obtained by Yaffe and Saxel (1977) through selective serial passage of myoblasts cultured from the thigh muscle of C3H mice 70 h after a crush injury (Yaffe D, 1977). These cells were shown to be capable of differentiation. C2C12 cells are a useful model to study the differentiation of myogenic cells into skeletal muscle cells (e.g myosin phosphorylation mechanisms) and express muscle proteins and the androgen receptor.

Five different preparations of *Rhaponticum* extract were prepared: 50% ethanol extract, 70% ethanol extract, 100% water extract, as well as extracts purified on column (except for the 50% EtOH), as described in Examples 1 to 5 of the present disclosure.

TABLE 6

*Rhaponticum* preparations

| Nb | Extract | Fraction | Batch | Date reception | Storage | Est. weight | Observations |
|---|---|---|---|---|---|---|---|
| 1 | Rhaponticum | F0, NE-ETOH 50% | TL19/06/13-1 | 2013 Nov. 19 | +4° C. | 22.1 g | Brown suspension |
| 2 | Rhaponticum | F1, primary aqueous extract | LAU-2540218/A | 2013 Nov. 19 | +4° C. | 24.0 g | Brown powder |
| 3 | Rhaponticum | F3, purified aqueous extract | LAU-2390207/B | 2013 Nov. 19 | +4° C. | 5.3 g | Brown powder |
| 4 | Rhaponticum | F5, purified ethanol extract | LAU-2410208/B | 2013 Nov. 19 | +4° C. | 6.4 g | Green powder |
| 5 | Rhaponticum | F7, primary ethanol extract | LAU-2600224 | 2013 Nov. 19 | +4° C. | 22.8 g | Brown adhesives smithereens |

Concentrations tested for each preparation of *Rhaponticum* extract were prepared in order to have a final concentration in hydroxy-ecdysone of 0.1 µM, 1 µM and 10 µM. Based on concentration of hydroxy-ecdysone measured in each extract, the concentrations used for each preparation of *Rhaponticum* were as follows:

TABLE 7

| Compound | % of Hydroxy-ecdysone amount (%20 HE) | Final concentration of extract after dilution in DMEM (in wells) | Final concentration in Hydroxy-ecdysone (in wells) |
|---|---|---|---|
| F0 (liquid NE-ETOH 50% extact) | .21% | 10 µg/mL | 0.04 µM |
| | | 100 µg/mL | 0.4 µM |
| | | 1001 µg/mL | 4.4 µM |
| F1 (primary aqueous extract) | 0.38% | 12.6 µg/mL | 0.1 µM |
| | | 126 µg/mL | 1 µM |
| | | 1265 µg/mL | 10 µM |
| F3 (purified aqueous extract) | 1.96% | 2.5 µg/mL | 0.1 µM |
| | | 25 µg/mL | 1 µM |
| | | 245 µg/mL | 10 µM |
| F5 (purified ethanol extract) | 1.60% | 3 µg/mL | 0.1 µM |
| | | 30 µg/mL | 1 µM |
| | | 300 µg/mL | 10 µM |
| F7 (primary ethanol extract) | .48% | 10 µg/mL | 0.1 µM |
| | | 100 µg/mL | 1 µM |
| | | 1001 µg/mL | 10 µM |

At the beginning of the study the value of % of hydroxy-ecdysone for F0 extract was not determined and the final concentration tested was based on the hydroxyl-ecdysone concentration in the F7 extract. However, the concentration of this ecdysone in the F0 was overestimated. This is the reason why the final concentration of hydroxy-ecdysone tested for the F0 extract was different from the other fractions.

Growing cells were harvested and plated at a density of 170 000 cells per well in a 6 well plate. Cells were grown for 48 h in 5% $CO_2$ at 37° C. After cells reached 80% confluence, the medium was replaced with differentiating medium (DMEM+2% FBS). After 5 days, myoblasts were fused into multinucleated myotubes. 1 h before starting the experiment, cells were incubated in Krebs medium to deprived cells of amino acids.

Cells were treated with five preparations of *Rhaponticum* plant extract at 3 concentrations in the presence of normal (0.8 mM) or low (0.08 mM) concentration of amino acids and with DMSO 0.002% for 2 h.

At the end of the experiment, cells were lysed in cell lysate buffer (100 µL per well) and centrifuged to isolate the soluble protein in supernatant. Proteins from this cellular assay were quantified using a colorimetric assay derived from LOWRY method. Therefore, 50 µg of total protein in 100 µL lysis buffer were transferred into microwell strips coated with pS6K1 or pAkt antibody and incubated 2 h at 37° C. After several washes, the detection antibody was added and incubated 1 h at 37° C. Once again several washes were processed and HRP-linked secondary antibody was added. At the end of the 30 min incubation at 37° C., the TMB (3,3',5,5'-Tetramethylbenzidine) substrate was added and a blue color was developed in positive wells. To avoid saturation of signal a stop solution was added which induce a yellow color. Intensity of the yellow color was readable on a spectrophotometer at 450 nm and directly proportional to pS6K1 or Akt amount detected.

Each condition is tested in n=5 or n=6. IGF1 100 ng/ml was used as a positive control.

Results of phosphorylated Akt is expressed in absorbance per µg of protein (Abs/µg protein) after 2 hrs incubation and in % of untreated control condition (100%).

Results of phosphorylated T389 S6 kinase1 is expressed in absorbance per µg of protein (Abs/µg protein) after 2 hrs incubation and in % of untreated control condition (100%).

All results are expressed in % of untreated control. Differences between obtained values were evaluated by ANOVA for repeated measurements followed by a Dunnett t test, if ANOVA reveals significant differences by a U-Mann-Whitney test to compare untreated controls versus IGF1 or plants extracts; * p<0.05, p<0.01, *p<0.001, versus the untreated control.

All results are given as mean±SEM. For all the evaluated parameters statistical analyses were performed using a Kruskall-Wallis non parametric test followed by the Dunn's post test (GraphPad PRISM®4). Comparison between two conditions was performed using a Mann Whitney test. A p value of 0.05 was considered as significant.

Insulin like growth factor-1 (IGF-1) is established as an anabolic factor that can induce skeletal muscle growth by activating the phosphoinositide 3-kinase (PI3K)/Akt/mammalian target of rapamycin (mTOR) pathway. Stimulation of phosphorylation of both S6K1 and Akt was already reported by Miyazaki et al. (Miyazaki M, 2010). Therefore, IGF-1 was chosen as a positive control of the experiment. Basal phosphorylation of S6K1 was four times higher in the presence of normal concentrations of amino acids than in the presence of low amino acid concentration (0.8 mM vs 0.08 mM).

In the presence of low concentration of amino acids, all the tested fractions, except F7, at all the tested doses increased S6K1 phosphorylation (See FIGS. 3a, 3b, 4a, 4b, 5a, 5b, 6a, 6b, 7a, and 7b). The effects were not dose-dependent at the tested doses.

In the presence of normal concentration of amino acids, the lowest dose of each fraction, except F3, and the intermediate concentration of F0, F3 and F5 stimulated S6K1 phosphorylation (See FIGS. 3a, 3b, 4a, 4b, 5a, 5b, 6a, 6b, 7a, and 7b). The observed effects were lower than those observed with IGF-1 and were significant only for F0, F1 and F3 fractions (lowest or intermediate doses). It has to be noted that under condition of partial solubility of the F7 extract of intermediate and high concentrations tested, a drop in S6K1 phosphorylation was reported. FIGS. 3a, 3b, 4a, 4b, 5a, 5b, 6a, 6b, 7a, and 7b: Determination of S6K1 phosphorylation on threonine 389 in C2C12 myotubes after incubation with 5 different preparations of *Rhaponticum* extract at three concentrations.

Five different preparations of *Rhaponticum* extract at three concentrations were incubated for 2 h in the presence of differentiated C2C12 myotubes. At the end of incubation cells were lysed, total soluble proteins were quantified and level of S6K1 phosphorylation on residue threonine 389 was measured and normalized to beta-actin protein. Mean±SEM. *p<0.05; p<0.01; *p<0.001 vs control value.

IGF-1 was previously reported to stimulate Akt phosphorylation and was in this context chosen as a positive reference in the assay (Miyazaki M, 2010). After IGF-1 (100 ng/mL, 2 h) incubation, Akt phosphorylation was activated by a factor 1.6 for. Similar results were previously published for Akt phosphorylation by Latres or Miyazaki (Latres E, 2005) (Miyazaki M, 2010).

In the presence of low or normal amino acid concentration, a non-significant stimulation of Akt phosphorylation was observed for all the different tested fractions at the lowest dose except for fraction F0 incubated with low amino acid concentration and F3 incubated with normal amino acid concentration, where a non-significant increase was observed with the intermediate dose.

It was noted that basal level of Akt phosphorylation was twice higher in the presence of normal amino acid condition compared to low amino acid condition. Finally, under condition of partial solubility of the F1 (high concentration) or F7 (intermediate and high concentrations) extracts, a drop in Akt phosphorylation was documented whatever the concentration of amino acids used.

FIGS. 8a, 8b, 9a, 9b, 10a, 10b, 11a, 11b, 12a, 12b: Determination of Akt phosphorylation on threonine 308 in C2C12 myotubes after incubation with 5 different preparations of *Rhaponticum* extract at three concentrations.

Five different preparations of *Rhaponticum* extract at three concentrations were incubated for 2 h in the presence of differentiated C2C12myotubes. At the end of the incubation cells were lysed, total soluble proteins were quantified and level of Akt phosphorylation on residue threonine 308 was measured and normalized to beta-actin protein. Mean±SEM. *$p<0.05$; $p<0.01$; *$p<0.001$ vs control value.

Example 13: Effect of 5 Different Preparations of *Rhaponticum* Carthamoides Extracts on Protein Synthesis (Tritiated Leucin Incorporation) in C2C12 Myotubes (Step 1 as Depicted in FIG. 29a)

A study was designed to evaluate the ability of plant extracts to stimulate protein synthesis by measuring the incorporation of the tritiated leucine. C2C12 cells and the five different preparations of *Rhaponticum* extracts were prepared as in Example 12.

For the protein synthesis assay, growing cells were harvested and plated at a density of 30 000 cells per well in a 24 well plate. Cells were grown for 48 h in 5% $CO_2$ at 37° C. After cells reached 80% confluence, the medium was replaced with differentiating medium (DMEM+2% FBS). After 5 days, myoblasts were fused into multinucleated myotubes. Protein synthesis was determined by measuring the incorporation of the tritiated amino acid leucine. Briefly, 1 h prior leucine challenge, cells were incubated in amino acid free-medium. Then cells were incubated for 2 h30 in the presence of: radiolabelled leucine 5 µCi/mL and IGF1 100 ng/mL or plant extract in the presence of normal (0.8 mM) or low (0.08 mM) concentration of amino acids and with DMSO 0.002%

All results are expressed in % of untreated control. Differences between obtained values are evaluated by ANOVA for repeated measurements followed by a Dunnett t test, if ANOVA reveals significant differences by a U-Mann-Whitney test to compare untreated controls versus IGF1 or plants extracts; * $p<0.05$, $p<0.01$, *$p<0.001$, versus the untreated control.

All results are given as mean±SEM. For all the evaluated parameters statistical analyses were performed using a Kruskall-Wallis non parametric test followed by the Dunn's post test (GraphPad PRISM®4). Comparison between two conditions was performed using a Mann Whitney test. A p value of 0.05 was considered as significant.

IGF1 induced protein synthesis in the presence of low (+45%, $p<0.001$) or normal concentration (+21%, $p<0.001$) of amino acids. The test was validated since data with IGF-1 on protein synthesis are similar to data reported in the literature that described an increase in protein synthesis of 20-50% in the presence of IGF1 with low or normal concentration of amino acids (Kazi A A, 2010) (Broussard S R, 2004). It was noted that incorporation of radioactivity was higher in the presence of low amino acid concentration, indicating that competition between radioactive leucine and cold leucine was weaker than in the presence of normal concentration of amino acids, as expected.

Among the different preparations of *R. Carthamoides*, fractions F0 (native EtOH50%), F5 (purified EtOh70% extract) and F7 (EtOH70% extract) were able to significantly stimulate protein synthesis. This stimulation was equivalent or stronger than the reference of the assay: IGF1 (IGF-1 100 ng/mL+21% $p<0.001$ versus F0 10 µg/mL+43% $p<0.001$ or F5 300 µg/mL+23% $p<0.01$ or F7 10 µg/mL+ 29% $p<0.001$). The fraction F5 stimulated protein synthesis in a dose dependent manner and significant effect from 30 µg/mL which corresponded to a concentration of 20HE of 1 µM. Additionally, F0 and F7 fractions exhibited best effect at lowest dose (respectively equivalent to 0.04 µM and 0.1 µM of 20HE). The stimulation of protein synthesis induced by fraction F0 10 µg/mL was significantly higher than that observed with IGF-1.

Fractions F1 (aqueous extract) and F3 had very slight, non-significant effect in presence of low amino acids and this was also true for F3 at higher concentration of amino acid.

FIGS. 13a, 13b, 14a, 14b, 15a, 15b, 16a, 16b, 17a, 17b: Determination of protein synthesis in C2C12 myotubes after incubation with 5 different preparations of *Rhaponticum* extract at three concentrations.

Five different preparations of *Rhaponticum* extract at three concentrations were incubated for 2 h30 in the presence of differentiated C2C12 myotubes and tritiated leucine (5 µCi). At the end of the incubation cells were lysed, total soluble proteins were quantified and level of tritiated leucine incorporated into cells was counted. Mean±SEM. *$p<0.05$; $p<0.01$; *$p<0.001$ vs control value.

In summary of these experiments, in the presence of normal concentration of amino acids, F0, F5 and F7 fractions significantly stimulated protein synthesis. This stimulation was similar or stronger than the reference of the assay, IGF-1 (IGF-1 100 ng/mL, +20%, $p<0.001$ versus F0 10 µg/mL, +43%, $p<0.001$ or F5 300 µg/mL, +23%, $p<0.01$ or F7 10 µg/mL, +29%, $p<0.001$). These fractions also stimulated signaling pathway (Akt and S6K1 phosphorylations) at the low doses tested. It was noted for F1 1300 µg/mL and F7 1000 µg/mL solubility trouble in all the assays.

On the other hand, F1 and F3 fractions did not stimulate protein synthesis. However, some stimulation of Akt and S6K1 phosphorylations was observed with these fractions.

In conclusion, F0 fraction and to a lesser extent F7 fraction, both at the lowest concentrations (equivalent to 0.04-0.1 µM 20HE), increased Akt and S6K1 phosphorylation which was correlated with a significant increase in protein synthesis.

Example 14: Effect of One Selected Preparation of *Rhaponticum* Carthamoides Extract with *Rhodiola* on Protein Synthesis (Tritiated Leucin Incorporation) in C2C12 Myotubes (Step 2a and b as Depicted in FIG. 29a)

Under our experimental condition, best results were obtained with lowest doses of F0 fraction in the presence of normal amino acid concentration showing stimulation of protein synthesis and activation of the signaling (induction of S6K1 and akt phosphorylations) (see Example 13). Therefore, this fraction was selected to be tested in co-incubation experiment with another plant extract preparation derived from *Rhodiola* species that contains salidroside as active component.

The *Rhodiola* extract used continued:

| Nb | Extract | % of Salidroside | % of Rosavin | Observation |
|----|---------|------------------|--------------|-------------|
| 1 | *Rhodiola* | 2.88% | 3.49% | Brown powder |

In a first part of the study, the best effect for *Rhaponticum* plant extract was documented with F0 fraction at the lowest dose, a new dose response evaluation at 0.1-1-10 µg/mL was performed on protein synthesis in parallel to a dose response analysis of *Rhodiola* extract. Concentrations of *Rhodiola* chosen were: 10-104-417 µg/mL corresponding to final salidroside concentrations of 1-10-40 µM.

| Compound | % of Hydroxy-ecdysone amount (%20 HE) | Final concentration of extract after dilution in DMEM (in wells) | Final concentration in Hydroxy-ecdysone (in wells) |
|---|---|---|---|
| F0 (liquid NE-ETOH 50% extact) | .21% | 1 µg/mL | 0.004 µM |
| | | 5 µg/mL | 0.02 µM |
| | | 10 µg/mL | 0.04 µM |

| Compound | % of Salidroside | % of Rosavin | Final concentration of *Rhodiola* after dilution in DMEM (in wells) | Final concentration in Salidroside (in wells) | Final concentration in Rosavin (in wells) |
|---|---|---|---|---|---|
| *Rhodiola* | 2.88% | 3.49% | 10.4 µg/mL | 1.0 µM | 0.8 µM |
| | | | 104.3 µg/mL | 10.0 µM | 8.5 µM |
| | | | 417.1 µg/mL | 40.0 µM | 34.0 µM |

For this study, C2C12 cells were obtained as described in EXAMPLE 12. Protein synthesis assay was performed as described in EXAMPLE 13, except that radiolabelled leucine 5 µCi/mL and IGF1 100 ng/mL, F0 extract at 1, 5 and 10 µg/ml or *Rhodiola* extract at 10, 104 and 417 µg/ml in the presence of normal (0.8 mM) concentration of amino acids and with DMSO 0.005% were used.

FIGS. 18a and 18b: Determination of protein synthesis in C2C12 myotubes after incubation with *Rhaponticum* F0 and *Rhodiola* extracts at three concentrations.

*Rhaponticum* F0 and *Rhodiola* extracts at three concentrations were incubated for 2 h30 in the presence of differentiated C2C12 myotubes and tritiated leucine (5 µCi). At the end of the incubation cells were lysed, total soluble proteins were quantified and level of tritiated leucine incorporated into the cells was counted. Mean±SEM. *$p<0.05$; $p<0.01$; *$p<0.001$ vs control value.

All results are given as mean±SEM. For all the evaluated parameters statistical analyses were performed using a Kruskall-Wallis non parametric test followed by the Dunn's post test (GraphPad PRISM®4). Comparison between two conditions was performed using a Mann Whitney test. A p value of 0.05 was considered as significant.

IGF1 induced protein synthesis in the presence of normal concentration of amino acids as previously reported (Kazi A A, 2010) (Broussard S R, 2004). This result confirmed our previous data generated in step 1 (IGF-1 step 1+21%, $p<0.001$ vs IGF-1 step 2+27%, $p<0.01$).

F0 fraction was able to significantly stimulate protein synthesis at 1 µg/mL (See FIGS. 18a and 18b). This stimulation was similar to the reference of the assay: IGF-1 (IGF-1 100 ng/mL or F0 1 µg/mL+27% $p<0.01$). A stimulation of protein synthesis was observed with F0 10 µg/mL, however, it did not reach statistical significance and was weaker than in the first step (+16% vs+43%). This difference could be due to the higher concentration of DMSO used in this experiment, based on the solubility of *Rhodiola* extract and anticipation of the next co-incubation experiment. These results indicated that active compound(s) in the F0 extract on protein synthesis is (are) sensitive to DMSO concentration.

*Rhodiola* extract induced protein synthesis at the lowest concentration (+23%, $p<0.01$). This activity was similar to that of IGF-1. By contrast, at 417 µg/mL, *Rhodiola* inhibited protein synthesis (See FIGS. 18a and 18b). However, this high dose was probably due to the solubility limit of the extract and that could lead to deleterious effect on protein synthesis.

Therefore for the next co-incubation experiments, it was decided to test *Rhaponticum* F0 extract and *Rhodiola* extract at 1 and 10 µg/mL, alone and in combination, in DMSO at final concentration of 0.005%. Each preparation was sonicated to improve solubility.

In a second step, different combinations of both plant extracts were studied to determine if potentiating effect on protein synthesis could be documented.

For this study, C2C12 cells were obtained as described in EXAMPLE 12. Protein synthesis assay was performed as described in EXAMPLE 13, except that radiolabelled leucine 5 µCi/mL and IGF1 100 ng/mL, F0 extract at 1 and 10 µg/ml, or *Rhodiola* extract at 1 and 10 µg/ml or combination of F0 with *Rhodiola* at different concentrations in the presence of normal (0.8 mM) concentration of amino acids and with DMSO 0.005% was used.

| Compound | % of Salidroside | % of Rosavin | Final concentration of Rhodiola after dilution in DMEM (in wells) | Final concentration in Salidroside (in wells) | Final concentration in Rosavin (in wells) |
|---|---|---|---|---|---|
| Rhodiola | 2.88% | 3.49% | 1.0 µg/mL | 0.1 µM | 0.1 µM |
| | | | 10.4 µg/mL | 1.0 µM | 0.8 µM |

| Compound | % of Hydroxy-ecdysone amount (%2- HE) | Final concentration of extract after dilution DMEM (in wells) | Final concentration in Hydroxy-ecdysone (in wells) |
|---|---|---|---|
| F0 (liquid NE-ETOH 50% extract) | 0.21% | 1 µg/mL | 0.004 µM |
| | | 10 µg/mL | 0.04 µM |

FIGS. 19a, 19b, 20a, 20b and 21: Determination of protein synthesis in C2C12 myotubes after incubation with *Rhaponticum* F0 and *Rhodiola* extracts alone or in combination at two concentrations.

Two concentrations of *Rhaponticum* F0 and *Rhodiola* extracts were incubated for 2 h30 in the presence of differentiated C2C12 myotubes and tritiated leucine (5 µCi). Additionally, combination of *Rhaponticum* F0 and *Rhodiola* extracts at two different concentrations each were incubated for 2 h30 in the presence of differentiated C2C12 myotubes and tritiated leucine (5 µCi). At the end of the incubation cells were lysed, total soluble proteins were quantified and level of tritiated leucine incorporated into cells was counted. Mean±SEM. *$p<0.05$; $p<0.01$; *$p<0.001$ vs control value.

IGF1 significantly induced protein synthesis in the presence of normal concentration of amino acid as previously reported (+22%, $p<0.05$ vs+27%, $p<0.01$ and +21%, $p<0.001$ in previous studies).

*Rhodiola* strongly and significantly induced protein synthesis at 10 µg/ml as previously reported (+30%, $p<0.001$ vs+23%, $p<0.01$ in the previous step) (See FIGS. 19a, 19b, 20a, 20b and 21).

F0 significantly induced protein synthesis at 1 & 10 µg/ml as previously reported. Similarly to step 1 induction of protein synthesis by F0 (10 µg/mL) was significant and stronger than IGF-1 effect. The difference with the step 2a experiment could be due to the sonication step during the solubilization of the extract. Effects of F0 and *Rhodiola* on protein synthesis were similar when equivalent doses were considered (See FIGS. 19a, 19b, 20a, 20b and 21).

A potentiation was observed with low doses of both extracts (F0 & *Rhodiola* 1:1+19% $p<0.05$ vs F0 1 µg/ml+ 14% NS and *Rhodiola* 1 µg/ml+10% NS). The increase in protein synthesis with the combination was superior to that of *Rhaponticum* or *Rhodiola* extract alone and therefore a potentiating effect was observed.

F0 alone (10 µg/ml), *Rhodiola* alone (10 µg/ml) and the combination thereof all increased significantly protein synthesis as compared to the control. Nevertheless, no potentiation of protein synthesis was observed with the combination of high doses of *Rhodiola* and F0 compared to each extract alone (F0 & *Rhodiola* 10:10+28% $p<0.001$ vs F0 10 µg/ml+29% $p<0.001$ and *Rhodiola* 10 µg/ml+30% $p<0.001$).

A lower effect than each extract alone at high dose (10 µg/ml) but stronger effect than each extract alone at low dose (1 µg/ml) was observed with the combinations of high dose of one extract and low dose of the other (F0 & *Rhodiola* 1:10+16% NS vs F0 1 µg/ml+14% NS and *Rhodiola* 10 µg/ml+30% $p<0.001$ or F0 & *Rhodiola* 10:1+19% $p<0.05$ vs F0 10 µg/ml+29% $p<0.001$ and *Rhodiola* 1 µg/ml+10% NS).

Example 15: Evaluation of Two Concentrations of *Rhaponticum* Extract F0 and Two Concentrations of *Rhodiola* Extract on Myostatin and Atrogin Gene Expressions and Combination Thereof (Step 2c a Depicted in FIG. 29a)

A study was conducted to determine if a potentiation exists on other physiological processes and effect of extracts alone and in combination on muscle proteolysis, by measuring the effect of the extracts and combination thereof on myostatin and atrogin 1 gene expression. The *Rhaponticum* extract F0 and *Rhodiola* extract used as described in Example 14.

For the gene expression assay, growing cells were harvested and plated at a density of 30 000 cells per well in a 24 well plate. Cells were grown for 48 h in 5% CO2 at 37° C. After cells reached 80% confluence, the medium was replaced with differentiating medium (DMEM+2% FBS). After 5 days, myoblasts were fused into multinucleated myotubes.

Cells were treated with F0 extract at 1 and 10 µg/ml, or *Rhodiola* extract at 1 and 10 µg/ml or combination of F0 with *Rhodiola* at different concentrations, for 6 h. At the end of the experiment, C2C12 cells were lyzed in trizol solution and RNA was extracted and purified using the phenol/chloroform method. RNA amount after extraction was quantified by spectrophotometer (260 nm/280 nm/320 nm) and suspended at a final concentration of 1 µg/µL. Subsequently, 1 µg of RNA were used as template for the synthesis of first-strand cDNA using oligo(dT) primers and the AMV reverse transcriptase system as described by manufacturer (Applied Biosystems 4368814). qPCRs were then performed using a 7900HT Fast real-Time PCR detection system (Applied Biosystems) and standard qPCR program (1 cycle 95° C. 15 min, 40 cycles 95° C. 15 s and 60° C. 1 min, a fusion curve 60 to 95° C. for sybergreen probes). Thermocycling experiments were performed in a SYBR green PCR master mix (Applied Biosystems) for beta actin, Myostatin and Atrogin genes containing the 100 ng cDNA samples and a set of primers at a final concentration of 200 nM designed into two different exons.

All results are given as mean±SEM. For all the evaluated parameters statistical analyses were performed using a Kruskall-Wallis non parametric test followed by the Dunn's post test (GraphPad PRISM®4). Comparison between two conditions was performed using a Mann Whitney test. A p value of 0.05 was considered as significant.

| Compound | % of Salidroside | % of Rosavin | Final concentration of Rhodiola after dilution in DMEM (in wells) | Final concentration in Salidroside (in wells) | Final concentration in Rosavin (in wells) |
|---|---|---|---|---|---|
| Rhodiola | 2.88% | 3.49% | 1.0 µg/mL | 0.1 µM | 0.1 µM |
|  |  |  | 10.4 µg/mL | 1.0 µM | 0.8 µM |

| Compound | % of Hydroxy-ecdysone amount (%2- HE) | Final concentration of extract after dilution DMEM (in wells) | Final concentration in Hydroxy-ecdysone (in wells) |
|---|---|---|---|
| F0 (liquid NE-ETOH 50% extract) | 0.21% | 1 µg/mL | 0.004 µM |
|  |  | 10 µg/mL | 0.04 µM |

In the literature, several papers reported inhibition of atrogin gene expression around 40% after 24 h incubation with IGF-1 at 10 ng/mL (Latres E, 2005) (Stitt T N, 2004). No data are published on inhibition of myostatin gene expression by IGF-1 because most of the studies focused on IGF-1 antagonism of deleterious myostatin effect (Trendelenburg A U, 2009). However, internally, we documented a 20-40% inhibitory effect of IGF-1 on myostatin gene expression. Based on literature and internal data IGF-1 was selected as our positive control in this assay. In this experiment IGF1 inhibited significantly myostatin & atrogin gene expressions (respectively, −25%, $p<0.001$ & −59%, $p<0.001$).

FIGS. 23a, 23b, 24a, and 24b: Effect of co-incubation of Rhaponticum F0 and Rhodiola extracts on myostatin gene expression in C2C12 myotubes. Combination of Rhaponticum F0 and Rhodiola extracts at two different concentrations each were incubated for 6 h in the presence of differentiated C2C12 myotubes. At the end of the incubation cells were lysed and RNA was extracted, converted into cDNA to perform a quantitative PCR. Mean±SEM. *$p<0.05$;  $p<0.01$; * $p<0.001$ vs control value; ### $p<0.001$ vs control value (Mann-Whitney test).

Figure 22A:
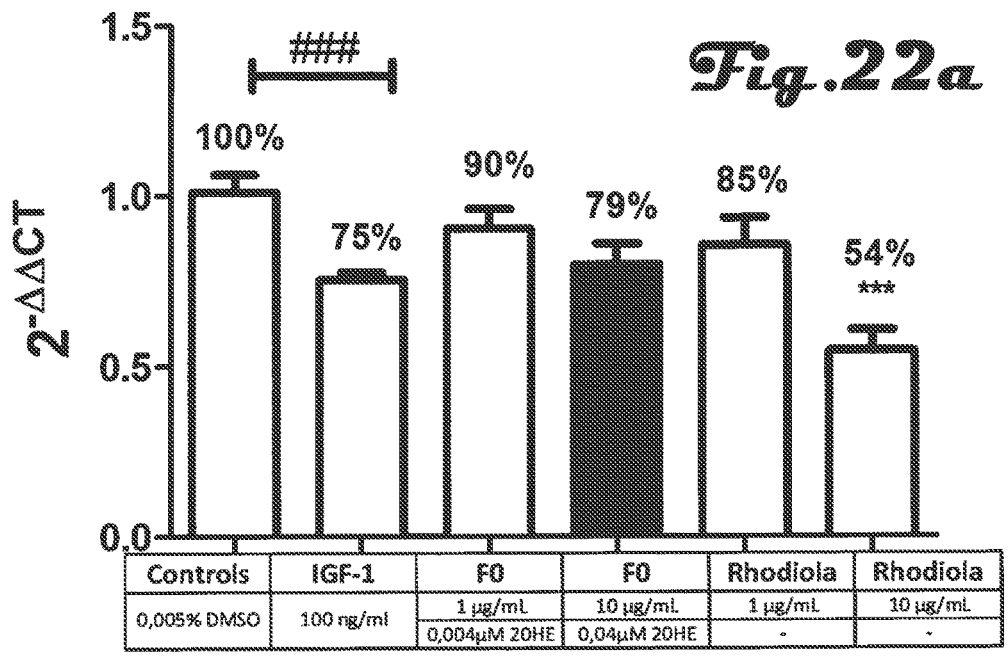
FIGS. 22a and 22b are bar graphs that depict the effect of *Rhaponticum* F0 and *Rhodiola* extracts on myostatin and atrogin gene expression in C2C12 myotubes.
Figure 22B:
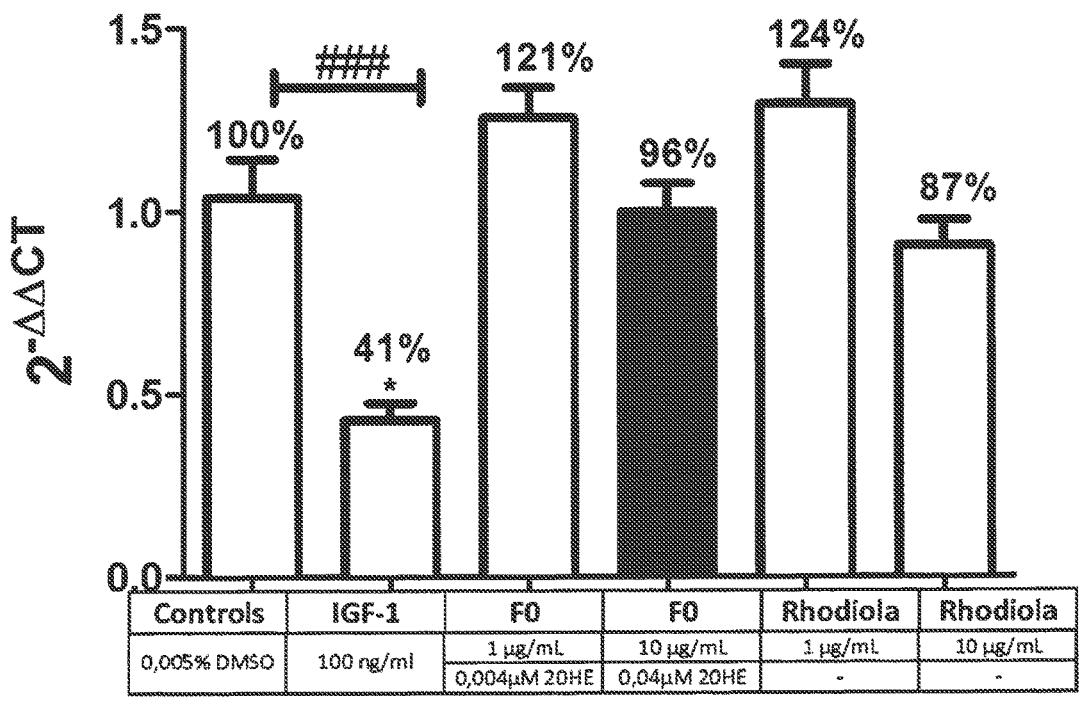
Figure 25A:
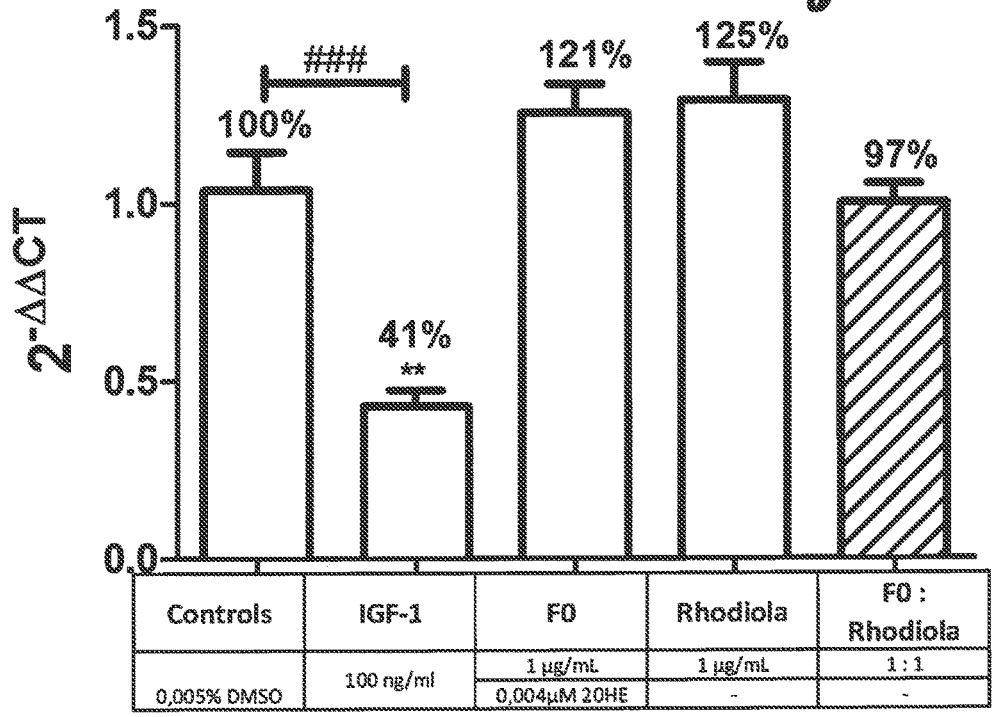
FIGS. 25a, 25b, 26a and 26b are bar graphs that depict the effect of co-incubation of *Rhaponticum* F0 and *Rhodiola* extracts on atrogin gene expression in C2C12 myotubes.
Figure 25B:
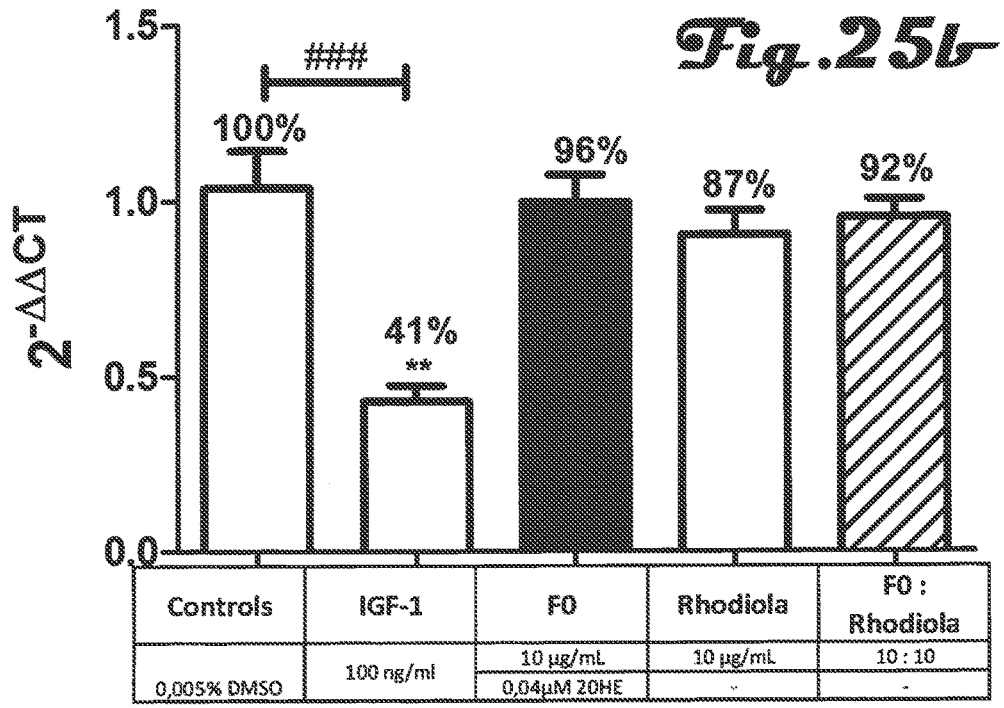
Figure 26A:
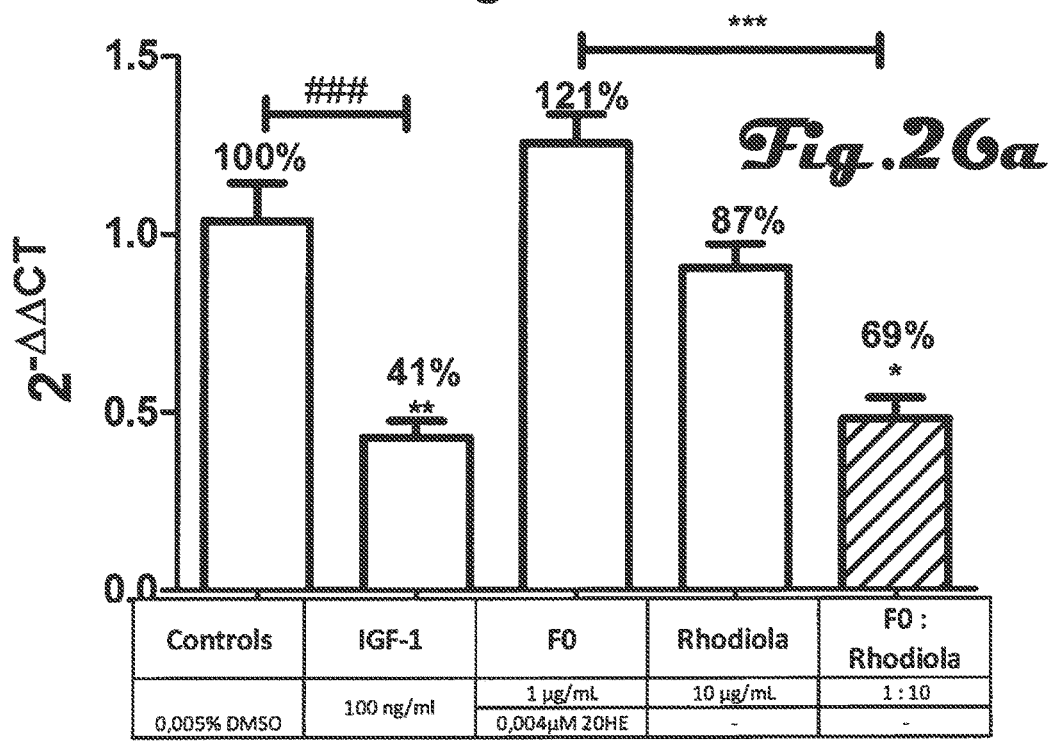
Figure 26B:
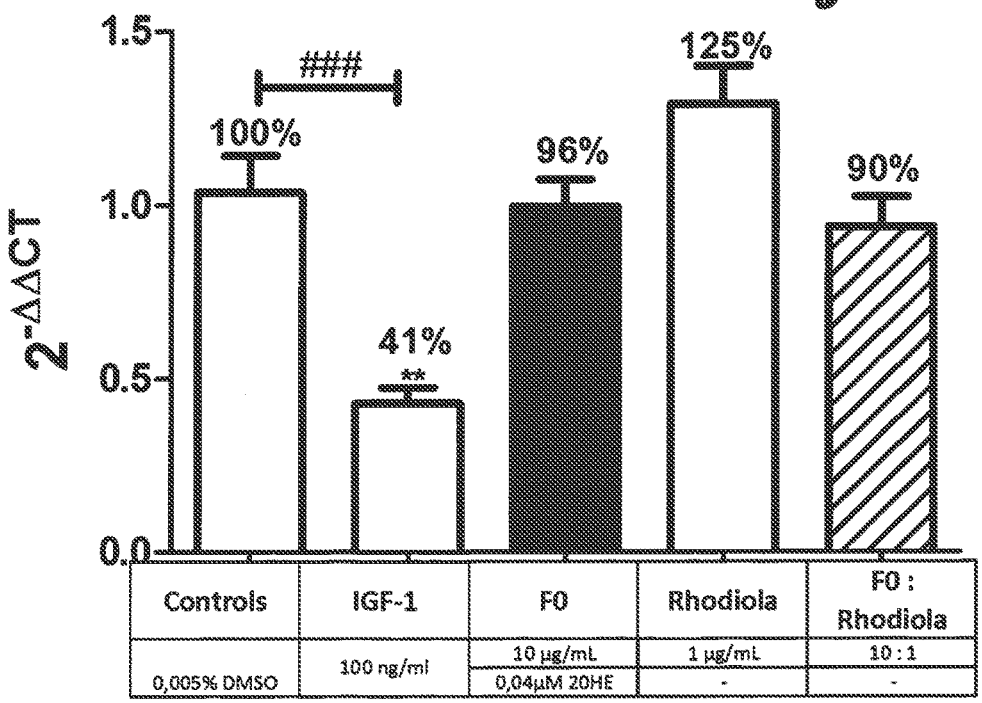

Rhodiola significantly and dose-dependently inhibited myostatin gene expression (−15% NS and −54% $p<0.001$ at low and high dose, respectively), while it had only a slight, non-significant effect on atrogin gene expression at the highest dose (−13% NS) (See FIGS. 22a and 22b).

F0 induced a slight yet non-significant reduction in myostatin gene expression (−10% NS and −21% NS at low and high dose, respectively) but did not have any effect on atrogin gene expression (+12% NS and −4% NS at low and high dose, respectively)

FIGS. 22a and 22b: Effect of Rhaponticum F0 and Rhodiola extracts on myostatin and atrogin gene expression in C2C12 myotubes.

Rhaponticum F0 and Rhodiola extracts at two different concentrations were incubated for 6 h in the presence of differentiated C2C12 myotubes. At the end of the incubation cells were lysed and RNA was extracted, converted into cDNA to perform a quantitative PCR. Mean±SEM. *$p<0.05$; $p<0.01$; *$p<0.001$ vs control value; ### $p<0.001$ vs control value (Mann-Whitney test).

Results of myostatin gene expression are presented in FIGS. 23a, 23b, 24a, and 24b.

Combination of F0 10 µg/mL & Rhodiola 1 µg/mL induced a significant decrease in myostatin gene expression (−23%; $p<0.05$ vs control) while F0 10 µg/ml alone induced only −21% (NS vs control) and Rhodiola 1 ug/ml only −15% (NS vs control). Therefore the decrease with the combination was superior to that of each extract alone and a potentiating effect was observed.

F0 and Rhodiola 1 µg/mL alone or in combination induced a slight but non-significant decrease in myostatin gene expression. The magnitude of the effect was stronger with the combination (−19% NS) compared to F0 alone (−10%) or Rhodiola alone (−15% NS) (See FIGS. 23a, 23b, 24a, and 24b).

Rhodiola 10 µg/mL strongly and significantly inhibited myostatin gene expression; however in the presence of F0 1 µg/mL or 10 µg/mL, no potentiating effect was observed as the inhibitory effect of combinations was systematically lower than that of Rhodiola (10 µg/mL) alone.

FIGS. 25a, 25b, 26a and 26b: Effect of co-incubation of Rhaponticum F0 and Rhodiola extracts on atrogin gene expression in C2C12 myotubes.

Combination of Rhaponticum F0 and Rhodiola extracts at two different concentrations each were incubated for 6 h in the presence of differentiated C2C12 myotubes. At the end of the incubation cells were lysed and RNA was extracted, converted into cDNA to perform a quantitative PCR. Mean±SEM. *$p<0.05$;  $p<0.01$; * $p<0.001$ vs control value; ### $p<0.001$ vs control value (Mann-Whitney test).

Combination of F0 1 µg/mL & Rhodiola 10 µg/mL induced a strong and significant decrease in atrogin gene expression (−31%; $p<0.05$ vs control) whereas each fraction alone did not: F0 1 ug/ml alone induced an increase by 21% (NS vs control) and Rhodiola 10 ug/ml a decrease by −13% (NS vs control). Therefore the decrease with the combination was superior to that of each extract alone and a strong potentiating effect was observed.

The combination of F0 10 µg/mL & Rhodiola 1 µg/mL decreased atrogin gene expression in a non-significant manner (−10% NS) and this decrease was superior to that of F0 alone (−4% NS) or Rhodiola alone (+25% NS).

F0 and Rhodiola 1 µg/mL had no significant effect on atrogin gene expression alone or in combination. It must be noted that the magnitude of the effect was stronger with the combination (−3% NS) compared to F0 alone (+21% NS) or Rhodiola alone (+25% NS) as depicted in FIGS. 25a, 25b, 26a and 26b.

F0 and Rhodiola 10 µg/mL had very slight but non-significant effect on atrogin gene expression alone or in combination, and no potentiating effect was observed.

In conclusion, the combination F0 1 µg/mL & Rhodiola 10 µg/mL exhibited potentiating effect on inhibition of atrogin gene expression. The decrease with the combination was superior to that of each extract alone and a strong potentiating effect was observed.

Example 16: Evaluation of 4 New Preparations of Fraction F0 from *Rhaponticum* Extract at 2 Concentrations (Step 3 as Depicted in FIG. 29a)

To improve results obtained on protein synthesis and to increase the chance to have a better and more pure product to test in animal model, the fraction F0 was differently processed and further purified to obtained new fractions. F0 Ne-ETOH corresponding to the initial F0 previously tested in EXAMPLE 12, 13, 14 and 15. F1 fraction corresponded to F1 fraction from EXAMPLE 12 and 13. After atomization of fraction F0 it was generated fraction F0 dry. After dilution of fraction F0 in aqueous solution and purification on column it was generated fraction F5'.

| Compound | % of Hydroxy-ecdysone amount (%20 HE) | Final concentration of extract after dilution in DMEM (in wells) | Final concentration in Hydroxy-ecdysone (in wells) |
|---|---|---|---|
| F0 (liquid NE-ETOH 50% extact) | 0.21% | 11.4 µg/mL | 0.05 µM |
|  |  | 22.9 µg/mL | 0.1 µM |
| F0 (Dry fraction extract) | 0.37% | 6.5 µg/mL | 0.05 µM |
|  |  | 13.0 µg/mL | 0.1 µM |
| F1 (primary aqueous extract) | 0.18% | 13.4 µg/mL | 0.05 µM |
|  |  | 26.7 µg/mL | 0.1 µM |
| F5' (ethanol fraction extract derived from F0) | 2.50% | 1.0 µg/mL | 0.05 µM |
|  |  | 1.9 µg/mL | 0.1 µM |

The C2C12 skeletal muscle cells were obtained as in EXAMPLE 12. The protein synthesis assay was performed as in EXAMPLE 13 and 14 except that radiolabelled leucine 5 µCi/mL and IGF1 100 ng/mL, F0 extract at 11.4 and 22.9 µg/ml, or F0 dry extract at 6.5 and 13 µg/ml or F1 extract at 13.4 and 26.7 µg/ml or F5' extract at 1 and 1.9 µg/ml in the presence of normal (0.8 mM) concentration of amino acids and with DMSO 0.005%. At the end of the experiments supernatants were discarded and cells were lysed in 0.1N sodium hydroxide for 30 min. The cell soluble fraction-associated radioactivity was then counted and protein quantification was determined using the coloric Lowry method.

Each condition is tested in n=6. IGF1 100 ng/ml is used as a positive control of the protein synthesis stimulation and signaling. Results of protein synthesis are expressed in cpm/µL/2.5 hrs and in % of untreated control condition (100%).

Figure 28:
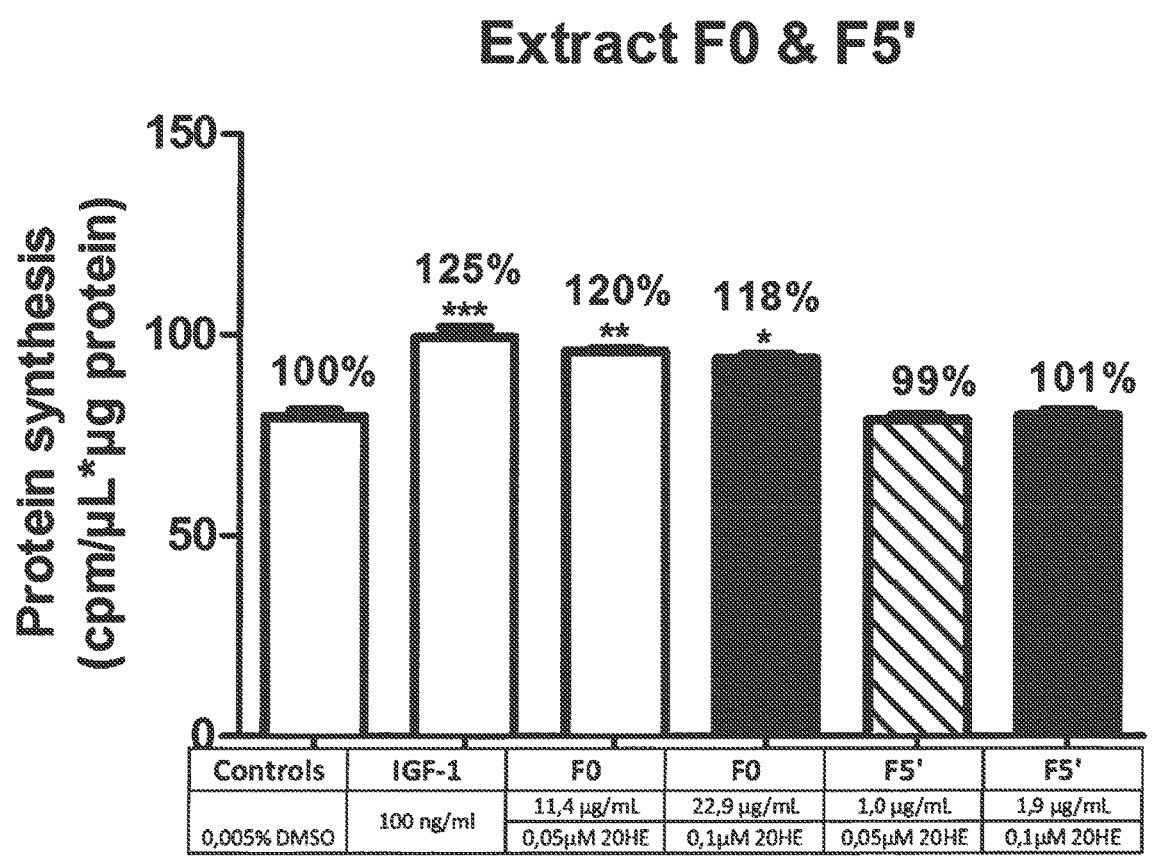

Results are presented in FIGS. 27a, 27b and 28.

IGF1 significantly induced protein synthesis in the presence of normal concentration of amino acid (+25%, $p<0.001$) as previously reported in steps 1-2a-2b (step 1+21%, $p<0.001$; step 2a+27%, $p<0.01$; step 2b+21%, $p<0.05$ vs step 3+25%, $p<0.001$). Similar results are reported in the literature in the presence of normal concentration of amino acids (Kazi A A, 2010) (Broussard S R, 2004).

*Rhaponticum* extract F0 NE-EtOH 50% (Native EtOH50% extract) significantly induced protein synthesis at 0.05 µM 20HE and 0.1 µM 20 HE (respectively +20%, $p<0.01$ and +18%, $p<0.05$). The stimulation of protein synthesis by fraction F0 was previously documented at 0.04 µM 20HE (+29%, $p<0.001$ in step 2B). At 0.05 µM and 0.1 µM effect on protein synthesis are significant but weaker than at 0.04 µM.

*Rhaponticum* extract F0 EtOH50% (dry powder form) induced protein synthesis at both concentration but the stimulation was strong and significant only at the lowest dose (+33%, $p<0.00$ at 6.5 µg/mL corresponding to 0.05 µM HE). This effect was stronger than effect observed with fraction F0 NE-EtOH 50%.

No effect of fraction F5' (purified EtOH50% extract) was observed on protein synthesis at any 20HE final concentration tested.

The non-purified aqueous fraction F1 exhibited strongest activity on protein synthesis than the NE-EtOH 50% preparation and its derived fractions. At final concentration of 0.05 µM of 20HE, F1 fraction showed similar percentage of protein synthesis stimulation than the dry F0 fraction (+30%, $p<0.001$ and +33% respectively, $p<0.001$). Whatever the final concentration of 20HE, the effect of F1 fraction on protein synthesis was similar.

Among the different fractions from *Rhaponticum* tested, F1 (aqueous extract), F0 NE-ETOH 50% (native EtOH50% extract) and dry F0 (atomized powder of F0 50% EtOH) fractions exhibited significant stimulatory effect on protein synthesis. For each positive fraction the best effect was observed at the lowest dose of 20HE (0.05 µM). The strongest effect on protein synthesis was obtained with the atomized powder of F0 50% EtOH.

On the other hand, the F5' fraction derived from F0 NE-ETOH 50% and enriched in 20HE did not stimulate protein synthesis. All these results suggest that effect on protein synthesis of *Rhaponticum* extracts are not solely dependent of 20HE concentration and that other active(s) component(s) able to promote protein synthesis is/are present in the active extracts. FIGS. 27a, 27b and 28: Determination of protein synthesis in C2C12 myotubes after incubation with different preparation of *Rhaponticum* extracts at two concentrations.

Four different preparations of *Rhaponticum* extracts at two concentrations were incubated in presence of differentiated myotubes C2C12 and tritiated leucine 5 µCi for 2 h30. At the end of incubation cells were lysed, total soluble proteins were quantified and level of tritiated leucine incorporated into cells was counted. Mean±SEM. *$p<0.05$; $p<0.01$; *$p<0.001$ vs control value.

We observed a potentiation with the combination of *Rhodiola* (1 µg/ml) and *Rhaponticum* (1 µg/ml) on the protein synthesis assay.

The protein synthesis can be stimulated via inhibition of myostatin target. Welle et al. demonstrated in mature mice that myostatin exerts a tonic inhibitory influence on the rate of myofibrillar protein synthesis even after muscles are fully developed (Welle S, 2008). Myostatin blockade or its natural absence leads to a significant increase in muscle mass (Lee S J, 2005). In our experiment we documented a decrease in myostatin gene expression after treatment of C2C12 with *Rhodiola* plant extract at 10 µg/mL (equivalent to 10 ppm) twice better than the reference IGF-1. Interestingly, Zubeldia et al reported that myotubes treated for 6 h with *Ajuga turkestanica* extract at 20 ppm (plant extract containing ecdysone including 20HE and turkesterone) significantly inhibited myostatin gene expression and inhibition was twice stronger than inhibition induced by the anabolic steroid methandrostenolone (1 µM) (Zubeldia J M, 2012).

*Rhaponticum* F0 fraction did not show significant effect on myostatin gene expression while *Rhodiola* (10 µg/mL) alone significantly reduced it. To our knowledge, no direct effect of *Rhodiola* on myostatin gene expression was reported in the literature. In addition, potentialization of the effect on myostatin gene expression inhibition with the combination of *Rhodiola* and *Rhaponticum* extracts was observed in our study. As observed for protein synthesis no potentiating effect of both extract (*Rhaponticum* and *Rhodiola*) was documented previously.

Muscle mass gain is a balance between protein synthesis, proteolysis and satellite cells differentiation. Atrogin-1 or muscle atrophy F-box (MAFbx) is a major atrophy-related E3 ubiquitin ligase highly expressed in skeletal muscle during muscle atrophy and other disease states such as sepsis, cancer cachexia, and fasting (Cong H, 2011). We explored the ubiquitin proteasome system. None of the extract alone exhibited a significant effect on atrogin gene expression. By contrast interestingly, a potentiating effect of inhibition of atrogin gene expression was observed (−31%, p<0.05) when fraction F0 of *Rhaponticum* extract was incubated in presence of *Rhodiola* extract in ration of 1:10. Cong et al. showed that reduction of atrogin using SiMAFbx adenoviruses lead to 55% of gene expression inhibition, 60% inhibition of protein level and a 20% increase in muscle mass. It was shown that atrogin targeted MyoD degradation in skeletal muscle atrophy (Lagirand-Cantaloube J, 2009).

Results on Low Amino Acid:

| LOW AMINO ACID (Step 1) | | | |
|---|---|---|---|
| Fraction | extract amount | protein synthesis | pS6K |
| IGF-1 | 100 ng/mL | 145%** | 479%** |
| F0 NE-ETOH 50% | 10 µg/mL | 115% | 195%** |
| | 100 µg/mL | 114% | 137%* |
| | 1000 µg/mL | 121%* | 231%** |
| F1 aqueous | 12.6 µg/mL | 115% | 208%** |
| | 127 µg/mL | 105% | 187%** |
| | 1265 µg/mL | 110% | 204%** |
| F3 aqueous | 2.4 µg/mL | 104% | 252%** |
| | 24.5 µg/mL | 121% | 271%** |
| | 245 µg/mL | 102% | 268%** |
| F5 EtOH 70% | 3 µg/mL | 98% | 208%** |
| | 30 µg/mL | 92% | 122% |
| | 300 µg/mL | 99% | 121% |
| F7 EtOH 70% | 10 µg/mL | 92% | 153% |
| | 100 µg/mL | 97% | 41%** |
| | 1000 µg/mL | 107% | 37%** |

In the presence of low amino acid, no significant induction of protein synthesis was reported, except with fraction F0 EtOH 50%; however, stimulation of protein synthesis or pS6K1 phosphorylation was twice lower than that induced by IGF-1. It was noted that in almost all the conditions pS6K1 signaling was activated but probably did not reach the threshold necessary to induce physiological response. Indeed, in low amino acid condition pS6K1 level was lower than that observed in control condition in the presence of normal amino acid concentration (maximum of 1.2 for best fraction versus 2.1 for control in the presence of normal amino acid concentration). Therefore, it is preferable to use plant extract in the presence of normal amino acid concentration.

F3, F5 and F5' are purified fractions from aqueous (fractions in blue) or ethanol (fractions in orange) extracts. In all these purified fractions, no stimulating activity on protein synthesis or at a lower level than that of the mother solution was observed. These data indicate that during the purification step active molecule(s) was/were lost during purification process.

| Fraction | Best stimulation of protein synthesis | [20He] |
|---|---|---|
| F1 step 3 | 130-127% *** | 0.05-0.1 µM |
| F0 EtOH 50% step 1 | 143% *** | 0.04 µM |
| F0 EtOH 50% step 3 | 120% *** | 0.05 µM |
| F0 dry step 3 | 133% *** | 0.05 µM |
| F7 EtOH 70% step 1 | 129% *** | 0.1 µM |
| Purified F5 step 1 | 123% *** | 10 µM |
| F1 step 1 | No activation | 0.1-1-10 µM |
| Purified F3 step 1 | No activation | 0.1-1-10 µM |
| Purified F5' step 3 | No activation | 0.05-0.1 µM |

No real correlation was found between 20HE concentration and stimulation of protein synthesis. However, in non purified fraction in which strongest stimulation of protein synthesis was reported the best concentration of 20HE appeared to be between 0.05 and 0.4 µM. These results suggest that 20HE was not the only active molecule involved in activation of protein synthesis. Therefore, it would be of particular interest to get information on molecule profile in the different fractions to determine which cocktail of molecules contributes to protein synthesis stimulation.

| Active Fraction | Extract amount | Protein synthesis |
|---|---|---|
| F0 | 1-5 µg/mL | low activity |
| | 10-100 µg/mL | maximal activity |
| | 1000 µg/mL | medium activity |
| F0 dry | 6.4 µg/mL | maximal activity |
| F1 step 3 | 13-26 µg/mL | maximal activity |
| F5 | 30 µg/mL | maximal activity |
| | 300 µg/mL | maximal activity |
| F7 | 3 µg/mL | maximal activity |

The maximal activity of *Rhaponticum* plant extract was observed at concentration between 10 µg/mL and 100 µg/mL. When fraction lost a part of its activity due to purification step it was observed that extract had to be tested at stronger concentration to observe similar effect on protein synthesis. Then the best concentration for in vitro evaluation of *Rhaponticum* plant extract is 10-100 µg/mL.

| | Rhaponticum | Rhodiola | Rhaponticum + Rhodiola |
|---|---|---|---|
| Protein synthesis | + + + | + + + | 0 |
| Atrogin | 0 | + + + | 0 |
| myostatin | 0 | 0 | + + + + |

*Rhaponticum* and *Rhodiola* extracts were both active on protein synthesis; each extract alone increased protein synthesis by 20-30%, reaching the upper level that could be obtained in the assay. Potentiating effect on protein synthesis should be better appreciated at the level of its signaling pathway since the maximal limit of stimulation is over 100% when pAkt or pS6K are measured.

*Rhodiola* extract induced inhibition of myostatin gene expression but a lower beneficial effect was observed when *Rhodiola* and F0 fraction of *Rhaponticum* were co-incubated. Results suggest that molecule(s) within F0 fraction was/were able to antagonize the beneficial effect of *Rhodiola* extract. Identification and pre-purification of this/these substance(s) could improve effect of co-incubation.

None of the extracts alone exhibited effect on atrogin gene expression whereas under certain condition of co-incubation (F0 1 µg/mL & *Rhodiola* 10 µg/mL) a potentiating effect on inhibition of atrogin gene expression was observed. A synergistic and beneficial effect of *Rhodiola* and *Rhaponticum* extracts was observed on proteolysis.

In conclusion, this study has shown that EtOH 50% extract of *Rhaponticum* extract was the most potent fraction among all the fractions evaluated on protein synthesis stimulation. *Rhodiola* extract also strongly increased protein synthesis. When co-incubated with F0 fraction of *Rhaponticum*, a higher effect could be shown on this parameter compared to each extract alone (when each extract was mixed at concentration of 1 μg/ml).

In parallel, *Rhodiola* extract strongly decreased myostatin gene expression at 10 μg/ml but no better effect was observed when co-incubated with *Rhaponticum* F0 fraction. It must be noted that a potentiating effect was observed on myostatin gene expression when combining *Rhodiola* (1 μg/ml) and *Rhaponticum* (1 μg/ml), whereby the expression of myostatin gene was lower (yet not significantly) compared to each extracts alone.

A synergistic inhibitory effect of the mix of extracts could be observed on atrogin gene expression suggesting a beneficial impact of the mix of *Rhaponticum* and *Rhodiola* extracts on proteolysis in addition to its effect on protein synthesis.

Example 17: Testing the Effect of Combination of *Rhodiola* Extract and *Rhaponticum* Extract on Muscle Protein Synthesis and Associated Pathway, Muscle Mass and Muscle Strength in Animal Model The combination of *Rhodiola* and *Rhaponticum* extracts was tested for its effect on physical strength, muscle weight, muscle Akt phosphorylation and protein content, plasma glucose and lactate.

The dried extract of *Rhaponticum* carthamoides root (F0-EtOH 50% dried powder) was obtained by extraction with 50% (v/v) ethanol in water as described in Example 1. The extract can preferably contain approximately (% w/w) 0.395% 20HE, 0.79% total ecdysteroids and 13.4% total polyphenol (Folin ciocalteu) based on the total dry weight of the herbal extract.

Ethanolic extract of *Rhodiola rosea* root can be obtained that preferably comprises approximately (% w/w) 3.41% salidrosides, 3.12% rosavin and 4.20% rosavins (as sum of rosarin, rosavin and rosin) based on the total dry weight of the herbal extract.

Both extracts were in a powder form with <5% humidity. Extracts were mixed at a ratio 50:50 (w/w) based on the total weight of the composition. No carrier or additional excipients were added in some tests.

This combination of the two extracts of *Rhodiola rosea* root and *Rhaponticum* carthamoides root was analyzed for target compounds:

Wister male rats were treated with the extract combination at a dose of 50 mg/kg bw (n=10) or with vehicle (n=10) for a period of 6 weeks. The combination was administered by gavage once a day.

Forelimb grip strength of the Wistar rats was evaluated before (day 0) and after 42 days of treatment (day 43) and the evolution of grip strength from day 0 to day 43 was calculated as the delta (grip strength at d43−grip strength at d0). As is well known in the art, this grip strength test aims to measure the fore and hindlimb grip strength of rats and has been used by others, for example, to measure strength following administration of 20HE (Feldman-Gorelick et al, 2008, JAFC).

Figure 30A:
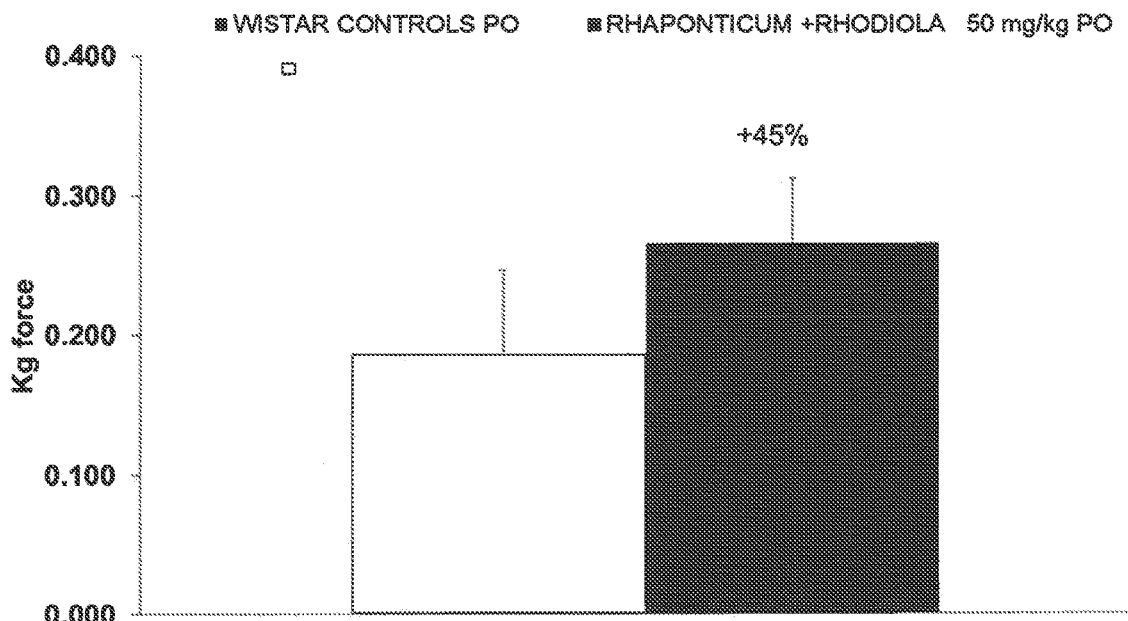
FIG. 30a is a bar graph that depicts the increase in grip strength (in Kg of force) of Wistar rats in a control group and in an experimental group after 42 days of treatment with a *Rhaponticum* and *Rhodiola* composition.
Figure 30B:
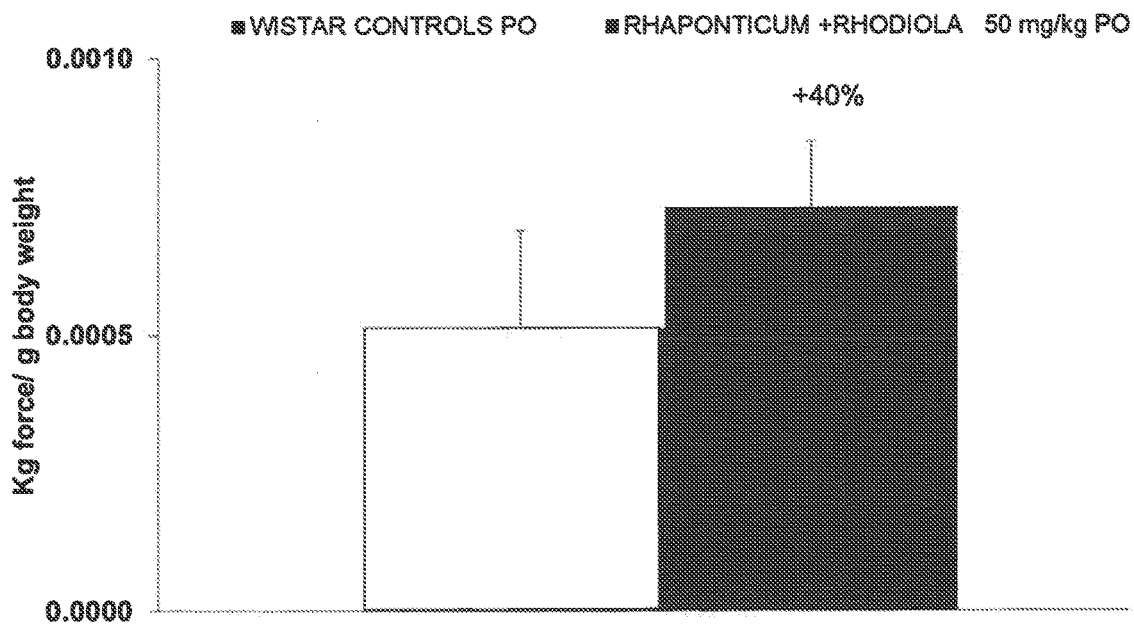
FIG. 30b is a bar graph that depicts the increase in grip strength (in Kg of force/g body weight) of Wistar rats in the control group and in the experimental group after 42 days of treatment with a *Rhaponticum* and *Rhodiola* composition.

As illustrated in FIG. 30a, the increase of the delta grip strength in the blend-treated group was 45% higher than the increase observed in the non-treated control group. Additionally, as illustrated in FIG. 30b, when delta grip strength is alternatively reported based on body weight (i.e., Kg force/g body weight), the blend-treated group was still 40% higher than the increase observed in the non-treated control group.

Rat weight was measured twice a week, every week of the treatment period. Plasma glucose and lactate was measured before treatment and after 6 weeks of treatment (before and after exercise).

Figure 31A:
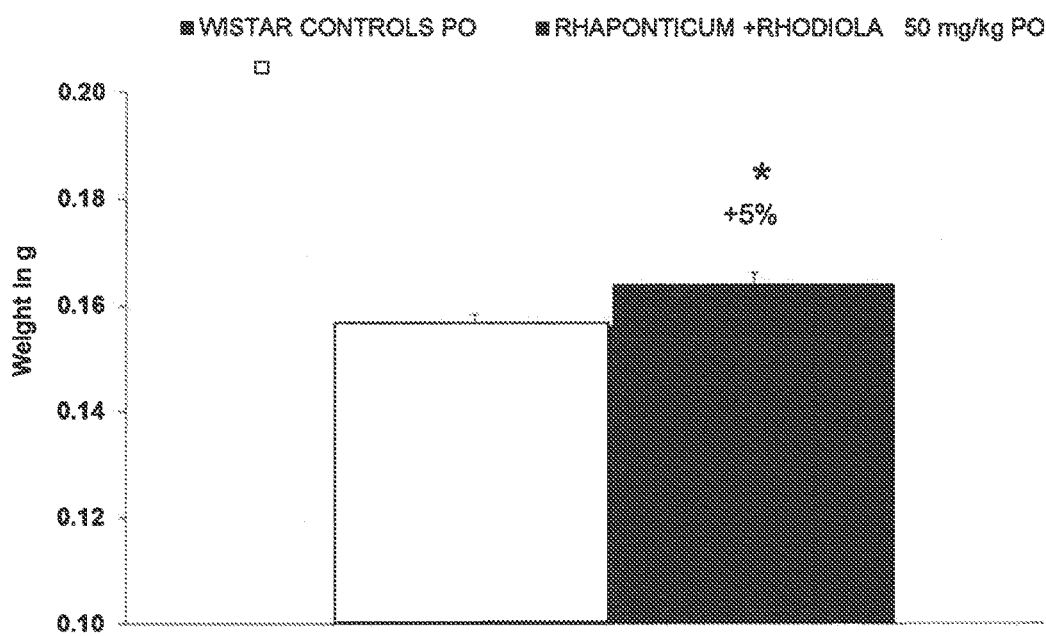
FIG. 31a is a bar graph that depicts Extensor Digitorum Longus (EDL) weight (in grams) of Wistar rats in the control group and in the experimental group after 42 days of treatment with a *Rhaponticum* and *Rhodiola* composition.
Figure 31B:
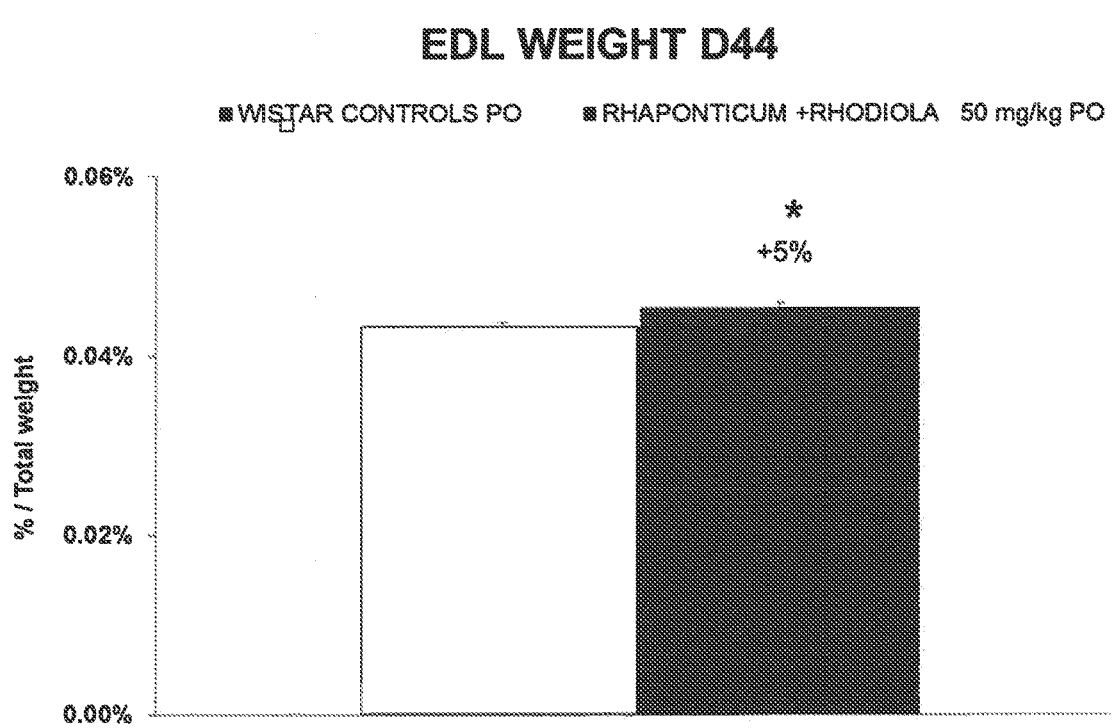
FIG. 31b is a bar graph that depicts EDL weight (as percent of total body weight) of Wistar rats in the control group and in the experimental group after 42 days of treatment with a *Rhaponticum* and *Rhodiola* composition.
Figure 32A:
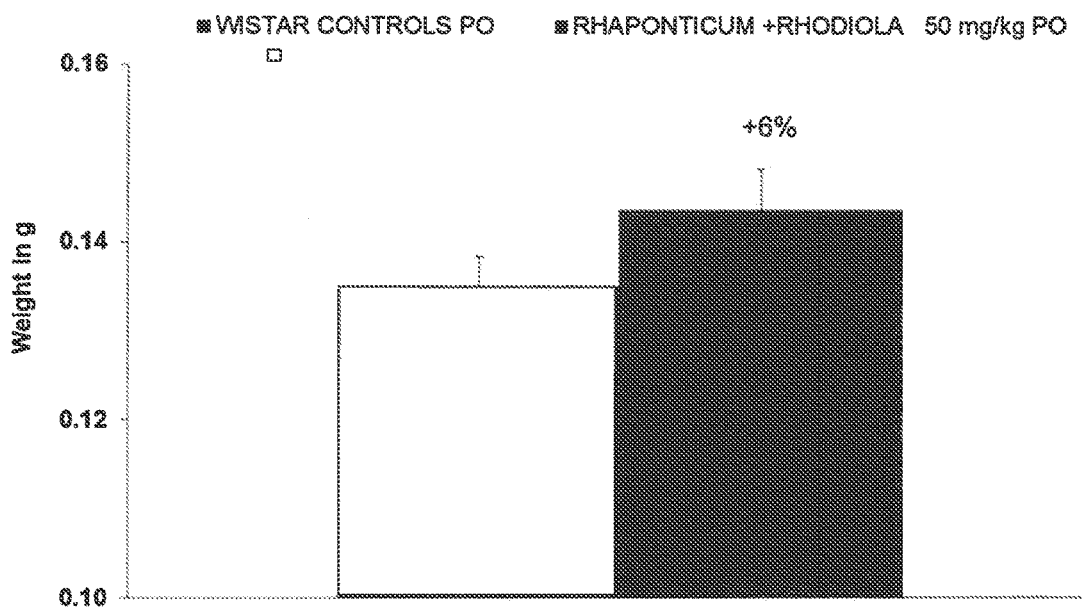
FIG. 32a is a bar graph that depicts soleus weight (in grams) of Wistar rats in the control group and in the experimental group after 42 days of treatment with a *Rhaponticum* and *Rhodiola* composition.
Figure 32B:
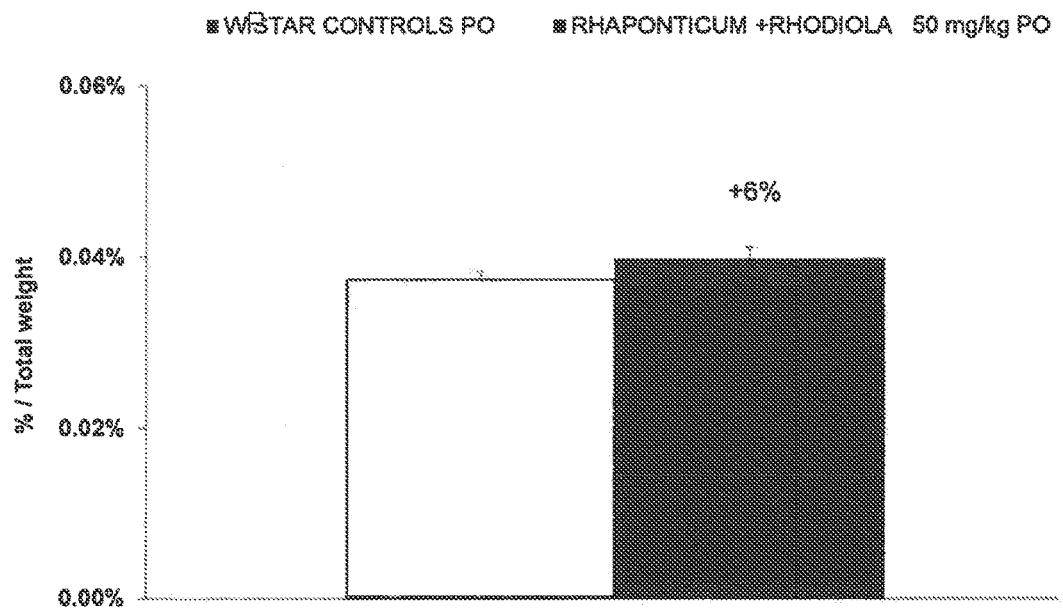
FIG. 32b is a bar graph that depicts soleus weight (as percent of total body weight) of Wistar rats in the control group and in the experimental group after 42 days of treatment with a *Rhaponticum* and *Rhodiola* composition.

At the end of 43 days of treatment (day 44), after the grip strength test and blood sampling, animals were sacrificed. Hindlimb and forelimb muscles of the Wistar rats were removed (Extensor Digitorum Longus (EDL), Soleus, Quadriceps, Tibialis and Triceps) and weighed. As illustrated in FIGS. 31a and 31b, an increase of 5% in the EDL weight and EDL weight-to-body-weight ratio was observed (p<0.05 Mann-Whitney for both). Additionally, as illustrated in FIGS. 32a and 32b, an increase was also found in the Soleus muscle weight and soleus weight-to-body-weight ratio. No substantial modification of muscle weight was documented in the other muscles.

Figure 33A:
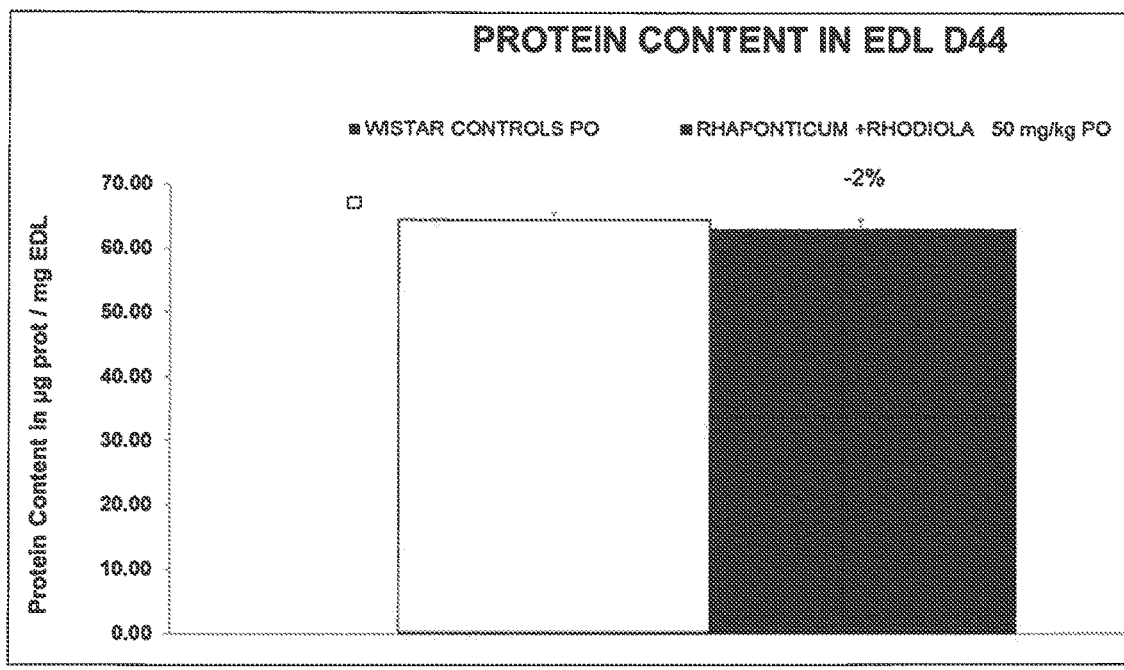
FIG. 33a is a bar graph that depicts protein content in the Extensor Digitorum Longus (EDL) of Wistar rats in the control group and in the experimental group after 42 days of treatment with a *Rhaponticum* and *Rhodiola* composition.
Figure 33B:
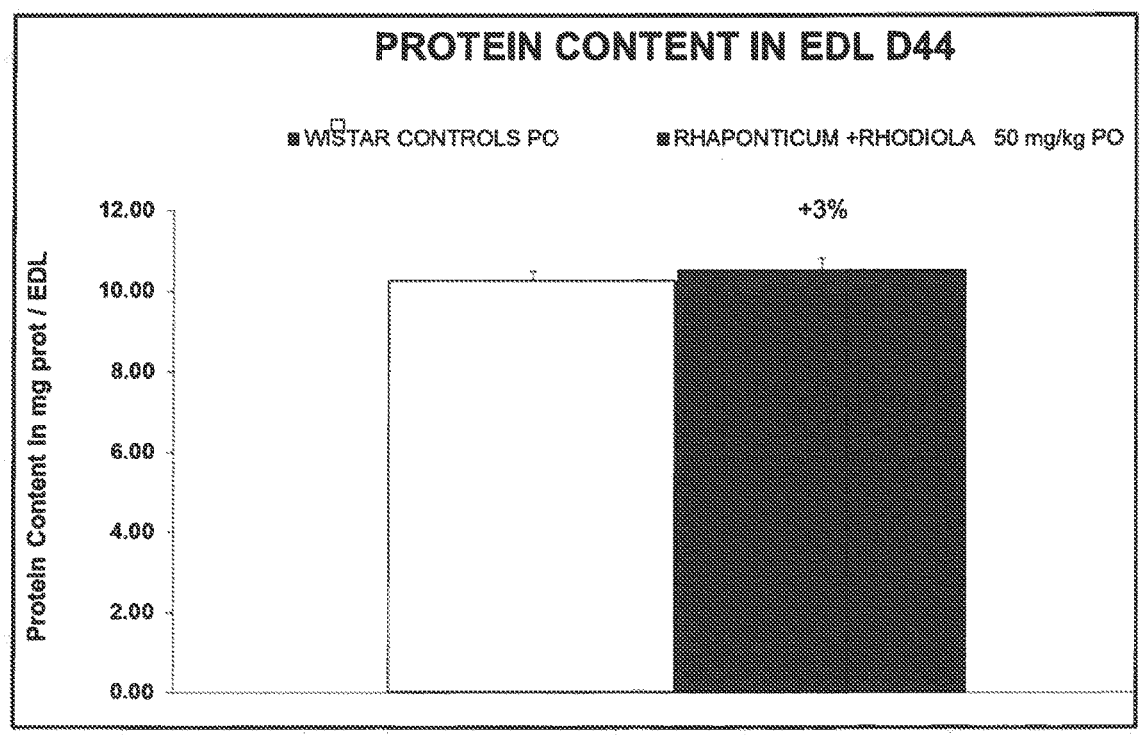
FIG. 33b is a bar graph that depicts protein content in the EDL of Wistar rats in the control group and in the experimental group after 42 days of treatment with a *Rhaponticum* and *Rhodiola* composition.
Figure 34A:
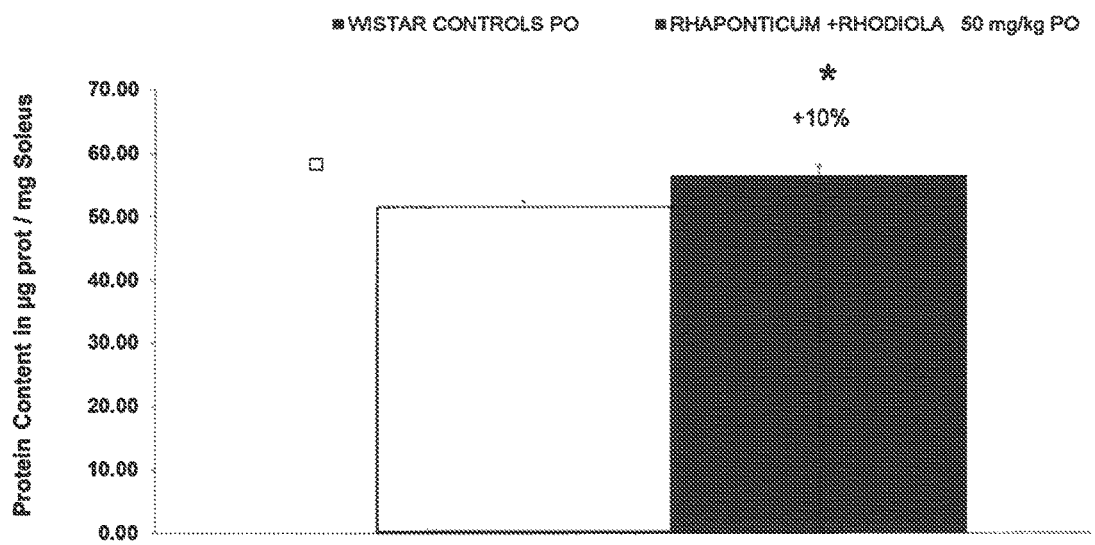
FIG. 34a is a bar graph that depicts protein content in the soleus of Wistar rats in the control group and in the experimental group after 42 days of treatment with a *Rhaponticum* and *Rhodiola* composition.
Figure 34B:
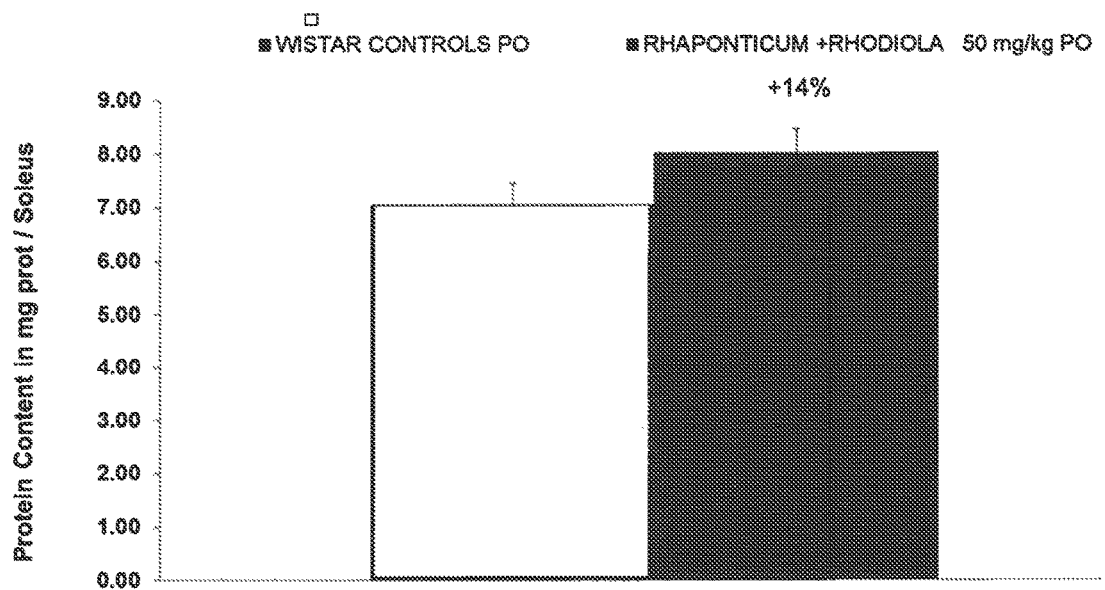
FIG. 34b is a bar graph that depicts protein content in the soleus of Wistar rats in the control group and in the experimental group after 42 days of treatment with a *Rhaponticum* and *Rhodiola* composition.

Protein content and Akt phosphorylation were measured in the muscles sampled. The combination of *Rhaponticum* and *Rhodiola* administered at 50 mg/kg for 6 weeks did not significantly change the amount of protein within the EDL muscle (in μg of protein per mg of tissue; FIG. 33a) and the total quantity of protein of the EDL (mg per muscle; FIG. 33b). However, an increase in protein content (in μg of protein per mg of tissue; +10%, p=0.08, FIG. 34a) and the total quantity protein of the EDL (mg per muscle; +14%, FIG. 34b) was observed within soleus muscle in Wistar rats.

Example 18: Testing the Effect of 8 Weeks Supplementation with Combination of *Rhodiola* Extract and *Rhaponticum* Extract on Body Composition, Muscle Mass, Muscle Strength and Exercise Resistance in Recreationally Active Men During a Resistance-Training Program Given the results of in vitro and animal studies, it is postulated that supplementing recreationally active men with the blend disclosed while resistance training may provide added benefits in terms of increasing strength and muscle size. The purpose of this study is to determine the effects of the disclosed preparation supplemented to recreationally active men during 8 weeks of dynamic constant external resistance (DCER) training on strength and thigh muscle cross-sectional area.

The primary objective of this study is to evaluate the effects of 8-week supplementation with the combination of *Rhaponticum*/*Rhodiola* extracts (see example 17 for description of the blend) on muscle strength (1-RM leg press and bench press). The trial can evaluate upper and lower body muscular strength using 1RM and Bench and Leg press exercise testing at 4 and 8 weeks.

Secondary objectives are to evaluate the effects of 8-week supplementation with the combination of *Rhaponticum*/ *Rhodiola* extracts on body composition and muscle mass (DXA), muscle protein content, blood glucose and resistance/time to exhaustion during resistance-training exercise.

The study can be a randomized, double-blinded, placebo controlled, parallel group study. According to their randomization, participants can take low (100 mg) or high (400 mg) dose of the supplement or a placebo every day during 8 weeks. Changes in muscular strength (upper and lower body muscular strength) can be assessed at week 0 (baseline), week 4 and week 8 using 1RM and Bench and Leg press. Changes in body composition and muscle mass can be assessed at week 0 and week 8 using DEXA. Muscle biopsy and analysis can be performed at week 0 and week 8. Resistance/time to exhaustion can be measured by augmentation of the repetition of 1-RM at week 0 (pre-treatment; baseline), and week 8. Mental fatigue can be evaluated using the Rating of perceived exertion (RPE) questionnaire at week 0 (pre-treatment; baseline), and at week 8.

In order to verify the acute metabolic responses to intake of the supplement (at the beginning and end of the supplementation phase), an acute intake of the supplement can be performed, following a randomized, double-blinded, crossover, placebo controlled. Following acute intake of low (200 mg) or high (400 mg) dose of the supplement or of the placebo, muscular strength (upper and lower body muscular strength) can be assessed as described above. Biological parameters such as blood glucose and blood lactate can be measured.

For the study, healthy, recreationally active college-aged males (aged 18-35 y for instance) can be recruited to take part in this study. Participants can be enrolled in the study if they fulfill all inclusion criteria and present none of the exclusion criteria (determined by questionnaires). Ethical approval can be gained from the ethics committee of the appropriate university.

Participants can be included in the study if they:
Are non-smokers;
Aged 18 to 35 yrs old;
With a BMI 19-29.9 kg/m$^2$;
Are weight stable (i.e. have not gained or lost more than 3 kg/m$^2$ in the last 3 months);
Are recreationally active, i.e. go to the gym approximately twice a week but do not follow any intensive-training or competition program (type of sports they recreationally do and frequency/intensity to be determined);
Have been weight training at least 2 times a week for the 3 months preceding the study commencement;
Do not take any medication (set a limited duration prior to study commencement) and/or has not taken within the last month any dietary supplements thought by the investigator to influence metabolism, body weight and/or appetite; and
Have not taken ergogenic levels of nutritional supplements that may affect muscle mass (e.g. creatine, HMB etc) and/or supplements that can affect anabolic/catabolic hormone levels (e.g. androstenedione, DHEA etc.) within 1 month (tbd) prior to study commencement.

Participants will be excluded if they:
Are smokers;
Go to the gym more than twice a week and/or follow any intensive-training or competition program (unwanted type of sports and frequency/intensity to be determined);
Have a current diagnosis of a significant medical condition;
Have any history or symptoms of metabolic, endocrine or cardiac disorders;
Take any medication or supplements and/or have taken within the last month any dietary supplements thought by the investigator to influence metabolism, body weight and/or appetite; or
Have taken ergogenic levels of nutritional supplements that may affect muscle mass (e.g. creatine, HMB etc) and/or supplements that can affect anabolic/catabolic hormone levels (e.g. androstenedione, DHEA etc.) within 1 month (tbd) prior to study commencement.

Participants can be allocated into one of two independent groups: treatment or placebo (20 participants in each group). Groups can be matched as closely as possible based on physical characteristics.

The study product can be the combination of the extracts of *Rhodiola* and *Rhaponticum* as described in EXAMPLE 17. Two doses can be tested in the study: a low dose (100 mg) and high dose (400 mg) of the test product. A matching, inert placebo can be used and consisted in cellulose.

All participants can complete a strength-based test before the supplementation phase (0 weeks) and at 4 weeks and 8 weeks. One repetition maximum (1RM; the heaviest weight that can be lifted in a specific exercise with correct form) can be assessed in the upper and lower body by bench press (using the Smith machine) and leg press exercises, respectively.

Before and after 8 weeks supplementation, participant's height and weight can be recorded as well as limb girths and waist circumference. Body composition and muscle weight can be assessed by DEXA at baseline (0 weeks) and after 8 weeks, the day before 1-RM exercise.

Muscle biopsies pre- and post-supplementation can be performed to measure the phosphorylated protein versus total protein, protein analysis, Akt/pS6K1 pathways, and muscle fiber diameter size. Blood glucose can also be measured.

For resistance/time to exhaustion, these parameters can be measured by augmentation of the repetition of 1-RM. Mental fatigue can be evaluated using the Rating of perceived exertion (RPE) questionnaire.

All participants can complete an 8 week supervised training programme of two sessions per week to verify for homogeneity of exercise between participants. Training load can be a set percentage of baseline 1RM measurements and the training programme can progress in intensity every 2 weeks. Participants can train 2-3 times a week under supervision of a qualified strength and conditioning coach. All training sessions can take place in the morning and each session can last approximately 90 min. Each session can consist of a standardized warm-up, 4×6 reps of each exercise (with a 4 min recovery between sets) and a cool down. Exercises targeting the musculature of the upper (e.g., bench press, shoulder press and tricep weighted dips) and lower (e.g., leg press and leg extension, hamstring curls) body can be performed. Rating of perceived exertion can be recorded at intervals during the training sessions. All participants can be taught correct techniques for each exercise before the study commences.

In order to control for protein intake in the participants diet, a nutritionist advised on diets favouring protein intake and dietary records in the form of 24-hour dietary recall can be used and analyzed at weeks 0, 4 and 8.

Mean values at 0, 4 and 8 weeks can be computed. Change from baseline can be assessed at each time point and within each group using repeated measure ANOVA (or one-way ANOVA if only two time points).

Also, change from baseline ($\Delta T_x - T_0$) can be calculated for each variable and the mean changes can be compared between groups using multiple-way ANOVA.

Results are expected to show an increase in muscle mass, in muscle strength (1-RM), muscle fiber size and protein content. Supplementation is expected to increased time to exhaustion/resistance to exercise and improved the threshold of mental fatigue.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

What is claimed is:

1. A composition comprising a *Rhaponticum* extract and a *Rhodiola* extract comprising at least 4.5% total rosavins, wherein the mass ratio of the *Rhaponticum* extract and the *Rhodiola* extract is about between 60:40 and 80:20 based on the total weight of the composition.

2. The composition of claim 1, wherein the mass ratio of the *Rhaponticum* extract and the *Rhodiola* extract is about 75:25.

3. The composition of claim 1, wherein the composition comprises about 0.1% to 10% ecdysterones.

4. The composition of claim 1, wherein the composition comprises about 0.5% to 3% ecdysterones.

5. The composition of claim 1, wherein the *Rhaponticum* extract comprises about 0.1-10% ecdysteroids.

6. The composition of claim 1, wherein the *Rhaponticum* extract comprises about 04% to 5% ecdysteroids.

7. The composition of claim 1, wherein the composition comprises about 0.1% to 5.0% of 20-hydroxyecdysone.

8. The composition of claim 1, wherein the *Rhodiola* extract comprises about 1% to 4% salidrosides.

9. The composition of claim 1, wherein the *Rhodiola* extract comprises about 4.5% to 6% total rosavins.

10. The composition of claim 1, wherein the *Rhodiola* extract comprises about 4.5% to 5% rosavin.

11. The composition of claim 1, wherein the composition comprises about 50% to 99% *Rhodiola* extract.

12. The composition of claim 1, wherein the *Rhodiola* extract comprises:

about 1% to 4% salidrosides;
about 2% to 5% rosavin, and
about 4.5% to 6% total rosavins; and
wherein the extract of *Rhaponticum* comprises:
about 0.1% to 5.0% 20-hydroxyecdysone, and
about 0.1% to 10% total ecdysterones which includes said about 0.1% to 5.0% 20-hydroxyecdysone.

13. A pharmaceutical formulation comprising the composition of claim 1, wherein said formulation is formulated for oral administration.

14. The pharmaceutical formulation of claim 13, wherein said formulation further comprises a pharmaceutically-acceptable carrier.

15. The composition of claim 1, wherein the *Rhaponticum* extract comprises at least 4.1% total phenolic compounds.

16. A method for increasing protein synthesis in a subject comprising orally administering to the subject a formulation comprising the composition of claim 1.

17. The method of claim 16, wherein the subject is administered about 5-50 mg/kg/day of the composition.

18. The method of claim 16, wherein the subject is administered about 200-500 mg/day of the composition.

19. The method of claim 16, wherein the subject is administered about 50-2000 mg/day of the composition.

20. The method of claim 16, wherein the formulation further comprises a pharmaceutically-acceptable carrier.

21. A method for reducing protein proteolysis in a subject comprising orally administering to the subject a formulation comprising the composition of claim 1.

22. The method of claim 21, wherein the subject is administered about 5-50 mg/kg/day of the composition.

23. The method of claim 21, wherein the subject is administered about 200-500 mg/day of the composition.

24. The method of claim 21, wherein the subject is administered about 50-2000 mg/day of the composition.

25. The method of claim 21, wherein the subject is human.

26. The method of claim 21, wherein the formulation further comprises a pharmaceutically-acceptable carrier.

* * * * *